US010066018B2

(12) United States Patent
Igawa et al.

(10) Patent No.: US 10,066,018 B2
(45) Date of Patent: *Sep. 4, 2018

(54) ANTIBODY CONSTANT REGION VARIANT

(71) Applicant: CHUGAI SEIYAKU KABUSHIKI KAISHA, Tokyo (JP)

(72) Inventors: Tomoyuki Igawa, Shizuoka (JP); Atsuhiko Maeda, Shizuoka (JP); Hirotake Shiraiwa, Shizuoka (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/962,293

(22) Filed: Dec. 8, 2015

(65) Prior Publication Data

US 2016/0159915 A1 Jun. 9, 2016

Related U.S. Application Data

(63) Continuation of application No. 13/257,112, filed as application No. PCT/JP2010/054769 on Mar. 19, 2010, now Pat. No. 9,228,017.

(30) Foreign Application Priority Data

Mar. 19, 2009 (JP) ................................ 2009-068630

(51) Int. Cl.
*C07K 16/28* (2006.01)

(52) U.S. Cl.
CPC ...... *C07K 16/2866* (2013.01); *C07K 2317/52* (2013.01); *C07K 2317/522* (2013.01); *C07K 2317/526* (2013.01); *C07K 2317/53* (2013.01); *C07K 2317/90* (2013.01); *C07K 2317/92* (2013.01); *C07K 2317/94* (2013.01)

(58) Field of Classification Search
CPC ........ C07K 2317/522; C07K 2317/526; C07K 2317/53; C07K 2317/94; C07K 2317/52; C07K 2317/90
USPC .................................... 424/133.1; 530/387.3
See application file for complete search history.

(56) References Cited

U.S. PATENT DOCUMENTS

| | | |
|---|---|---|
| 5,126,250 A | 6/1992 | McDonough et al. |
| 5,322,678 A | 6/1994 | Morgan et al. |
| 5,455,030 A | 10/1995 | Ladner et al. |
| 5,468,634 A | 11/1995 | Liu |
| 5,639,641 A | 6/1997 | Pedersen et al. |
| 5,670,373 A | 9/1997 | Kishimoto |
| 5,795,965 A | 8/1998 | Tsuchiya et al. |
| 5,817,790 A | 10/1998 | Tsuchiya et al. |
| 5,859,205 A | 1/1999 | Adair et al. |
| 5,888,510 A | 3/1999 | Kishimoto et al. |
| 5,945,311 A | 8/1999 | Lindhofer et al. |
| 5,990,286 A | 11/1999 | Khawli et al. |
| 6,018,032 A | 1/2000 | Koike et al. |
| 6,126,980 A | 10/2000 | Smith et al. |
| 6,309,636 B1 | 10/2001 | do Couto et al. |
| 6,329,511 B1 | 12/2001 | Vasquez et al. |
| 6,485,943 B2 | 11/2002 | Stevens et al. |
| 6,677,436 B1 | 1/2004 | Sato et al. |
| 6,723,319 B1 | 4/2004 | Ito et al. |
| 6,884,879 B1 | 4/2005 | Baca et al. |
| 6,913,747 B1 | 7/2005 | Co et al. |
| 7,052,873 B2 | 5/2006 | Tsuchiya |
| 7,122,637 B2 | 10/2006 | Presta |
| 7,217,797 B2 | 5/2007 | Hinton et al. |
| 7,276,585 B2 | 10/2007 | Lazar et al. |
| 7,479,543 B2 | 1/2009 | Tsuchiya et al. |
| 7,482,440 B2 | 1/2009 | Maeda et al. |
| 8,562,991 B2 | 10/2013 | Igawa et al. |
| 8,575,317 B2 | 11/2013 | Kuramochi et al. |
| 8,592,562 B2 | 11/2013 | Kannan et al. |
| 9,096,651 B2 | 8/2015 | Igawa et al. |
| 9,228,017 B2 | 1/2016 | Igawa et al. |

(Continued)

FOREIGN PATENT DOCUMENTS

| | | |
|---|---|---|
| AR | 068564 | 11/2009 |
| AU | 2007/255753 | 12/2007 |

(Continued)

OTHER PUBLICATIONS

Amgen vs Sanofi and Regeron (Case: 17-1480 Document: 176 Filed: Feb. 6, 2018).*
Batra et al., "Pharmacokinetics and biodistribution of genetically engineered antibodies," *Curr Opin Biotechnol.*, Dec. 2002;13(6):603-8.
Smolen et al., "Interleukin-6: a new therapeutic target," *Arthritis Res Ther.*, 2006;8 Suppl 2:S5. Epub Jul. 28, 2006.
Dall'Acqua et al., "Increasing the affinity of a human IgG1 for the neonatal Fc receptor: biological consequences," *J. Immunol.*, Nov. 1, 2002; 169(9):5171-80.
Gramer et al., "Production of stable bispecific IgG1 by controlled Fab-arm exchange: scalability from bench to large-scale manufacturing by application of standard approaches," *MAbs.*, Nov.-Dec. 2013; 5(6):962-73. doi: 10.4161/mabs.26233. Epub Aug. 22, 2013.
Klein et al., "Progress in overcoming the chain association issue in bispecific heterodimeric IgG antibodies," *MAbs.*, Nov.-Dec. 2012; 4(6):653-63. doi: 10.4161/mabs.21379. Epub Aug. 27, 2012.
Labrijn et al., "Efficient generation of stable bispecific IgG1 by controlled Fab-arm exchange," *Pro Natl Acad Sci U S A.*, Mar. 26, 2013; 110(13):5145-50. doi: 10.1073/pnas.1220145110. Epub Mar. 11, 2013.

(Continued)

*Primary Examiner* — Lynn A Bristol
(74) *Attorney, Agent, or Firm* — Fish & Richardson P.C.

(57) ABSTRACT

By means of amino acid sequence alterations, the present inventors succeeded in providing constant regions that can confer antibodies with favorable properties, particularly as pharmaceuticals. The variants of the constant regions provided by the present invention will remarkably reduce heterogeneity when applied to antibody production. That is, homogeneity of antibodies can be maintained at a high level by introducing the alterations provided by the present invention into the antibody heavy chain constant regions. More specifically, decrease in homogeneity caused by —SS— bond linkage differences in the heavy chains of antibody molecules can be prevented. Furthermore, in a preferred embodiment of the present invention, pharmacokinetics of antibodies can be improved and decrease in homogeneity caused by deletion of the C terminus in the antibody constant region can be ameliorated.

47 Claims, 9 Drawing Sheets

Specification includes a Sequence Listing.

(56) References Cited

U.S. PATENT DOCUMENTS

| | | |
|---|---|---|
| 9,340,615 B2 | 5/2016 | Maeda et al. |
| 9,399,680 B2 | 7/2016 | Kuramochi et al. |
| 9,527,926 B2 | 12/2016 | Ho et al. |
| 9,556,279 B2 | 1/2017 | Niwa et al. |
| 9,637,557 B2 | 5/2017 | Scheer et al. |
| 9,670,269 B2 | 6/2017 | Igawa et al. |
| 9,688,762 B2 | 6/2017 | Igawa et al. |
| 2001/0001663 A1 | 5/2001 | Kishimoto et al. |
| 2002/0142374 A1 | 10/2002 | Gallo et al. |
| 2002/0147326 A1 | 10/2002 | Chaiklin et al. |
| 2002/0164339 A1 | 11/2002 | Do et al. |
| 2002/0164668 A1 | 11/2002 | Durham et al. |
| 2002/0187150 A1 | 12/2002 | Mihara et al. |
| 2003/0125520 A1 | 7/2003 | Maeda et al. |
| 2003/0190311 A1 | 10/2003 | Dall'Aqua et al. |
| 2003/0215838 A1 | 11/2003 | Sprecher et al. |
| 2003/0224397 A1 | 12/2003 | Lowman et al. |
| 2003/0224487 A1 | 12/2003 | Sprecher et al. |
| 2004/0071706 A1 | 4/2004 | Ito et al. |
| 2004/0081651 A1 | 4/2004 | Karpusas et al. |
| 2004/0223970 A1 | 11/2004 | Afar et al. |
| 2004/0236080 A1 | 11/2004 | Aburatani et al. |
| 2005/0095243 A1 | 5/2005 | Chan et al. |
| 2005/0130224 A1 | 6/2005 | Saito et al. |
| 2005/0142133 A1 | 6/2005 | Lazar et al. |
| 2005/0142635 A1 | 6/2005 | Tsuchiya et al. |
| 2005/0191293 A1 | 9/2005 | Deshpande et al. |
| 2005/0244403 A1 | 11/2005 | Lazar et al. |
| 2005/0261229 A1 | 11/2005 | Gillies et al. |
| 2006/0019342 A1 | 1/2006 | Dall Acqua et al. |
| 2006/0024298 A1 | 2/2006 | Lazar et al. |
| 2006/0063228 A1 | 3/2006 | Kasaian et al. |
| 2006/0121022 A1 | 6/2006 | Koga et al. |
| 2006/0134709 A1 | 6/2006 | Stavenhagen et al. |
| 2006/0141456 A1 | 6/2006 | Edwards et al. |
| 2006/0160184 A1 | 7/2006 | Hoogenboom et al. |
| 2006/0182743 A1 | 8/2006 | Bilsborough |
| 2006/0194280 A1 | 8/2006 | Dillon et al. |
| 2006/0204493 A1 | 9/2006 | Huang et al. |
| 2006/0275282 A1 | 12/2006 | Moore et al. |
| 2006/0292147 A1 | 12/2006 | Yoshizaki et al. |
| 2007/0036785 A1 | 2/2007 | Kishimoto et al. |
| 2007/0036799 A1 | 2/2007 | Stavenhagen et al. |
| 2007/0041978 A1 | 2/2007 | Hattori et al. |
| 2007/0054354 A1 | 3/2007 | Humphreys et al. |
| 2007/0059312 A1 | 3/2007 | Baca et al. |
| 2007/0110757 A1 | 5/2007 | Wei et al. |
| 2007/0134234 A1 | 6/2007 | Smith et al. |
| 2007/0148163 A1 | 6/2007 | Takahashi et al. |
| 2007/0148164 A1 | 6/2007 | Farrington et al. |
| 2007/0160611 A1 | 7/2007 | Yao et al. |
| 2007/0224174 A1 | 9/2007 | Kang et al. |
| 2007/0280945 A1 | 12/2007 | Stevens et al. |
| 2008/0063635 A1 | 3/2008 | Takahashi et al. |
| 2008/0075712 A1 | 3/2008 | Hattori et al. |
| 2008/0125579 A1 | 5/2008 | Owens et al. |
| 2008/0166756 A1 | 7/2008 | Tsuchiya et al. |
| 2008/0219971 A1 | 9/2008 | Smith et al. |
| 2009/0117097 A1 | 5/2009 | Igawa et al. |
| 2009/0202556 A1 | 8/2009 | Ohta et al. |
| 2009/0208416 A1 | 8/2009 | Moretta et al. |
| 2009/0221803 A1 | 9/2009 | Dall'Acqua et al. |
| 2009/0263392 A1 | 10/2009 | Igawa et al. |
| 2009/0291076 A1 | 11/2009 | Morichika et al. |
| 2009/0324589 A1 | 12/2009 | Igawa et al. |
| 2010/0003254 A1 | 1/2010 | Hattori et al. |
| 2010/0004429 A1 | 1/2010 | Kai et al. |
| 2010/0008907 A1 | 1/2010 | Nishimoto et al. |
| 2010/0015133 A1 | 1/2010 | Igawa et al. |
| 2010/0055092 A1 | 3/2010 | Hasegawa et al. |
| 2010/0239577 A1 | 9/2010 | Igawa et al. |
| 2010/0247523 A1 | 9/2010 | Kano et al. |
| 2010/0285030 A1 | 11/2010 | Bowdish et al. |
| 2010/0286374 A1 | 11/2010 | Kannan et al. |
| 2010/0291072 A1 | 11/2010 | Lowman et al. |
| 2010/0297697 A1 | 11/2010 | Ambrosius et al. |
| 2010/0298542 A1 | 11/2010 | Igawa et al. |
| 2010/0331527 A1 | 12/2010 | Davis et al. |
| 2011/0044984 A1 | 2/2011 | Kittazawa et al. |
| 2011/0076275 A1 | 3/2011 | Igawa et al. |
| 2011/0098450 A1 | 4/2011 | Igawa et al. |
| 2011/0111406 A1 | 5/2011 | Igawa et al. |
| 2011/0129459 A1 | 6/2011 | Kuramochi et al. |
| 2011/0229459 A1 | 9/2011 | Kuramochi et al. |
| 2011/0236374 A1 | 9/2011 | Shitara et al. |
| 2011/0245473 A1 | 10/2011 | Igawa et al. |
| 2012/0028304 A1 | 2/2012 | Dahiyat et al. |
| 2012/0065379 A1 | 3/2012 | Igawa et al. |
| 2012/0071634 A1 | 3/2012 | Igawa et al. |
| 2012/0121587 A1 | 5/2012 | Maeda et al. |
| 2012/0238729 A1 | 9/2012 | Kuramochi et al. |
| 2012/0253016 A1 | 10/2012 | Igawa et al. |
| 2013/0011866 A1 | 1/2013 | Igawa et al. |
| 2013/0018174 A1 | 1/2013 | Igawa et al. |
| 2013/0030156 A1 | 1/2013 | Apostolou et al. |
| 2013/0039913 A1 | 2/2013 | Labrijn et al. |
| 2013/0052196 A1 | 2/2013 | Apostolou et al. |
| 2013/0101581 A1 | 4/2013 | Kuramochi et al. |
| 2013/0195849 A1 | 8/2013 | Spreter et al. |
| 2013/0317203 A1 | 11/2013 | Igawa et al. |
| 2014/0039165 A1 | 2/2014 | Kuramochi et al. |
| 2014/0112883 A1 | 4/2014 | Ponath et al. |
| 2014/0303356 A1 | 10/2014 | Gramer et al. |
| 2014/0377253 A1 | 12/2014 | Harding et al. |
| 2015/0118184 A1 | 4/2015 | Kawai |
| 2015/0166666 A1 | 6/2015 | Igawa et al. |
| 2015/0175704 A1 | 6/2015 | Kuramochi et al. |
| 2015/0274809 A1 | 10/2015 | Igawa et al. |
| 2015/0284465 A1 | 10/2015 | Igawa et al. |
| 2015/0315278 A1 | 11/2015 | Igawa et al. |
| 2016/0229915 A1 | 8/2016 | Igawa et al. |
| 2017/0275332 A1 | 9/2017 | Igawa et al. |

FOREIGN PATENT DOCUMENTS

| | | |
|---|---|---|
| AU | 2008332271 | 6/2009 |
| AU | 2009290162 | 4/2010 |
| CA | 1 332 367 | 10/1994 |
| CA | 2 203 182 | 5/1996 |
| CA | 2 443 294 | 10/2002 |
| CA | 2 523 577 | 11/2004 |
| CA | 2 531 482 | 1/2005 |
| CA | 2 549 467 | 7/2005 |
| CA | 2 560 953 | 9/2005 |
| CA | 2 625 773 | 4/2007 |
| CA | 2 626 688 | 4/2007 |
| CA | 2 647 846 | 10/2007 |
| CA | 2 648 644 | 10/2007 |
| CA | 2 700 394 | 4/2009 |
| CA | 2 700 498 | 4/2009 |
| CA | 2 700 986 | 4/2009 |
| CA | 2 708 065 | 6/2009 |
| CA | 2 708 532 | 6/2009 |
| CN | 101198698 | 6/2008 |
| CN | 102471378 | 5/2012 |
| EA | 009026 | 10/2007 |
| EP | 0 361 902 | 4/1990 |
| EP | 0 637 593 | 2/1995 |
| EP | 0 783 893 | 7/1997 |
| EP | 0 811 691 | 12/1997 |
| EP | 1 069 185 | 1/2001 |
| EP | 1 188 830 | 3/2002 |
| EP | 1 382 969 | 1/2004 |
| EP | 1 510 943 | 3/2005 |
| EP | 1 701 979 | 9/2006 |
| EP | 1 728 801 | 12/2006 |
| EP | 1733740 | 12/2006 |
| EP | 1 773 391 | 4/2007 |
| EP | 1 847 602 | 10/2007 |
| EP | 1 870 458 | 12/2007 |
| EP | 1 870 459 | 12/2007 |
| EP | 1 900 814 | 3/2008 |
| EP | 2 006 381 | 12/2008 |
| EP | 2 009 101 | 12/2008 |

(56) References Cited

FOREIGN PATENT DOCUMENTS

| | | |
|---|---|---|
| EP | 2 031 064 | 3/2009 |
| EP | 2 047 863 | 4/2009 |
| EP | 2 107 115 | 10/2009 |
| EP | 2 194 066 | 6/2010 |
| EP | 2 196 541 | 6/2010 |
| EP | 2 202 245 | 6/2010 |
| EP | 2 206 775 | 7/2010 |
| EP | 2 228 392 | 9/2010 |
| EP | 2 236 604 | 10/2010 |
| EP | 2 241 332 | 10/2010 |
| EP | 2 275 443 | 1/2011 |
| EP | 2 330 193 | 8/2011 |
| EP | 2 354 161 | 8/2011 |
| EP | 2 409 991 | 1/2012 |
| EP | 2 522 724 | 11/2012 |
| EP | 2 543 727 | 1/2013 |
| EP | 2 644 698 | 10/2013 |
| EP | 2 905 290 | 8/2015 |
| EP | 2 914 634 | 9/2015 |
| JP | 2-028200 | 1/1990 |
| JP | 2-163096 | 6/1990 |
| JP | 07-67688 | 3/1995 |
| JP | 08-500979 | 2/1996 |
| JP | 09-506001 | 6/1997 |
| JP | 11-500915 | 1/1999 |
| JP | 11-500916 | 1/1999 |
| JP | 2002-514406 | 5/2002 |
| JP | 2004-86862 | 3/2004 |
| JP | 2004-511426 | 4/2004 |
| JP | 2005-532805 | 11/2005 |
| JP | 2005-535341 | 11/2005 |
| JP | 2005-537009 | 12/2005 |
| JP | 2008-512995 | 5/2008 |
| JP | 2008-538920 | 11/2008 |
| JP | 2009-500458 | 1/2009 |
| JP | 2010-522701 | 7/2010 |
| JP | 2011-508604 | 3/2011 |
| JP | 2012-510281 | 5/2012 |
| JP | 2012-522527 | 9/2012 |
| JP | 2012-531439 | 12/2012 |
| JP | 5144499 | 2/2013 |
| JP | 2013-515509 | 5/2013 |
| JP | 2013-529084 | 7/2013 |
| JP | 2013-529190 | 7/2013 |
| JP | 2013-165716 | 8/2013 |
| JP | 2013-541594 | 11/2013 |
| JP | 5334319 | 11/2013 |
| JP | 5484060 | 5/2014 |
| JP | 5717624 | 5/2015 |
| JP | 2015-130883 | 7/2015 |
| JP | 5787446 | 9/2015 |
| KR | 2006/0010765 | 2/2006 |
| KR | 2007/0035482 | 3/2007 |
| KR | 2010/0074221 | 7/2010 |
| KR | 2010/0097721 | 9/2010 |
| RU | 94028282 | 7/1996 |
| RU | 2195960 | 1/2003 |
| RU | 2232773 | 7/2004 |
| RU | 2266298 | 12/2005 |
| TW | 200810778 | 3/2008 |
| TW | 200932266 | 8/2009 |
| WO | WO 91/01335 | 2/1991 |
| WO | WO 92/19759 | 11/1992 |
| WO | WO 1994/005690 | 3/1994 |
| WO | WO 94/10354 | 5/1994 |
| WO | WO 94/12215 | 6/1994 |
| WO | WO 95/14710 | 6/1995 |
| WO | WO 95/33844 | 12/1995 |
| WO | WO 96/11020 | 4/1996 |
| WO | WO 96/12503 | 5/1996 |
| WO | WO 96/23071 | 8/1996 |
| WO | WO 96/27011 | 9/1996 |
| WO | WO 97/09351 | 3/1997 |
| WO | WO 97/10354 | 3/1997 |
| WO | WO 98/03546 | 1/1998 |
| WO | WO 98/50431 | 11/1998 |
| WO | WO 99/03495 | 1/1999 |
| WO | WO 99/18212 | 4/1999 |
| WO | WO 99/51743 | 10/1999 |
| WO | WO 99/58572 | 11/1999 |
| WO | WO 00/34317 | 6/2000 |
| WO | WO 00/75314 | 12/2000 |
| WO | WO 01/30854 | 5/2001 |
| WO | WO 01/82899 | 11/2001 |
| WO | WO 02/072605 | 9/2002 |
| WO | WO 03/000883 | 1/2003 |
| WO | WO 2003/020949 | 3/2003 |
| WO | WO 03/057881 | 7/2003 |
| WO | WO 03/060090 | 7/2003 |
| WO | WO 03/105757 | 12/2003 |
| WO | WO 2004/008147 | 1/2004 |
| WO | WO 2004/016740 | 2/2004 |
| WO | WO 2004/020579 | 3/2004 |
| WO | WO 2004/068931 | 8/2004 |
| WO | WO 2004/085476 | 10/2004 |
| WO | WO 2004/091543 | 10/2004 |
| WO | WO 2004/096273 | 11/2004 |
| WO | WO 2004/113387 | 12/2004 |
| WO | WO 2005/005604 | 1/2005 |
| WO | WO 2005/035753 | 4/2005 |
| WO | WO 2005/035754 | 4/2005 |
| WO | WO 2005/035756 | 4/2005 |
| WO | WO 2005/047327 | 5/2005 |
| WO | WO 2005/056606 | 6/2005 |
| WO | WO 2005/059106 | 6/2005 |
| WO | WO 2005/062916 | 7/2005 |
| WO | WO 2005/067620 | 7/2005 |
| WO | WO 2005/080429 | 9/2005 |
| WO | WO 2005/090405 | 9/2005 |
| WO | WO 2005/112564 | 12/2005 |
| WO | WO 2005/123126 | 12/2005 |
| WO | WO 2006/004663 | 1/2006 |
| WO | WO 2006/019447 | 2/2006 |
| WO | WO 2006/023144 | 3/2006 |
| WO | WO 2006/029879 | 3/2006 |
| WO | WO 2006/030200 | 3/2006 |
| WO | WO 2006/030220 | 3/2006 |
| WO | WO 2006/033386 | 3/2006 |
| WO | WO 2006/047350 | 5/2006 |
| WO | WO 2006/050491 | 5/2006 |
| WO | WO 2006/067913 | 6/2006 |
| WO | WO 2006/070286 | 7/2006 |
| WO | WO 2006/071877 | 7/2006 |
| WO | WO 2006/075668 | 7/2006 |
| WO | WO 2006/088855 | 8/2006 |
| WO | WO 2006/106903 | 10/2006 |
| WO | WO 2006/106905 | 10/2006 |
| WO | WO 2006/109592 | 10/2006 |
| WO | WO 2006/113767 | 10/2006 |
| WO | WO 2006/116260 | 11/2006 |
| WO | WO 2006/118959 | 11/2006 |
| WO | WO 2006/119062 | 11/2006 |
| WO | WO 2006/119115 | 11/2006 |
| WO | WO 2006/121852 | 11/2006 |
| WO | WO 2007/009065 | 1/2007 |
| WO | WO 2007/060411 | 5/2007 |
| WO | WO 2007/074880 | 7/2007 |
| WO | WO 2007/108559 | 9/2007 |
| WO | WO 2007/108756 | 9/2007 |
| WO | WO 2007/114319 | 10/2007 |
| WO | WO 2007/114325 | 10/2007 |
| WO | WO 2007/133816 | 11/2007 |
| WO | WO 2007/137984 | 12/2007 |
| WO | WO 2007/142325 | 12/2007 |
| WO | WO 2007/143168 | 12/2007 |
| WO | WO 2008/043822 | 4/2008 |
| WO | WO 2008/090960 | 7/2008 |
| WO | WO 2008/092117 | 7/2008 |
| WO | WO 2008/103432 | 8/2008 |
| WO | WO 2008/119353 | 10/2008 |
| WO | WO 2008/132453 | 11/2008 |
| WO | WO 2008/145141 | 12/2008 |
| WO | WO 2009/041062 | 4/2009 |
| WO | WO 2009/041613 | 4/2009 |

(56) References Cited

FOREIGN PATENT DOCUMENTS

| | | |
|---|---|---|
| WO | WO 2009/041621 | 4/2009 |
| WO | WO 2009/041643 | 4/2009 |
| WO | WO 2009/041734 | 4/2009 |
| WO | WO 2009/052439 | 4/2009 |
| WO | WO 2009/053368 | 4/2009 |
| WO | WO 2009/063965 | 5/2009 |
| WO | WO 2009/072598 | 6/2009 |
| WO | WO 2009/072604 | 6/2009 |
| WO | WO 2009/079649 | 6/2009 |
| WO | WO 2009/089004 | 7/2009 |
| WO | WO 2009/100309 | 8/2009 |
| WO | WO 2009/125825 | 10/2009 |
| WO | WO 2009/139822 | 11/2009 |
| WO | WO 2010/035769 | 4/2010 |
| WO | WO 2010/063746 | 6/2010 |
| WO | WO 2010/064090 | 6/2010 |
| WO | WO 2010/064456 | 6/2010 |
| WO | WO 2010/064697 | 6/2010 |
| WO | WO 2010/107109 | 9/2010 |
| WO | WO 2010/107110 | 9/2010 |
| WO | WO 2010/115589 | 10/2010 |
| WO | WO 2010/131733 | 11/2010 |
| WO | WO 2010/151792 | 12/2010 |
| WO | WO 2011/037158 | 3/2011 |
| WO | WO 2011/078332 | 6/2011 |
| WO | WO 2011/090754 | 7/2011 |
| WO | WO 2011/090762 | 7/2011 |
| WO | WO 2011/091177 | 7/2011 |
| WO | WO 2011/091181 | 7/2011 |
| WO | WO 2011/108502 | 9/2011 |
| WO | WO 2011/108714 | 9/2011 |
| WO | WO 2011/111007 | 9/2011 |
| WO | WO 2011/131746 | 10/2011 |
| WO | WO 2011/133886 | 10/2011 |
| WO | WO 2011/143545 | 11/2011 |
| WO | WO 2012/020096 | 2/2012 |
| WO | WO 2012/064627 | 5/2012 |
| WO | WO 2012/067176 | 5/2012 |
| WO | WO 2012/145238 | 10/2012 |
| WO | WO 2013/060867 | 5/2013 |
| WO | WO 2013/157954 | 10/2013 |
| WO | WO 2014/028354 | 2/2014 |
| WO | WO 2014/054804 | 4/2014 |
| WO | WO 2014/067011 | 5/2014 |
| WO | WO 2015/046467 | 4/2015 |
| WO | WO 2016/136933 | 9/2016 |
| WO | WO 2016/159213 | 10/2016 |

OTHER PUBLICATIONS

Labrijn et al., "Species-specific determinants in the IgG CH3 domain enable Fab-arm exchange by affecting the noncovalent CH3-CH3 interaction strength," *J Immunol.*, Sep. 15, 2011; 187(6):3238-46. doi: 10.4049/jimmunol.1003336. Epub Aug. 12, 2011.

McPhee et al., "Engineering human immunodeficiency virus 1 protease heterodimers as macromolecular inhibitors of viral maturation," *Proc Natl Acad Sci U S A.*, Oct. 15, 1996; 93(21):11477-81.

Rispens et al., "Dynamics of inter-heavy chain interactions in human immunoglobulin G (IgG) subclasses studied by kinetic Fab arm exchange," *J Biol Chem.*, Feb. 28, 2014; 289(9):6098-109. doi: 10.1074/jbc.M113.541813. Epub Jan. 14, 2014.

Schaefer et al., "Immunoglobulin domain crossover as a generic approach for the production of bispecific IgG antibodies," *Proc Natl Acad Sci U S A.*, Jul. 5, 2011; 108(27):11187-92. doi: 10.1073/pnas.1019002108. Epub Jun. 20, 2011.

Schuurman et al., "Normal human immunoglobulin G4 is bispecific: it has two different antigen-combining sites," *Immunology*, Aug. 1999; 97(4):693-8.

Schuurman et al., "The inter-heavy chain disulfide bonds of IgG4 are in equilibrium with intra-chain disulfide bonds," *Mol Immunol.*, Jan. 2001; 38(1):1-8.

Van Der Neut Kolfschoten et al., "Anti-inflammatory activity of human IgG4 antibodies by dynamic Fab arm exchange," *Science*, Sep. 14, 2007; 317(5844):1554-7.

Ward et al., "Effects of engineering complementary charged residues into the hydrophobic subunit interface of tyrosyl-tRNA synthetase. Appendix: Kinetic analysis of dimeric enzymes that reversibly dissociate into inactive subunits," *Biochemistry*, Jun. 30, 1987; 26(13):4131-8.

U.S. Appl. No. 15/263,617, filed Sep. 13, 2016, Igawa et al.

Berglund et al., "The epitope space of the human proteome," *Protein Sci.*, Apr. 2008;17(4):606-13.

Chen et al., "Selection and analysis of an optimized anti-VEGF antibody: crystal structure of an affinity-matured Fab in complex with antigen," *J Mol Biol.*, Nov. 5, 1999;293(4):865-81.

Holm et al., "Functional mapping and single chain construction of the anti-cytokeratin 8 monoclonal antibody TS1," *Mol Immunol.*, Feb. 2007;44(6):1075-84.

Examiner Michael D. Allen, USPTO Non-Final Office Action in U.S. Appl. No. 13/582,073, dated Aug. 19, 2016, 20 pages.

U.S. Appl. No. 15/263,617, Igawa et al., Sep. 13, 2016.

Brenner et al., "Errors in genome annotation," *Trends in Genetics*, Apr. 1999;15:132-133.

Choi et al., "Engineering of Immunoglobulin Fc Heterodimers Using Yeast Surface-Displayed Combinatorial Fc Library Screening," *PLoS One*, Dec. 16, 2015;10(12):e0145349. doi: 10.1371/journal.pone.0145349. eCollection 2015.

Coloma et al., "Position effects of variable region carbohydrate on the affinity and in vivo behavior of an anti-(1→6) dextran antibody," *J Immunol.*, Feb. 15, 1999;162(4):2162-70.

Diaz et al., "Effects of engineering charged amino acids in the CH3 domains on antibody heavy chain dimerization," Philippine Science Letters. 2011;4(1):48-55.

Ejima et al, "Effects of Acid Exposure on the Conformation, Stability, and Aggregation of Monoclonal Antibodies," Proteins. Mar. 1, 2007;66(4):954-62.

Gen Bank Accession No. AAG00910.2, "recombinant IgG2 heavy chain, partial [*Homo sapiens*]," May 14, 2001, 1 page.

Hird et al., "Tumour localisation with a radioactively labelled reshaped human monoclonal antibody," *Br J Cancer*, Nov. 1991;64(5):911-4.

Hong et al., "Enhanced cellular uptake and transport of polyclonal immunoglobulin G and fab after their cationization," *J Drug Target.*, 2000;8(2):67-77.

Li et al., "Construction and characterization of a humanized anti-human CD3 monoclonal antibody 12F6 with effective immunoregulation functions," *Immunology*, Dec. 2005;116(4):487-98.

Marshall et al., "Rational design and engineering of therapeutic proteins," *Drug Discov Today*, Mar. 1, 2003;8(5):212-21.

Newman et al, "Modification of the Fc Region of a Primatized IgG Antibody to Human CD4 Retains Its Ability to Modulate CD4 Receptors but Does Not Deplete CD4 T Cells in Chimpanzees," Clin Immunol. Feb. 2001;98(2):164-74.

Pardridge et al., "Enhanced cellular uptake and in vivo biodistribution of a monoclonal antibody following cationization," *J Pharm Sci.*, Aug. 1995;84(8):943-8.

Reimann et al., "A humanized form of a CD4-specific monoclonal antibody exhibits decreased antigenicity and prolonged plasma half-life in rhesus monkeys while retaining its unique biological and antiviral properties," *AIDS Res Hum Retroviruses*, Jul. 20, 1997;13(11):933-43.

Roopenian et al., "FcRn: the neonatal Fc receptor comes of age," *Nat Rev. Immunol.*, Sep. 2007;7(9):715-25.

Sarkar et al., "Rational cytokine design for increased lifetime and enhanced potency using pH-activated histidine switching", *Nat Biotechnol.*, Sep. 2002;20(9):908-13. Epub Aug. 5, 2002.

Sharifi et al., "Improving monoclonal antibody pharmacokinetics via chemical modification," Q *J Nucl Med.*, Dec. 1998;42(4):242-9.

Smith et al., "The challenges of genome sequence annotation or 'the devil is in the details'," *Nature Biotechnology*, Nov. 1997;15:1222-1223.

Tabrizi et al., "Elimination mechanisms of therapeutic monoclonal antibodies," *Drug Discov Today*, Jan. 2006;11(1-2):81-8.

Verhoeyen et al., "Construction of a reshaped HMFG1 antibody and comparison of its fine specificity with that of the parent mouse antibody," *Immunology*, Mar. 1993;78(3):364-70.

(56) References Cited

OTHER PUBLICATIONS

Verhoeyen et al., "Monoclonal Antibodies in Clinical Oncology," 1991, Edited by AA Epenetos, Chapter 5, pp. 37-43, Chapman and Hall.
Abe et al., "Purification of monoclonal antibodies with light-chain heterogeneity produced by mouse hybridomas raised with NS-1 myelomas: application of hydrophobic interaction high-performance liquid chromatography," J. Biochem. Biophys. Methods, 27:215-227 (1993).
Adams et al., "Humanization of a recombinant monoclonal antibody to produce a therapeutic HER dimerization inhibitor, pertuzumab," Cancer Immunol. Immunother., 55:717-727 (2006).
Algonomics—Tripole® applications [online] Retrieved from the Internet on Feb. 29, 2012: http://web.archive.org/web20090221052902/http://www.algonomics.com/proteinengineering/tripole_applications.php, 2 pages (Feb. 21, 2009).
Allard et al., "Antigen binding properties of highly purified bispecific antibodies," Mol Immunol., Oct. 1992; 29 (10):1219-27.
Allen et al., "Novel mechanism for gonadotropin-releasing hormone neuronal migration involving Gas6/Ark signaling to p38 mitogen-activated protein kinase," Mol. Cell. Biol., 22(2):599-613 (2002).
Allen et al., "Interchain disulfide bonding in human IgG2 antibodies probed by site-directed mutagenesis," Biochemistry, 48(17):3755-66 (2009).
Almagro et al., "Humanization of antibodies," Front Biosci., 13:1619-33 (2008).
Amersham Biosciences, "Affinity Chromatography: Principles and Methods," Edition AD, pp. 16-18, 137 (2002).
Amersham Biosciences, "Protein Purification Handbook," Edition AC, 98 pages (2001).
Armour et al., "Recombinant human IgG molecules lacking Fcgamma receptor I binding and monocyte triggering activities," Eur. J. Immunol., 29(8):2613-24 (1999).
Aslan et al., "Engineering a novel, stable dimeric streptavidin with lower isoelectric point," J. Biotechnol., 128(2):213-25 (2007).
Atwell et al., "Stable heterodimers from remodeling the domain interface of a homodimer using a phage display library," J. Mol. Biol., 270:26-35 (1997).
Baerga-Ortiz et al., "Two different proteins that compete for binding to thrombin have opposite kinetic and thermodynamic profiles," Protein Sci., 13(1):166-76 (2004).
Baker et al., "Conversion of a T cell antagonist into an agonist by repairing a defect in the TCR/peptide/MHC interface: implications for TCR signaling," Immunity, 13:475-484 (2000).
Bartelds et al., "Clinical response to adalimumab: relationship to anti-adalimumab antibodies and serum adalimumab concentrations in rheumatoid arthritis," Ann Rheum. Dis., 66(7):921-6 (2007).
Bayry et al., "Immuno affinity purification of foot and mouth disease virus type specific antibodies using recombinant protein adsorbed to polystyrene wells," J. Virol. Methods, 81:21-30 (1999).
Bellosta et al., "Signaling through the ARK tyrosine kinase receptor protects from apoptosis in the absence of growth stimulation," Oncogene., 15(20):2387-97 (1997).
Bender et al., "Immunogenicity, efficacy and adverse events of adalimumab in RA patients," Rheumatol. Int., 27(3):269-74 (2007).
Bendig, "Humanization of rodent monoclonal antibodies by CDR grafting," Methods: A Comparison to Methods in Enzymology, 8:83-93 (1995).
Bian et al., "Discovery of promiscuous HLA-II-restricted T cell epitopes with Tepitope," Methods, 34(4):468-75 (2004).
Bilsborough, "IL-31 is associated with cutaneous lymphocyte antigen-positive skin homing T cells in patients with atopic dermatitis," J. Allergy Clin. Immunol., 117(2):418-25 (2006).
Binz et al., "Engineering novel binding proteins from nonimmunoglobulin domains," Nat. Biotechnol., 23:1257-68 (2005).
Bowie et al., "Deciphering the message in protein sequences: tolerance to amino acid substitutions," Science, 247:1306-1310 (1990).
Branden and Tooze, "Recognition of Foreign Molecules by the Immune System," Introduction to Protein Structure, 2d Ed., Garland Publishing, pp. 299-323 (1999).
Brown et al., "Tolerance of single, but not multiple, amino acid replacements in antibody $V_H$ CDR 2: a means of minimizing B cell wastage from somatic hypermutation?," J. Immunol., 156(9):3285-91 (1996).
Budagian et al., "A promiscuous liaison between IL-15 receptor and Axl receptor tyrosine kinase in cell death control," EMBO J., 24(24):4260-70 (2005).
Burges et al., "Effective relief of malignant ascites in patients with advanced ovarian cancer by a trifunctional anti-EpCAM x anti-CD3 antibody: a phase I/II study," Clin. Cancer Res., 13(13):3899-905 (2007).
Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell. Biol., 111:2129-2138 (1990).
Calbiochem® Buffers, "A guide for the preparation and use of buffers in biological systems," by Chandra Mohan, Ph.D., Copyright© 2003 EMD Biosciences, Inc., an Affiliate of Merck KGaA, Darmstadt, Germany, 37 pages.
Carter, "Bispecific human IgG by design," J. Immunol. Methods, 248:7-15 (2001).
Casset et al., "A peptide mimetic of an anti-CD4 monoclonal antibody by rational design," Biochem Biophys Res Commun., Jul. 18, 2003;307:198-205.
Chamow et al., "A humanized, bispecific immunoadhesin-antibody that retargets CD3+ effectors to kill HIV-1-infected cells," J. Immunol., 153(9):4268-80 (1994).
Chappel et al., "Identification of a secondary Fc gamma RI binding site within a genetically engineered human IgG antibody," J Biol Chem., Nov. 25, 1993;268(33):25124-31.
Chappel et al., "Identification of the Fc gamma receptor class I binding site in human IgG through the use of recombinant IgG1/IgG2 hybrid and point-mutated antibodies," Proc Natl Acad Sci U S A., Oct. 15, 1991;88(20):9036-40.
Chau et al., "HuM291(Nuvion), a humanized Fc receptor-nonbinding antibody against CD3, anergizes peripheral blood T cells as partial agonist of the T cell receptor," Transplantation, 71(7):941-50 (2001).
Chen et al., "Generation and analysis of random point mutations in an antibody CDR2 sequence: many mutated antibodies lose their ability to bind antigen," J. Exp. Med., 176(3):855-66 (1992).
Chen et al., "Defective secretion of an immunoglobulin caused by mutations in the heavy chain complementarity determining region 2," J. Exp. Med., 180(2):577-86 (1994).
Chien et al., "Significant structural and functional change of an antigen-binding site by a distant amino acid substitution: proposal of a structural mechanism," Proc. Natl. Acad. Sci. U.S.A., 86(14):5532-6 (1989).
Chirino et al., "Minimizing the immunogenicity of protein therapeutics," Drug Discov. Today., 9(2):82-90 (2004).
Chu et al., "Accumulation of succinimide in a recombinant monoclonal antibody in mildly acidic buffers under elevated temperatures," Pharm. Res., 24(6):1145-56 (2007).
Chung et al., "Expression of the proto-oncogene Axl in renal cell carcinoma," DNA Cell Biol., 22(8):533-40 (2003).
Cole et al., "Human IgG2 variants of chimeric anti-CD3 are nonmitogenic to T cells," J. Immunol., 159(7):3613-21 (1997).
Comper and Glasgow, "Charge selectivity in kidney ultrafiltration," Kidney Int., 47:1242-51 (1995).
Cordoba et al., "Non-enzymatic hinge region fragmentation of antibodies in solution," J. Chromatogr. B. Analyt. Technol. Biomed. Life Sci., 818(2):115-21 (2005).
Couto et al., "Anti-BA46 Monoclonal Antibody Mc3: Humanization Using a Novel Positional Consensus and in Vivo and in Vitro Characterization," Cancer Research, 55:1717-1722 (1995).
Craven et al., "Receptor tyrosine kinases expressed in metastatic colon cancer," Int. J. Cancer, 60(6):791-7 (1995).
Dall'Acqua et al., "Antibody humanization by framework shuffling," Methods, 36(1):43-60 (2005).

(56) References Cited

OTHER PUBLICATIONS

Dall'Acqua et al., "Modulation of the effector functions of a human IgG1 through engineering of its hinge region," J. Immunol., 177(2):1129-38 (2006).
Damschroder et al., "Framework shuffling of antibodies to reduce immunogenicity and manipulate functional and biophysical properties," Mol. Immunol., 44(11):3049-60 (2007).
Datta-Mannan et al., "Monoclonal antibody clearance. Impact of modulating the interaction of IgG with the neonatal Fc receptor," J Biol Chem., 282(3):1709-17 (2007).
Davies et al., "Affinity improvement of single antibody VH domains: residues in all three hypervariable regions affect antigen binding," Immunotechnology, 2(3):169-79 (1996).
De Pascalis et al., "Grafting of "abbreviated" complementarity-determining regions containing specificity-determining residues essential for ligand contact to engineer a less immunogenic humanized monoclonal antibody," J. Immunol., 169(6):3076-84 (2002).
Deen et al., "Structural determinants of glomerular permeability," Am. J. Physiol. Renal. Physiol., 281:F579-F596 (2001).
De Groot et al., "De-immunization of therapeutic proteins by T-cell epitope modification," Dev. Biol. (Basel), 122:171-94 (2005).
Del Rio et al., "An Engineered Penicillin Acylase with Altered Surface Charge Is More Stable in Alkaline pH," Ann. NY Acad. Sci., 799:61-64 (1996).
Deng et al., "An Agonist Murine Monoclonal Antibody to the Human c-Mpl Receptor Stimulates Megakaryocytopoiesis," Blood, 92:1981-88 (1998).
Dhiman et al., "Gene expression microarrays: a 21st century tool for directed vaccine design," Vaccine, 20(1-2):22-30 (2001).
Dillon et al., "Structural and functional characterization of disulfide isoforms of the human IgG2 subclass," J. Biol. Chem., 283(23):16206-15 (2008).
Dillon et al., "Interleukin 31, a cytokine produced by activated T cells, induces dermatitis in mice," Nat. Immunol., 5(7):752-760 (2004).
Diveu et al., "GPL, a novel cytokine receptor related to GP130 and leukemia inhibitory factor receptor," J. Biol. Chem., 278(50):49850-49859 (2003).
Dumont et al., "Monomeric Fc fusions: impact on pharmacokinetic and biological activity of protein therapeutics," BioDrugs., 20(3):151-60 (2006).
Elliott et al., "Activation of the erythropoietin (EPO) receptor by bivalent anti-EPO receptor antibodies," J. Biol. Chem., 271(40):24691-7 (1996).
Ewert et al., "Stability improvement of antibodies for extracellular and intracellular applications: CDR grafting to stable frameworks and structure-based framework engineering," Methods, 34:184-199 (2004).
Fridell et al., "GAS6 induces Axl-mediated chemotaxis of vascular smooth muscle cells," J. Biol. Chem., 273(12):7123-6 (1998).
Fujii, "Antibody affinity maturation by random mutagenesis," Methods Mol. Biol., 248:345-59 (2004).
Gerstner et al., "Sequence plasticity in the antigen-binding site of a therapeutic anti-HER2 antibody," J. Mol. Biol., 321(5):851-62 (2002).
Gessner et al., "The IgG Fc receptor family," Ann Hematol., 76(6):231-48 (1998).
Ghetie and Ward, "FcRn: the MHC class I-related receptor that is more than an IgG transporter," Immunol. Today, 18:592-598 (1997).
Ghetie et al., "Increasing the serum persistence of an IgG fragment by random mutagenesis," Nat. Biotechnol., 15:637-640 (1997).
Ghetie et al., "Multiple roles for the major histocompatibility complex class I- related receptor FcRn," Annu. Rev. Immunol., 18:739-766 (2000).
Gobburu et al., "Pharmacokinetics/dynamics of 5c8, a monoclonal antibody to CD154 (CD40 ligand) suppression of an immune response in monkeys," J. Pharmacol. Exp. Ther., 286:925-930 (1998).

Goode et al., "The glomerular basement membrane charge-selectivity barrier: an oversimplified concept?," Nephrol. Dial. Transplant., 11:1714-16 (1996).
Goruppi et al., "Requirement of phosphatidylinositol 3-kinase-dependent pathway and Src for Gas6-Axl mitogenic and survival activities in NIH 3T3 fibroblasts," Mol. Cell Biol., 17(8):4442-53 (1997).
Graves et al., "Molecular modeling and preclinical evaluation of the humanized NR-LU-13 antibody," Clin. Cancer Res., 5:899-908 (1999).
Greenwood et al., "Structural motifs involved in human IgG antibody effector functions," Eur J Immunol., May 1993;23(5):1098-104.
Griffin et al., "Analysis of heavy and light chain sequences of conventional camelid antibodies from Camelus dromedarius and Camelus bactrianus species," J Immunol Methods, Mar. 2014;405:35-46. doi: 10.1016/j.jim.2014.01.003. Epub Jan. 18, 2014.
Gunasekaran et al., "Enhancing antibody Fc heterodimer formation through electrostatic steering effects: applications to bispecific molecules and monovalent IgG," J. Biol. Chem., 285(25):19637-46 (2010).
Gupta et al., "Affinity chromatography and co-chromatography of bispecific monoclonal antibody immunoconjugates," J. Biochem. Biophys. Methods, 51:203-216 (2002).
Gussow et al., "Humanization of monoclonal antibodies," Methods Enzymol., 203:99-121 (1991).
Guyre et al., "Increased potency of Fc-receptor-targeted antigens," Cancer Immunol. Immunother., 45(3-4):146-8 (1997).
Haagen et al., "Unprimed CD4+ and CD8+ T cells can be rapidly activated by a CD3 x CD19 bispecific antibody to proliferate and become cytotoxic," Cancer Immunol Immunother., Dec. 1994;39(6):391-6.
Hafizi et al., "Interaction of Axl receptor tyrosine kinase with C1-TEN, a novel C1 domain-containing protein with homology to tensin," Biochem. Biophys. Res. Commun., 299(5):793-800 (2002).
Hafizi et al., "Signalling and functional diversity within the Axl subfamily of receptor tyrosine kinases," Cytokine Growth Factor Rev., 17(4):295-304 (2006).
Hamers-Casterman et al., "Naturally occurring antibodies devoid of light chains," Nature, Jun. 3, 1993;363(6428):446-8.
Hanes et al., "Picomolar affinity antibodies from a fully synthetic naive library selected and evolved by ribosome display," Nat. Biotechnol., 18(12):1287-1292 (2000).
Hanson et al., "Catalytic antibodies and their applications," Curr. Opin. Biotechnol., 16:631-636 (2005).
He et al., "Humanization and pharmacokinetics of a monoclonal antibody with specificity for both E- and P-selectin," J. Immunol., 160:1029-35 (1998).
Hinton et al., "An engineered human IgG1 antibody with longer serum half-life," J. Immunol., Jan. 1, 2006;176:346-56.
Hinton et al., "Engineered human IgG antibodies with longer serum half-lives in primates," J. Biol. Chem., 279(8):6213-6 (2004).
Holland et al., "Multiple roles for the receptor tyrosine kinase axl in tumor formation," Cancer Res., Oct. 15, 2005;65(20):9294-303.
Holt et al., "Domain antibodies: proteins for therapy," Trends Biotechnol., 21(11):484-90 (2003).
Hombach et al., "A CD16/CD30 bispecific monoclonal antibody induces lysis of Hodgkin's cells by unstimulated natural killer cells in vitro and in vivo," Int J Cancer, 55:830-6 (1993).
Hwang et al., "Use of human germline genes in a CDR homology-based approach to antibody humanization," Methods., 36(1):35-42 (2005).
Igawa et al., "VH/VL interface engineering to promote selective expression and inhibit conformational isomerization of thrombopoietin receptor agonist single-chain diabody," Protein Eng Des Sel., Aug. 2010;23(8):667-77. doi: 10.1093/protein/gzq034. Epub Jun. 24, 2010.
Igawa et al., "Engineering the variable region of therapeutic IgG antibodies," MAbs, 3(3):243-52 (2011).
Igawa et al., "Reduced elimination of IgG antibodies by engineering the variable region," Protein Eng. Des. Sel., 23(5):385-92 (2010).

(56) References Cited

OTHER PUBLICATIONS

Igawa et al., "Antibody recycling by engineered pH-dependent antigen binding improves the duration of antigen neutralization," Nat. Biotechnol., 28(11):1203-7 (2010).
IMGT Scientific charts depicting the correspondence between Eu and Kabat numberings for the human IgG constant region, created May 17, 2001 and last updated Aug. 13, 2014.
Ito et al., "The His-probe method: effects of histidine residues introduced into the complementarity-determining regions of antibodies on antigen-antibody interactions at different pH values," FEBS Lett., 309:85-88 (1992).
Ito et al., "Expression of receptor-type tyrosine kinase, Axl, and its ligand, Gas6, in pediatric thyroid carcinomas around Chernobyl," Thyroid., 12(11):971-5 (2002).
Jackman et al., "Development of a two-part strategy to identify a therapeutic human bispecific antibody that inhibits IgE receptor signaling," J Biol Chem., Jul. 2, 2010;285(27): 20850-9. doi: 10.1074/jbc.M110.113910. Epub May 5, 2010.
Jain et al., "Engineering antibodies for clinical applications," Trends Biotechnol., 25(7):307-16 (2007).
Jefferis et al., "Recognition sites on human IgG for Fc gamma receptors: the role of glycosylation," Immunol. Lett., 44(2-3):111-7 (1995).
Jendeberg et al., "Engineering of Fc(1) and Fc(3) from human immunoglobulin G to analyse subclass specificity for staphylococcal protein A," J. Immunol. Methods., 201(1):25-34 (1997).
Johnson et al., "Cation exchange-HPLC and mass spectrometry reveal C-terminal amidation of an IgG1 heavy chain," Anal. Biochem., 360(1):75-83 (2007).
Jones et al., "Identification and removal of a promiscuous CD4+ T cell epitope from the C1 domain of factor VIII," Thromb. Haemost., 3(5):991-1000 (2005).
Ju et al., "Conversion of the interleukin 1 receptor antagonist into an agonist by site-specific mutagenesis," Proc. Natl. Acad. Sci. U.S.A., 88:2658-2662 (1991).
Kabat et al., Sequence of Proteins of Immunological Interest, $5^{th}$ Edition 1991, p. 690 and p. 693.
Kai et al., "Switching constant domains enhances agonist activities of antibodies to a thrombopoietin receptor," Nat. Biotechnol., 26(2):209-11 (2008).
Kashmiri et al., "Generation, characterization, and in vivo studies of humanized anticarcinoma antibody CC49," Hybridoma, 14:461-473 (1995).
Katayose et al., "MUC1-specific targeting immunotherapy with bispecific antibodies: inhibition of xenografted human bile duct carcinoma growth," Cancer Res., 56(18):4205-12 (1996).
Kenanova et al., "Tailoring the pharmacokinetics and positron emission tomography imaging properties of anti-carcinoembryonic antigen single-chain Fv-Fc antibody fragments," Cancer Res., Jan. 15, 2005;65(2):622-31.
Khawli et al., "Improved tumor localization and radioimaging with chemically modified monoclonal antibodies," Cancer Biother. Radiopharm., 11:203-215 (1996).
Kim et al., "Antibody Engineering for the Development of Therapeutic Antibodies," Mol. Cells, 20:17-29 (2005).
Kim et al., "Chemical modification to reduce renal uptake of disulfide-bonded variable region fragment of anti-tac monoclonal antibody labeled with 99mTc," Bioconjugate Chem., 10:447-453 (1999).
Kim et al., "Lowering of pI by acylation improves the renal uptake of 99mTc-labeled anti-Tac dsFv: effect of different acylating reagents," Nucl. Med. Biol., 29:795-801 (2002).
Kim et al., "Mapping the site on human IgG for binding of the MHC class I-related receptor, FcRn," Eur. J. Immunol., Sep. 1999;29(9):2819-25.
Kobayashi et al., "A monoclonal antibody specific for a distinct region of hen egg-white lysozyme," Mol. Immunol., 19:619-30 (1982).
Kobayashi et al., "The pharmacokinetic characteristics of glycolated humanized anti-Tac Fabs are determined by their isoelectric points," Cancer Res., 59:422-430 (1999).
Komissarov et al., "Site-specific mutagenesis of a recombinant anti-single-stranded DNA Fab. Role of heavy chain complementarity-determining region 3 residues in antigen interaction," J. Biol. Chem., 272(43):26864-70 (1997).
Kranenborg et al., "Development and characterization of anti-renal cell carcinoma x antichelate bispecific monoclonal antibodies for two-phase targeting of renal cell carcinoma," Cancer Res., 55:5864s-5867s (1995).
Krauss et al., "Impact of antibody framework residue VH-71 on the stability of a humanised anti-MUC1 scFv and derived immunoenzyme," Br. J. Cancer, 90:1863-70 (2004).
Kufer et al., "A revival of bispecific antibodies," Trends Biotechnol., 22(5):238-44 (2004).
Kurfis et al., "Role of Arg182 in the second extracellular loop of angiotensin II receptor AT2 in ligand binding," Biochem. Biophys. Res. Commun., 263:816-819 (1999).
Kreutz et al., "Efficient bispecific monoclonal antibody purification using gradient thiophilic affinity chromatography," J. Chromatogr. B, 714:161-170 (1998).
Lansdorp et al., "Purification and analysis of bispecific tetrameric antibody complexes," Mol. Immunol., 27:659-666 (1990).
Lay et al., "Sulfasalazine suppresses drug resistance and invasiveness of lung adenocarcinoma cells expressing AXL," Cancer Res., 67(8):3878-87 (2007).
Lazar et al., "Transforming growth factor alpha: mutation of aspartic acid 47 and leucine 48 results in different biological activities," Mol. Cell. Biol., 8:1247-1252 (1988).
Lebégue et al., "Production and characterization of hybrid monoclonal antibodies with IgG1/IgG3 double isotype," C R Acad Sci III., 1990;310(9):377-82.
Leong et al., "Adapting pharmacokinetic properties of a humanized anti-interleukin-8 antibody for therapeutic applications using site-specific pegylation," Cytokine, 16(3):106-19 (2001).
Levin et al., "Optimizing the affinity and specificity of proteins with molecular display," Mol. Biosyst., 2(1):49-57 (2006) (Epub Nov. 8, 2005).
Lin et al., "Preclinical pharmacokinetics, interspecies scaling, and tissue distribution of a humanized monoclonal antibody against vascular endothelial growth factor," J Pharmacol Exp Ther., 288(1):371-8 (1999).
Lindhofer et al., "Preferential Species-Restricted Heavy/Light Chain Pairing in Rat/Mouse Quadromas," J. Immunol., 155:219-225 (1995).
Liu et al., "Heterogeneity of monoclonal antibodies," J. Pharm. Sci., 97(7):2426-47 (2008).
Lloyd et al., "The production of a bispecific anti-CEA, anti-hapten (4-amino-phthalate) hybrid-hybridoma," J Natl Med Assoc., Oct. 1991;83(10):901-4.
Lobo et al., "Antibody pharmacokinetics and pharmacodynamics," J. Pharm. Sci., 93:2645-68 (2004).
Lund et al., "Expression and characterization of truncated forms of humanized L243 IgG1. Architectural features can influence synthesis of its oligosaccharide chains and affect superoxide production triggered through human Fcgamma receptor I," Eur. J. Biochem., 267(24):7246-57 (2000).
MacCallum et al., "Antibody-antigen interactions: contact analysis and binding site topography," J. Mol. Biol., 262:732-45 (1996).
Maeda et al., "pH-dependent receptor/ligand dissociation as a determining factor for intracellular sorting of ligands for epidermal growth factor receptors in rat hepatocytes," J. Control Release, 82(1):71-82 (2002).
Maini et al., "Double-blind randomized controlled clinical trial of the interleukin-6 receptor antagonist, tocilizumab, in European patients with rheumatoid arthritis who had an incomplete response to methotrexate," Arthritis Rheum., 54(9):2817-29 (2006).
Male et al., "Antibodies" Immunology, 7th Edition (2006), published by Elsevier Ltd., pp. 59-86.
Manz et al., Bioanalytical Chemistry, World Scientific Publishing Co. (2003).

(56) References Cited

OTHER PUBLICATIONS

Manzke et al., "Single-step purification of bispecific monoclonal antibodies for immunotherapeutic use by hydrophobic interaction chromatography," J. Immunol. Methods, 1997;208:65-73.
Mariuzza et al., "The structural basis of antigen-antibody recognition," Annu. Rev. Biophys. Chem., 16:139-59 (1987).
Marks et al., "By-passing immunization: building high affinity human antibodies by chain shuffling," Biotechnology (N.Y.), 10(7):779-83 (1992).
Marti et al., "Inverse electrostatic effect: electrostatic repulsion in the unfolded state stabilizes a leucine zipper," Biochemistry, 43(39):12436-47 (2004).
Martin et al., "Crystal structure at 2.8 A of an FcRn/heterodimeric Fc complex: mechanism of pH-dependent binding," Mol. Cell, 7:867-877 (2001).
Martinez et al., "Disulfide connectivity of human immunoglobulin G2 structural isoforms," Jul. 15, 2008;47(28):7496-508. doi: 10.1021/bi800576c. Epub Jun. 13, 2008.
Marvin et al., "Recombinant approaches to IgG-like bispecific antibodies," Acta. Pharmacol. Sin., 26:649-658 (2005).
Marvin et al., "Redesigning an antibody fragment for faster association with its antigen," Biochemistry, 42:7077-83 (2003).
Maxfield et al., "Endocytic recycling," Nat. Rev. Mol. Cell Biol., 5(2):121-32 (2004).
Maynard et al., "Antibody engineering," Annu. Rev. Biomed. Eng., 2:339-76 (2000).
McCloskey et al., "GAS6 mediates adhesion of cells expressing the receptor tyrosine kinase Axl," J. Biol. Chem., 272(37):23285-91 (1997).
Medesan et al., "Delineation of the amino acid residues involved in transcytosis and catabolism of mouse IgG1," J Immunol., Mar. 1, 1997;158(5):2211-7.
Merchant et al., "An efficient route to human bispecific IgG," Nat. Biotechnol., 16:677-681 (1998).
Meric et al., "Expression profile of tyrosine kinases in breast cancer," Clin. Cancer Res., 8(2):361-7 (2002).
Michaelsen et al., "A mutant human IgG molecule with only one C1q binding site can activate complement and induce lysis of target cells," Eur J Immunol., Jan. 2006;36(1):129-38.
Mihara et al., "Tocilizumab inhibits signal transduction mediated by both mIL-6R and sIL-6R, but not by the receptors of other members of IL-6 cytokine family," Int. Immunopharmacol., 5(12):1731-40 (2005).
Morell et al., "Metabolic properties of IgG subclasses in man," J. Clin. Invest., 49(4):673-80 (1970).
Morimoto et al., "Single-step purification of F(ab')2 fragments of mouse monoclonal antibodies (immunoglobulins G1) by hydrophobic interaction high performance liquid chromatography using TSKgel Phenyl-5PW," J. Biochem. Biophys. Methods, 24:107-117 (1992).
Murtaugh et al., "A combinatorial histidine scanning library approach to engineer highly pH-dependent protein switches," Protein Sci., 20(9):1619-31 doi:10.1002/pro 696 (2011).
Nakano et al., "Vascular smooth muscle cell-derived, Gla-containing growth-potentiating factor for Ca(2+)-mobilizing growth factors," J. Biol. Chem., 270(11):5702-5 (1995).
Nakano et al., "Prevention of growth arrest-induced cell death of vascular smooth muscle cells by a product of growth arrest-specific gene, gas6," FEBS Lett., 387(1):78-80 (1996).
Neis et al., "Enhanced expression levels of IL-31 correlate with IL-4 and IL-13 in atopic and allergic contact dermatitis," J. Allergy Clin. Immunol., 118(4):930-937 (2006).
Nemoto et al., "Overexpression of protein tyrosine kinases in human esophageal cancer," Pathobiology., 65(4):195-203 (1997).
Nesterova et al., "Glypican-3 as a novel target for an antibody-drug conjugate," AACR Abstract No. 656, Los Angeles, CA (Apr. 4-18, 2007).
Neubauer et al., "Expression of axl, a transforming receptor tyrosine kinase, in normal and malignant hematopoiesis," Blood, 84(6):1931-41 (1994).

Nishimoto et al., "Interleukin 6: from bench to bedside," Nat. Clin. Pract. Rheumatol., 2(11):619-26 (2006).
O'Bryan et al., "axl, a transforming gene isolated from primary human myeloid leukemia cells, encodes a novel receptor tyrosine kinase," Mol. Cell Biol., 11(10):5016-31 (1991).
O'Shea et al., "Peptide 'Velcro': design of a heterodimeric coiled coil," Curr Biol., Oct. 1, 1993;3(10):658-67.
Ohno et al., "Antigen-binding specificities of antibodies are primarily determined by seven residues of VH," Proc. Natl. Acad. Sci. U.S.A., 82(9):2945-9 (1985).
Ohsugi et al., Pharm Stage, 7(5):13-18 (2007).
Onda et al., "Lowering the Isoelectric Point of the Fv Portion of Recombinant Immunotoxins Leads to Decreased Nonspecific Animal Toxicity without Affecting Antitumor Activity," Cancer Res., 61:5070-77 (2001).
Ono et al., "The humanized anti-HM1.24 antibody effectively kills multiple myeloma cells by human effector cell-mediated cytotoxicity," Mol. Immunol., 36(6):387-95 (1999).
Ozhegov et al., Tolkovyi Slovar Russkogo iazyka: 2004, p. 292.
Padlan et al., "Identification of specificity-determining residues in antibodies," FASEB J., 9:133-139 (1995).
Padlan et al., "Structure of an antibody-antigen complex: crystal structure of the HyHEL-10 Fab-lysozyme complex," Proc. Natl. Acad. Sci. USA, 86:5938-5942 (1989).
Pakula et al., "Genetic Analysis of Protein Stability and Function," Annu. Rev. Genet., 23:289-310 (1989).
Pan et al., "Blocking neuropilin-1 function has an additive effect with anti-VEGF to inhibit tumor growth," Cancer Cell, Jan. 2007;11(1):53-67.
Pardridge et al., "Enhanced endocytosis in cultured human breast carcinoma cells and in vivo biodistribution in rats of a humanized monoclonal antibody after cationization of the protein," J. Pharmacol. Exp. Ther., 286(1):548-54 (1998).
Paul, "Structure and function of immunoglobulins," Fundamental Immunology, Third Edition, 292-295 (1993).
Pavlaki et al., "Matrix metalloproteinase inhibitors (MMPIs): the beginning of phase I or the termination of phase III clinical trials," Cancer Metastasis Rev., 22(2-3):177-203 (2003).
Pavlinkova et al., "Charge-modified single chain antibody constructs of monoclonal antibody CC49: Generation, characterization, pharmacokinetics, and biodistribution analysis," Nucl. Med. Biol., 26:27-34 (1999).
Pavlou et al., "The therapeutic antibodies market to 2008," Eur. J. Pharm. Biopharm., 59:389-396 (2005).
Pini et al., "Design and use of a phage display library. Human antibodies with subnanomolar affinity against a marker of angiogenesis eluted from a two-dimensional gel," J. Biol. Chem., 273(34):21769-76 (1998).
Poduslo et al., "Polyamine modification increases the permeability of proteins at the blood-nerve and blood-brain barriers," J. Neurochem., 66:1599-1609 (1996).
Pons et al., "Energetic analysis of an antigen/antibody interface: alanine scanning mutagenesis and double mutant cycles on the HyHEL-10/lysozyme interaction," Protein Sci., 8(5):958-68 (1999).
Presta, "Engineering of therapeutic antibodies to minimize immunogenicity and optimize function," Adv. Drug Deliv. Rev., 58(5-6):640-56 (2006).
Presta et al., "Molecular engineering and design of therapeutic antibodies," Curr. Opin. Immunol., 20(4):460-70. doi: 10.1016/j.coi.2008.06.012 (2008).
Queen et al., "A humanized antibody that binds to the interleukin 2 receptor," Proc. Natl. Acad. Sci. U.S.A., 86(24):10029-10033 (1989).
R&D Systems (R&D Systems, Anti-human IL-31 RA Antibody, Catalog #AF2769, Oct. 2008).
R&D Systems (R&D Systems, Biotinylated Anti-human IL-31 RA Antibody, Catalog #BAF2769, Nov. 2005), 1 page.
Raap et al., "Correlation of IL-31 serum levels with severity of atopic dermatitis," J. Allergy Clin. Immunol., 122(2):421-423 (2008).
Raffen et al., "Reengineering immunoglobulin domain interactions by introduction of charged residues," Protein Eng., Apr. 1998;11:303-9.

(56) References Cited

OTHER PUBLICATIONS

Rajpal et al., A general method for greatly improving the affinity of antibodies by using combinatorial libraries, Proc. Natl. Acad. Sci. USA, 102:8466-71 (2005).
Rathanaswami et al., "Demonstration of an in vivo generated sub-picomolar affinity fully human monoclonal antibody to interleukin-8," Biochem. Biophys. Res. Commun., 334:1004-13 (2005).
Reddy et al., "Elimination of Fc receptor-dependent effector functions of a modified IgG4 monoclonal antibody to human CD4," J. Immunol., 164(4):1925-33 (2000).
Reichert et al., "Monoclonal antibody successes in the clinic," Nat. Biotechnol., 23:1073-78 (2005).
Reichert et al., "Development trends for monoclonal antibody cancer therapeutics," Nat. Rev. Drug Discov., 6(5):349-56 (2007).
Reist et al., "Human IgG2 constant region enhances in vivo stability of anti-tenascin antibody 81C6 compared with its murine parent," Clin Cancer Res., Oct. 1998;4(10):2495-502.
Ridgway et al., "'Knobs-into-holes' engineering of antibody $C_H3$ domains for heavy chain heterodimerization," Protein Eng., 9:617-621 (1996).
Roguska et al., "Humanization of murine monoclonal antibodies through variable domain resurfacing," Proc Natl Acad Sci U.S.A., 91:969-73 (1994).
Roitt et al., Immunology, M., Mir, 5th Edition (2000), pp. 97-113.
Roitt et al., Immunology, M., Mir, (2000), pp. 110, 150, and 537-9 (in Russian, with what is believed to be a published English equivalent of those pages).
Roitt et al., Immunology, M., Mir, (2000), pp. 110-111 (in Russian, with what is believed to be a published English equivalent of those pages taken from Roitt et al., "Antibody Structure and Function," Immunology, Fifth Ed., (1998), pp. 80-81).
Rothe et al., "Ribosome display for improved biotherapeutic molecules," Expert Opin. Biol. Ther., 6(2):177-87 (2006).
Rudikoff et al., "Single amino acid substitution altering antigen-binding specificity," Proc. Natl. Acad. Sci. U.S.A., 79(6):1979-83 (1982).
Ruf et al., "Pharmacokinetics and in vivo stability of intraperitoneally administered therapeutic antibody catuniaxomab," J. Clin. Oncol., 26 (May 20 suppl) (2008), abstr 14006.
Sainaghi et al., "Gas6 induces proliferation in prostate carcinoma cell lines expressing the Axl receptor," J. Cell. Physiol., 204(1):36-44 (2005).
Salfeld et al., "Isotype selection in antibody engineering," Nat. Biotechnol., 25(12):1369-72 (2007).
Sal-Man et al., "Arginine mutations within a transmembrane domain of Tar, an *Escherichia coli* aspartate receptor, can drive homodimer dissociation and heterodimer association in vivo," Biochem. J., 385:29-36 (2005).
Sarmay et al., "Mapping and comparison of the interaction sites on the Fc region of IgG responsible for triggering antibody dependent cellular cytotoxicity (ADCC) through different types of human Fc gamma receptor," Mol. Immunol., 29(5):633-9 (1992).
Sato et al., "Reshaping a human antibody to inhibit the interleukin 6-dependent tumor cell growth," Cancer Res., 53(4):851-6 (1993).
Sawabu et al., "Growth arrest-specific gene 6 and Axl signaling enhances gastric cancer cell survival via Akt pathway," Mol. Carcinog., 46(2):155-64 (2007).
Schaeffer et al., "The Rat Glomerular Filtration Barrier Does Not Show Negative Charge Selectivity," Microcirculation, 9:329-342 (2002).
Schmitz et al., "Phage display: a molecular tool for the generation of antibodies—a review," Placenta., 21 Suppl A:S106-12 (2000).
Sebba et al., "Tocilizumab: the first interleukin-6-receptor inhibitor," Am J Health Syst Pharm., Aug. 1, 2008;65(15):1413-8. doi: 10.2146/ajhp070449.
Segal et al., "Bispecific antibodies in cancer therapy," Curr. Opin. Immunol., 11:558-562 (1999).
Shaul, "Exploring the charge space of protein-protein association: a proteomic study," Proteins, 60:341-352 (2005).
Shieh et al., "Expression of axl in lung adenocarcinoma and correlation with tumor progression," Neoplasia., 7(12):1058-64 (2005).
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 276:6591-6604 (2001) (Epub Nov. 28, 2000).
Shire et al., "Challenges in the development of high protein concentration formulations," J. Pharm. Sci., 93(6):1390-402 (2004).
Singer et al., Genes & Genomes 1:63 (1998).
Singer et al., Genes & Genomes, 1991; 67-69.
Singer et al., Genes & Genomes, 1998;1:63-64.
Sinha et al., "Electrostatics in protein binding and function," Curr. Protein Pept. Sci., 3(6):601-14 (2002).
Smans et al., "Bispecific antibody-mediated lysis of primary cultures of ovarian carcinoma cells using multiple target antigens," Int. J. Cancer, 83:270-277 (1999).
Sonkoly et al., "IL-31: a new link between T cells and pruritus in atopic skin inflammation," J. Allergy Clin. Immunol., 117:411-417 (2006).
Spiess et al., "Bispecific antibodies with natural architecture produced by co-culture of bacteria expressing two distinct half-antibodies," Nat Biotechnol., Aug. 2013; 31(8):753-8. doi: 10.1038/nbt.2621. Epub Jul. 7, 2013.
Staerz et al., "Hybrid hybridoma producing a bispecific monoclonal antibody that can focus effector T-cell activity," Proc Natl Acad Sci U.S.A., 83:1453-7 (1986).
Strand et al., "Biologic therapies in rheumatology: lessons learned, future directions," Nat. Rev. Drug Discov., 6(1):75-92 (2007).
Stenhoff et al., "Vitamin K-dependent Gas6 activates ERK kinase and stimulates growth of cardiac fibroblasts," Biochem. Biophys. Res. Commun., 319(3):871-8 (2004).
Sun et al., "Coexpression of Gas6/Axl in human ovarian cancers," Oncology, 66(6):450-7 (2004).
Suresh et al., "Bispecific monoclonal antibodies from hybrid hybridomas," Methods Enzymol., 1986;121:210-228.
Takkinen et al., "Affinity and Specificity Maturation by CDR Walking," Antibody Engineering, Springer Lab Manuals, pp. 540-545 (2001).
Tan et al., "Engineering the isoelectric point of a renal cell carcinoma targeting antibody greatly enhances scFv solubility," Immunotechnology, 4(2):107-114 (1998).
Tarditi et al., "Selective high-performance liquid chromatographic purification of bispecific monoclonal antibodies," J. Chromatogr., 599:13-20 (1992).
Teeling et al., "The biological activity of human CD20 monoclonal antibodies is linked to unique epitopes on CD20," J. Immunol., 177(1):362-71 (2006).
Ten Kate et al., "Effect of isoelectric point on biodistribution and inflammation: imaging with indium-111-labelled IgG," Eur. J. Nucl. Med., 17:305-309 (1990).
Thies et al., "The alternatively folded state of the antibody C(H)3 domain," J. Mol. Biol., 309(5):1077-85 (2001).
Tsubaki et al., "C-terminal modification of monoclonal antibody drugs: amidated species as a general product-related substance," Int J Biol Macromol., 52:139-47. doi: 10.1016/j.ijbiomac.2012.09.016. Epub Sep. 25, 2012.
Tsuchiya, Credit Suisse Seminar, "Therapeutic Antibody," at Fuji-Gotemba Laboratories, p. 21 (2006).
Tsurushita et al., "Design of humanized antibodies: From anti-Tac to Zenapax," Methods, 36:69-83 (2005).
Vaisitti et al., "Cationization of monoclonal antibodies: another step towards the "magic bullet"?," J. Biol. Regul. Homeost. Agents., 19(3-4):105-12 (2005).
Vajdos et al., "Comprehensive functional maps of the antigen-binding site of an anti-ErbB2 antibody obtained with shotgun scanning mutagenesis," J. Mol. Biol., 320(2):415-28 (2002).
Vajkoczy et al., "Dominant-negative inhibition of the Axl receptor tyrosine kinase suppresses brain tumor cell growth and invasion and prolongs survival," Proc. Natl. Acad. Sci. U.S.A., 103(15):5799-804 (2006).

(56) References Cited

OTHER PUBLICATIONS

Van Loghem et al., "Staphylococcal protein A and human IgG subclasses and allotypes," Scand. J. Immunol., 15(3):275-8 (1982).
Van Walle et al., Immunogenicity screening in protein drug development, Expert Opin. Biol. Ther., 7(3):405-18 (2007).
Varnum et al., "Axl receptor tyrosine kinase stimulated by the vitamin K-dependent protein encoded by growth-arrest-specific gene 6," Nature, 373(6515):623-6 (1995).
Wally et al., "Identification of a novel substitution in the constant region of a gene coding for an amyloidogenic kappa1 light chain," Biochim Biophys Acta., May 31, 1999;1454(1):49-56.
Wang et al., "Conserved amino acid networks involved in antibody variable domain interactions," Proteins, Jul. 2009;76(1):99-114. doi: 10.1002/prot.22319.
Wang et al., "Polyethylene Glycol-modified Chimeric Toxin Composed of Transforming Growth Factor alpha and Pseudomonas Exotoxin," Cancer. Res., 53:4588-4594 (1993).
Warnaar et al., "Purification of bispecific F(ab')2 from murine trinoma OC/TR with specificity for CD3 and ovarian cancer," Hybridoma, 13:519-526 (1994).
Wiens et al., "Somatic mutation in VH complementarity-determining region 2 and framework region 2: differential effects on antigen binding and Ig secretion," J. Immunol., 159(3):1293-302 (1997).
Wiens et al., "Mutation of a single conserved residue in VH complementarity-determining region 2 results in a severe Ig secretion defect," J. Immunol., 167(4):2179-86 (2001).
Winkler et al., "Changing the antigen binding specificity by single point mutations of an anti-p24 (HIV-1) antibody," J. Immunol., 165:4505-14 (2000).
Wu et al., "Development of motavizumab, an ultra-potent antibody for the prevention of respiratory syncytial virus infection in the upper and lower respiratory tract," J. Mol. Biol., 368(3):652-65 (2007).
Wu et al., "Humanization of a murine monoclonal antibody by simultaneous optimization of framework and CDR residues," J. Mol. Biol., 294(1):151-62 (1999).
Wypych et al., "Human IgG2 antibodies display disulfide-mediated structural isoforms," J. Biol. Chem., 283(23):16194-16205 (2008).
Xiang et al., "Study of B72.3 combining sites by molecular modeling and site-directed mutagenesis," Protein Eng., 13(5):339-44 (2000).
Yagi et al., "Interleukin-31 stimulates production of inflammatory mediators from human colonic subepithelial myofibroblasts," Int. J. Mol. Med., 19(6):941-946 (2007).
Yamagata et al., "Synaptic adhesion molecules," Curr. Opin. Cell Biol., 15(5):621-32 (2003).
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J. Pharmacol. Exp. Ther., 301:467-477 (2002).
Yang et al., "Tailoring structure-function and pharmacokinetic properties of single-chain Fv proteins by site-specific PEGylation," Protein Eng., 16:761-770 (2003).
Yang et al., "CDR walking mutagenesis for the affinity maturation of a potent human anti-HIV-1 antibody into the picomolar range," J. Mol. Biol., 254(3):392-403 (1995).
Zhu et al., "MHC class I-related neonatal Fc receptor for IgG is functionally expressed in monocytes, intestinal macrophages, and dendritic cells," J. Immunol., 166(5):3266-76 (2001).
Zuckier et al., "Chimeric human-mouse IgG antibodies with shuffled constant region exons demonstrate that multiple domains contribute to in vivo half-life," Cancer Res., 58:3905-08 (1998).
Zwick et al., "The long third complementarity-determining region of the heavy chain is important in the activity of the broadly neutralizing anti-human immunodeficiency virus type 1 antibody 2F5," J. Virol., 78(6):3155-61 (2004).
International Search Report for App. Ser. No. PCT/JP2008/067483, dated Oct. 21, 2008, 2 pages.

International Preliminary Report on Patentability for App. Ser. No. PCT/JP2008/067483, dated Apr. 7, 2010, 13 pages.
International Search Report for App. Ser. No. PCT/JP2009/066590, dated Oct. 20, 2009, 2 pages.
International Preliminary Report on Patentability for PCT App. Ser. No. PCT/JP2008/067499, dated Apr. 7, 2010, 6 pages.
Examiner Dong Jiang, USPTO Restriction Requirement in U.S. Appl. No. 12/680,112, dated Oct. 7, 2011, 6 pages.
Fish & Richardson P.C., Amendment and Response to Species Election Requirement dated Oct. 7, 2011 in U.S. Appl. No. 12/680,112, filed Dec. 6, 2011, 15 pages.
Examiner Dong Jiang, USPTO Non Final Office Action in U.S. Appl. No. 12/680,112, dated Feb. 29, 2012, 8 pages.
Fish & Richardson P.C., Amendment in Reply to Action of Feb. 29, 2012 in U.S. Appl. No. 12/680,112, filed Aug. 27, 2012, 12 pages.
Examiner Dong Jiang, USPTO Restriction Requirement in U.S. Appl. No. 12/680,112, dated Sep. 19, 2012, 6 pages.
Fish & Richardson P.C., Amendment and Reply to Restriction Requirement dated Sep. 19, 2012 in U.S. Appl. No. 12/680,112, filed Oct. 17, 2012, 13 pages.
Examiner Dong Jiang, USPTO Non Final Office Action in U.S. Appl. No. 12/680,112, dated Feb. 4, 2013, 9 pages.
Examiner Bradley Duffy, USPTO Restriction Requirement in U.S. Appl. No. 12/680,082, dated Jun. 6, 2012, 12 pages.
Fish & Richardson P.C., Fourth Preliminary Amendment and Response to Restriction Requirement dated Jun. 6, 2012 in U.S. Appl. No. 12/680,082, filed Jun. 29, 2012, 13 pages.
Examiner Bradley Duffy, USPTO Restriction Requirement in U.S. Appl. No. 12/680,082, dated Sep. 14, 2012, 6 pages.
Fish & Richardson P.C., Amendment and Response to Election Requirement dated Sep. 14, 2012 in U.S. Appl. No. 12/680,082, filed Nov. 8, 2012, 14 pages.
Examiner Bradley Duffy, USPTO Non-Final Office Action in U.S. Appl. No. 12/680,082, dated Feb. 14, 2013, 12 pages.
Fish & Richardson P.C., Amendment in Reply to Non-Final Office Action dated Feb. 14, 2013 in U.S. Appl. No. 12/680,082, filed Aug. 12, 2013, 17 pages.
Examiner Bradley Duffy, USPTO Final Office Action in U.S. Appl. No. 12/680,082, dated Oct. 22, 2013, 12 pages.
Fish & Richardson P.C., Amendment in Reply to Final Office Action dated Oct. 22, 2013 in U.S. Appl. No. 12/680,082, filed Feb. 21, 2014, 14 pages.
Examiner Bradley Duffy, USPTO Interview Summary in U.S. Appl. No. 12/680,082, dated Feb. 25, 2013, 3 pages.
Examiner Bradley Duffy, USPTO Non-Final Office Action in U.S. Appl. No. 12/680,082, dated Feb. 5, 2015, 9 pages.
Fish & Richardson P.C., Amendment in Reply to Non-Final Office Action dated Feb. 5, 2015 in U.S. Appl. No. 12/680,082, filed Apr. 29, 2015, 13 pages.
Examiner Bradley Duffy, USPTO Final Office Action in U.S. Appl. No. 12/680,082, dated May 13, 2015, 10 pages.
Fish & Richardson P.C., Amendment in Reply to Final Office Action dated May 13, 2015 in U.S. Appl. No. 12/680,082, filed Sep. 25, 2015, 18 pages.
Examiner Lynn Anne Bristol, USPTO Restriction Requirement in U.S. Appl. No. 13/257,112, dated Oct. 15, 2013, 10 pages.
Fish & Richardson P.C., Amendment and Response to Election Requirement dated Oct. 15, 2013 in U.S. Appl. No. 13/257,112, filed Nov. 15, 2013, 6 pages.
Examiner Lynn Anne Bristol, USPTO Non-Final Office Action in U.S. Appl. No. 13/257,112, dated Jan. 30, 2014, 18 pages.
Fish & Richardson P.C., Amendment and Reply to Non-Final Office Action dated Jan. 30, 2014 in U.S. Appl. No. 13/257,112, filed Jul. 1, 2014, 12 pages.
Examiner Lynn Anne Bristol, USPTO Final Office Action in U.S. Appl. No. 13/257,112, dated Sep. 5, 2014, 16 pages.
Fish & Richardson P.C., Amendment and Reply to Final Office Action dated Sep. 5, 2014 in U.S. Appl. No. 13/257,112, filed Feb. 5, 2015, 6 pages.
Examiner Lynn Anne Bristol, USPTO Notice of Allowance in U.S. Appl. No. 13/257,112, dated Feb. 23, 2015, 8 pages.
Examiner Lynn Anne Bristol, USPTO Notice of Allowance in U.S. Appl. No. 13/257,112, dated Apr. 2, 2015, 7 pages.

(56) References Cited

OTHER PUBLICATIONS

Examiner Lynn Anne Bristol, USPTO Notice of Allowance in U.S. Appl. No. 13/257,112, dated Aug. 26, 2015, 7 pages.
International Search Report for App. Ser. No. PCT/JP2010/054769, dated Apr. 20, 2010, 4 pages.
International Preliminary Report on Patentability for App. Ser. No. PCT/JP2010/054769, dated Oct. 18, 2011, 6 pages.
Examiner Lynn Anne Bristol, USPTO Restriction Requirement in U.S. Appl. No. 13/257,145, dated Mar. 20, 2013, 11 pages.
Fish & Richardson P.C., Preliminary Amendment and Response to Restriction Requirement dated Mar. 20, 2013 in U.S. Appl. No. 13/257,145, filed Apr. 22, 2013, 7 pages.
Examiner Lynn Anne Bristol, USPTO Non-Final Office Action in U.S. Appl. No. 13/257,145, dated Jul. 2, 2013, 20 pages.
Fish & Richardson P.C., Amendment in Reply to Office Action dated Jul. 2, 2013 in U.S. Appl. No. 13/257,145, filed Dec. 2, 2013, 12 pages.
Examiner Lynn Anne Bristol, USPTO Final Office Action in U.S. Appl. No. 13/257,145, dated Feb. 6, 2014, 12 pages.
Fish & Richardson P.C., Amendment in Reply to Office Action dated Feb. 6, 2014 in U.S. Appl. No. 13/257,145, filed May 6, 2014, 10 pages.
Examiner Lynn Anne Bristol, USPTO Notice of Allowance in U.S. Appl. No. 13/257,145, dated Oct. 1, 2014, 9 pages.
Examiner Lynn Anne Bristol, USPTO Notice of Allowance in U.S. Appl. No. 13/257,145, dated Jan. 9, 2015, 7 pages.
Examiner Lynn Anne Bristol, USPTO Notice of Allowance in U.S. Appl. No. 13/257,145, dated Mar. 11, 2015, 7 pages.
International Search Report for App. Ser. No. PCT/JP2010/054767, dated Jun. 15, 2010, 7 pages.
International Preliminary Report on Patentability for App. Ser. No. PCT/JP2010/054767, dated Oct. 18, 2011, 12 pages.
International Search Report for App. Ser. No. PCT/JP2008/067534, dated Oct. 21, 2008, 4 pages.
International Preliminary Report on Patentability for App. Ser. No. PCT/JP2008/067534, dated Apr. 7, 2010, 7 pages.
International Search Report for App. Ser. No. PCT/JP2009/057309, dated Jul. 7, 2009, 8 pages.
International Preliminary Report on Patentability for App. Ser. No. PCT/JP2009/057309, dated Nov. 30, 2010, 7 pages.
European Search Report for App. Ser. No. EP 09 72 9337, dated Nov. 3, 2011, 3 pages.
Examiner Meera Natarajan, USPTO Restriction Requirement in U.S. Appl. No. 12/295,039, dated Oct. 12, 2010, 9 pages.
Fish & Richardson P.C., Response to Restriction Requirement dated Oct. 12, 2010 in U.S. Appl. No. 12/295,039, filed Apr. 11, 2011, 9 pages.
Examiner Meera Natarajan, USPTO Non-Final Office Action in U.S. Appl. No. 12/295,039, dated Jun. 28, 2011, 9 pages.
Fish & Richardson P.C., Amendment in Reply to Action dated Jun. 28, 2011 in U.S. Appl. No. 12/295,039, filed Dec. 27, 2011, 14 pages.
Examiner Meera Natarajan, USPTO Final Office Action in U.S. Appl. No. 12/295,039, dated Apr. 12, 2012, 8 pages.
Fish & Richardson P.C., Amendment in Reply to Action dated Apr. 12, 2012 in U.S. Appl. No. 12/295,039, filed Sep. 11, 2012, 12 pages.
International Preliminary Report on Patentability for App. Ser. No. PCT/JP2007/057036, dated Oct. 21, 2008, 6 pages.
International Search Report for App. Ser. No. PCT/JP2007/057036, dated May 1, 2007, 2 pages.
European Search Report for App. Ser. No. 07 74 0494, dated Sep. 3, 2009, 3 pages.
International Preliminary Report on Patentability for App. Ser. No. PCT/JP2007/057058, dated Oct. 21, 2008, 11 pages.
International Search Report App. Ser. No. PCT/JP2007/057058, dated May 7, 2001, 2 pages.
Examiner Lynn Anne Bristol, USPTO Restriction Requirement in U.S. Appl. No. 12/295,075, dated Feb. 22, 2011, 9 pages.
Fish & Richardson P.C., Response to Restriction Requirement dated Feb. 22, 2011 in U.S. Appl. No. 12/295,075, filed Aug. 18, 2011, 2 pages.
Examiner Lynn Anne Bristol, USPTO Non-Final Office Action in U.S. Appl. No. 12/295,075, dated Nov. 4, 2011, 14 pages.
Fish & Richardson P.C., Amendment in Reply to Action dated Nov. 4, 2011 in U.S. Appl. No. 12/295,075, filed May 3, 2012, 12 pages.
Examiner Lynn Anne Bristol, USPTO Final Office Action in U.S. Appl. No. 12/295,075, dated Jul. 19, 2012, 12 pages.
Fish & Richardson P.C., Amendment in Reply to Action dated Jul. 19, 2012 in U.S. Appl. No. 12/295,075, filed Jan. 17, 2013, 113 pages.
Examiner Nelson B. Moseley II, USPTO Non-Final Office Action in U.S. Appl. No. 12/295,075, dated Jun. 7, 2013, 17 pages.
Examiner Bradley Duffy, USPTO Restriction Requirement in U.S. Appl. No. 11/910,128, dated Jun. 9, 2011, 10 pages.
Fish & Richardson P.C., Response to Restriction Requirement dated Jun. 9, 2011 in U.S. Appl. No. 11/910,128, filed Dec. 2, 2011, 1 page.
Examiner Stephen L. Rawlings, USPTO Non-Final Office Action in U.S. Appl. No. 11/910,128, dated Apr. 25, 2012, 21 pages.
Fish & Richardson P.C., Amendment in Reply to Office Action dated Apr. 25, 2012 in U.S. Appl. No. 11/910,128, filed Oct. 25, 2012, 32 pages.
Fish & Richardson P.C., Supplemental Amendment in U.S. Appl. No. 11/910,128, filed Nov. 14, 2012, 20 pages.
Examiner Stephen L. Rawlings, USPTO Final Office Action in U.S. Appl. No. 11/910,128, dated Sep. 10, 2013, 12 pages.
International Preliminary Report on Patentability for App. Ser. No. PCT/JP2009/066590, dated May 10, 2011, 6 pages.
International Preliminary Report on Patentability for App. Ser. No. PCT/JP2009/070376, dated Jul. 5, 2011, 11 pages.
Examiner Dong Jiang, USPTO Non-Final Office Action U.S. Appl. No. 12/680,087, dated Oct. 27, 2011, 6 pages.
Fish & Richardson P.C., Amendment and Reply to Action dated Oct. 27, 2011 in U.S. Appl. No. 12/680,087, filed Jan. 26, 2012, 6 pages.
Examiner Dong Jiang, USPTO Notice of Allowance in U.S. Appl. No. 12/680,087, dated Feb. 24, 2012, 5 pages.
Examiner Dong Jiang, USPTO Notice of Allowance in U.S. Appl. No. 12/680,087, dated Jun. 25, 2012, 11 pages.
Examiner Dong Jiang, USPTO Notice of Allowance in U.S. Appl. No. 12/680,087, dated Nov. 26, 2012, 7 pages.
Examiner Dong Jiang, USPTO Notice of Allowance in U.S. Appl. No. 12/680,087, dated Apr. 15, 2013, 9 pages.
Examiner Dong Jiang, USPTO Notice of Allowance in U.S. Appl. No. 12/680,087, dated Aug. 2, 2013, 8 pages.
Examiner James L. Rogers, USPTO Restriction Requirement in U.S. Appl. No. 12/936,587, dated Dec. 6, 2011, 5 pages.
Fish & Richardson P.C., Third Preliminary Amendment and Response to Restriction Requirement dated Dec. 6, 2011 in U.S. Appl. No. 12/936,587, filed Jun. 5, 2012, 7 pages.
Examiner James L. Rogers, USPTO Restriction Requirement in U.S. Appl. No. 12/936,587, dated Jun. 25, 2012, 5 pages.
Fish & Richardson P.C., Response to Species Election Requirement dated Jun. 25, 2012 in U.S. Appl. No. 12/936,587, filed Jul. 25, 2012, 1 page.
Examiner James L. Rogers, USPTO Non-Final Office Action in U.S. Appl. No. 12/936,587, dated Nov. 7, 2012, 13 pages.
International Preliminary Report on Patentability for App. Ser. No. PCT/JP2010/058166, dated Dec. 16, 2011, 15 pages.
International Search Report for App. Ser. No. PCT/JP2010/066490, dated Nov. 9, 2010, 5 pages.
International Preliminary Report on Patentability for App. Ser. No. PCT/JP2010/066490, dated Apr. 11, 2012, 6 pages.
Examiner Julie Zhen Qin Wu, USPTO Restriction Requirement in U.S. Appl. No. 12/745,781, dated Sep. 4, 2012, 10 pages.
Fish & Richardson P.C., Response to Restriction Requirement dated Sep. 4, 2012 in U.S. Appl. No. 12/745,781, filed Sep. 21, 2012, 176 pages.
Examiner Julie Zhen Qin Wu, USPTO Non-Final Office Action in U.S. Appl. No. 12/745,781, dated Oct. 18, 2012, 21 pages.

(56) References Cited

OTHER PUBLICATIONS

Fish & Richardson P.C., Amendment in Reply to Office Action dated Oct. 18, 2012 in U.S. Appl. No. 12/745,781, filed Apr. 17, 2013, 23 pages.
Examiner Julie Zhen Qin Wu, USPTO Final Office Action in U.S. Appl. No. 12/745,781, dated May 21, 2013, 16 pages.
Examiner Jessica Hope Roark, USPTO Restriction Requirement in U.S. Appl. No. 12/679,922, dated Oct. 2, 2012, 9 pages.
Fish & Richardson P.C., Response to Restriction Requirement dated Oct. 2, 2012 in U.S. Appl. No. 12/679,922, filed Nov. 1, 2012, 2 pages.
Examiner Jessica Hope Roark, USPTO Non-Final Office Action in U.S. Appl. No. 12/679,922, dated Jan. 3, 2013, 25 pages.
Fish & Richardson P.C., Amendment in Reply to Action dated Jan. 3, 2013 in U.S. Appl. No. 12/679,922, filed Jul. 2, 2013, 18 pages.
Examiner Jessica Hope Roark, USPTO Final Office Action in U.S. Appl. No. 12/679,922, dated Aug. 2, 2013, 12 pages.
International Preliminary Report on Patentability for App. Ser. No. PCT/JP2010/073361, dated Aug. 14, 2012, 7 pages.
Examiner James L. Rogers, USPTO Non-Final Office Action in U.S. Appl. No. 13/595,139, dated Nov. 14, 2012, 10 pages.
International Search Report for App. Ser. No. PCT/JP2011/055101, dated May 10, 2011, 4 pages.
International Preliminary Report on Patentability for App. Ser. No. PCT/JP2011/055101, dated Oct. 2, 2012, 6 pages.
Examiner Michael D. Allen, USPTO Restriction Requirement in U.S. Appl. No. 13/497,269, dated Dec. 6, 2012, 9 pages.
Fish & Richardson P.C., Response to Restriction Requirement dated Dec. 6, 2012 in U.S. Appl. No. 13/497,269, filed May 1, 2013, 2 pages.
Examiner Michael D. Allen, USPTO Non-Final Office Action in U.S. Appl. No. 13/497,269, dated Aug. 15, 2013, 13 pages.
Fish & Richardson P.C., Reply to Non-Final Action dated Aug. 15, 2013 in U.S. Appl. No. 13/497,269, filed Nov. 15, 2013, 13 pages.
Examiner Michael D. Allen, USPTO Final Office Action in U.S. Appl. No. 13/497,269, dated Mar. 14, 2014, 10 pages.
Fish & Richardson P.C., Reply to Final Office Action dated Mar. 14, 2014 in U.S. Appl. No. 13/497,269, filed Sep. 10, 2014, 12 pages.
Examiner Michael D. Allen, USPTO Non-Final Office Action in U.S. Appl. No. 13/497,269, dated Jun. 1, 2015, 21 pages.
Examiner Sandra L. Wegert, USPTO Restriction Requirement in U.S. Appl. No. 12/809,138, dated Dec. 13, 2012, 8 pages.
Fish & Richardson P.C., Response to Restriction Requirement dated Dec. 13, 2012 in U.S. Appl. No. 12/809,138, filed Apr. 5, 2013, 2 pages.
Examiner Bruce D. Hissong, USPTO Notice of Allowance in U.S. Appl. No. 12/809,138, dated Aug. 23, 2013, 9 pages.
Examiner Bradley Duffy, USPTO Restriction Requirement in U.S. Appl. No. 13/320,317, dated Dec. 18, 2012, 13 pages.
Fish & Richardson P.C., Response to Restriction Requirement dated Dec. 18, 2012 in U.S. Appl. No. 13/320,317, filed Jan. 18, 2013, 3 pages.
Examiner Bradley Duffy, USPTO Non-Final Office Action in U.S. Appl. No. 13/320,317, dated Dec. Apr. 25, 2013, 25 pages.
Examiner Dong Jiang, USPTO Restriction Requirement in U.S. Appl. No. 13/524,528, dated Mar. 21, 2013, 7 pages.
Fish & Richardson P.C., Reply to Restriction Requirement dated Mar. 21, 2013 in U.S. Appl. No. 13/524,528, filed Sep. 13, 2013, 1 page.
Examiner Dong Jiang, USPTO Non-Final Office Action in U.S. Appl. No. 13/524,528, dated Sep. 30, 2013, 9 pages.
Examiner Michael D. Allen, USPTO Restriction Requirement in U.S. Appl. No. 13/582,073, dated Feb. 6, 2014, 9 pages.
Fish & Richardson P.C., Response to Restriction Requirement dated Feb. 6, 2014 in U.S. Appl. No. 13/582,073, filed Apr. 7, 2014, 1 page.
Examiner Michael D. Allen, USPTO Non-Final Office Action in U.S. Appl. No. 13/582,073, dated Jul. 18, 2014, 10 pages.
Fish & Richardson P.C., Amendment in Reply to Action dated Jul. 18, 2014 in U.S. Appl. No. 13/582,073, filed Jan. 20, 2015, 32 pages.
Examiner Michael D. Allen, USPTO Final Office Action in U.S. Appl. No. 13/582,073, dated Apr. 21, 2015, 10 pages.
U.S. Appl. No. 15/490,936, filed Apr. 19, 2017, Igawa et al.
U.S. Appl. No. 15/562,186, filed Sep. 27, 2017, Igawa et al.
U.S. Appl. No. 15/614,842, filed Jun. 6, 2017, Igawa et al.
U.S. Appl. No. 15/725,692, filed Oct. 5, 2017, Igawa et al.
U.S. Appl. No. 15/782,256, filed Oct. 12, 2017, Igawa et al.
Akira et al., "Interleukin-6 in Biology and Medicine," Adv Immunol., Dec. 31, 1993; 54:1-78.
Annual Report 2012 (Integrated Edition Including CSR Report) Mar. 27, 2013, 154 pages.
Araki et al., "Clinical improvement in a patient with neuromyelitis optica following therapy with the anti-IL-6 receptor monoclonal antibody tocilizumab," Mod Rheumatol. Jul. 2013 ;23(4) :827-31. doi: 10. 1007/s10165-012-0715-9. Epub Jul. 11, 2012.
Aricha et al., "Blocking of IL-6 suppresses experimental autoimmune myasthenia gravis," J Autoimmun. Mar. 2011;36(2) :135-41. doi: 10. 1016/j. jaut. 2010. 12. 001. Epub Dec. 30, 2010.
Arndt et al., "Factors influencing the dimer to monomer transition of an antibody single-chain Fv fragment," Biochemistry, Sep. 15, 1998;37(37):12918-26.
Ciiatellier et al., "Functional mapping of conserved residues located at the VL and VH domain interface of a Fab," J. Mol. Biol., Nov. 22, 1996;264(1):1-6.
Davies et al., "Antibody VH domains as small recognition units," Biotechnology (N.Y.), May 1995;13(5):475-79.
Gunawardane et al., "Agonistic Human Antibodies Binding to Lecithin-Cholesterol Acyltransferase Modulate High Density Lipoprotein Metabolism," J Biol Chem. Feb. 5, 2016;291(6):2799-811. doi: 10.1074/ibc.M11S.672790. Epub Dec. 7, 2015.
Hattori, Introduction of ART-Ig and application to hemophilia A treatment, Chugai Seiyaku ni Okeru Dokuji no Kakushinteki Kotai Gijutsu. Dec. 2012; 18: 42-57 (with English translation).
Hirano et al., "Complementary DNA for a novel human interleukin (BSF-2) that induces B lymphocytes to produce immunoglobulin," Nature, 324: 73-76 (Nov. 1986).
Hirata et al., "Characterization of IL-6 Receptor Expression by Monoclonal and Polyclonal Antibodies," J lmmunol. Nov. 1, 1989;143(9) :2900-6.
Huang et al., "A Monoclonal Anti-Human IL-6 Receptor Antibody Inhibits the Proliferation of Human Myeloma Cells," Hybridoma. Oct. 1993:12(5) :621-30.
Janeway et al., "Antigen Recognition by B-cell and T-cell Receptors," Immunobiology, 5$^{th}$ edition. 2001 :Extract from Chapter 3, pp. 93-122.
Janeway et al., "The Generation of Lymphocyte Antigen Receptors," Immunobiology, 5$^{th}$ edition. 2001 :Extract from Chapter 4, pp. 123-154.
Johnson et al., "Kabat database and its applications: 30 years after the first variability plot," Nucleic Acids Res., Jan. 1, 2000;28(1):214-8.
Jung et al., "The importance of framework residues H6, H7 and H10 in antibody heavy chains: experimental evidence for a new structural subclassification of antibody V(H) domains," J. Mol. Biol., Jun. 8, 2001;309(3):701-16.
Kabat et al., National Institutes of Health, Publ'n No. 91-3242, Sequences of Proteins of Immunological Interest, vol. 1, pp. 647-660 (5$^{th}$ ed. 1991).
Khalifa et al., "Effects on interaction kinetics of mutations at the VH-VL interface of Fabs depend on the structural context," J. Mol. Recognit., May-Jun. 2000;13(3):127-39.
Kipriyanov et al., "Bispecific tandem diabody for tumor therapy with improved antigen binding and pharmacokinetics," J. Mol. Biol., Oct. 15, 1999;293(1):41-56.
Kipriyanov et al., "Effect of domain order on the activity of bacterially produced bispecific single-chain Fv antibodies," J. Mol. Biol., Jun. 27, 2003;330(1):99-111.
Kontermann, "Recombinant bispecific antibodies for cancer therapy," Acta Pharmacol Sin., Jan. 2005;26(1):1-9.

(56) References Cited

OTHER PUBLICATIONS

Korn et al., "Recombinant bispecific antibodies for the targeting of adenoviruses to CEA-expressing tumour cells: a comparative analysis of bacterially expressed single-chain diabody and tandem scFv," J. Gene Med., Jun. 2004;6(6):642-51.

Krieckaert et al., "Immunogenicity of biologic therapies—we need tolerance," Nat. Rev. Rheumatol. Oct. 2010;6(10) :558-9. doi: 10.1038/nrrheum. 2010. 153.

Kumar et al., "The second PDZ domain of INAD is a type I domain involved in binding to eye protein kinase C. Mutational analysis and naturally occurring variants," J. Biol. Chem., Jul. 6, 2001;276(27): 24971-7. Epub May 7, 2001.

Labrijn et al., "Controlled Fab-arm exchange for the generation of stable bispecific IgG1," Nat. Protoc. Oct. 2014; 9(10): 2450-63. doi: 10.1038/nprot.2014.169. Epub Sep. 25, 2014.

Le Gall et al., "Effect of linker sequences between the antibody variable domains on the formation, stability and biological activity of a bispecific tandem diabody," Protein Eng. Des. Sel., Apr. 2004;17(4):357-66. Epub May 4, 2004.

Liu et al., "Functional interactions between arginine-133 and aspartate-88 in the human reduced folate carrier: evidence for a charge-pair association," Biochem. J., Sep. 2001;358(Pt. 2): 511-6.

Lotz et al., "B Cell Stimulating Factor 2/Interleukin 6 is a Costimulant for Human Thymocytes and T Lymphocytes," J. Exp. Med., Mar. 1, 1988; 167(3): 1253-1258.

Maity et al., "Equilibrium unfolding of dimeric and engineered monomeric forms of lambda Cro (F58W) repressor and the effect of added salts: evidence for the formation of folded monomer induced by sodium perchlorate," Arch. Biochem. Biophys., Feb. 1, 2005;434(1):93-107.

Murata et al., "Anti-Digoxin Fab Variants Generated by Phage Display," Mol Biotechnol. Jun. 2013 :54 (2) :269-77. doi : 10.1007/s12033-012-9564-1.

Narhi et al., "Asn to Lys mutations at three sites which are N-glycosylated in the mammalian protein decrease the aggregation of *Escherichia coli*-derived erythropoietin," Protein Eng., Feb. 2001;14(2):135-40.

Nieba et al., "Disrupting the hydrophobic patches at the antibody variable/constant domain interface: improved in vivo folding and physical characterization of an engineered scFv fragment," Protein Eng., Apr. 1997;10(4):435-44.

Nishimoto et al., "Humanized anti-interleukin-6 receptor antibody treatment of multicentric Castleman disease," Blood, 106(8):2627-32 (2005).

Nohaile et al., "Altering dimerization specificity by changes in surface electrostatics," Proc. Natl. Acad. Sci. U.S.A., Mar. 13, 2001;98(6):3109-14.

Novick et al., "Monoclonal Antibodies to the Soluble Human IL-6 Receptor: Affinity Purification, Elisa, and Inhibition of Ligand Binding," Hybridoma. Feb. 1991;10(1) :137-46.

Okabe, Proprietary Innovative Antibody Engineering Technologies in Chugai Pharmaceutical: Dec. 18, 2012, 78 pages.

Padlan et al., "X-ray crystallography of antibodies," Adv Protein Chem., 1996;49:57-133.

Pejchal et al., "A Conformational Switch in Human Immunodeficiency Virus gp41 Revealed by the Structures of Overlapping Epitopes Recognized by Neutralizing Antibodies," J Virol. Sep. 2009;83 (17): 8451-62. do i : 10. 1128/ JVI. 00685- 09. Epub Jun. 10, 2009.

Peters et al., "Engineering an improved IgG4 molecule with reduced disulfide bond heterogeneity and increased Fab domain thermal stability," J Biol Chem. Jul. 13, 2012; 287(29): 24525-33. doi: 10.1074/jbc.M112.369744. Epub May 18, 2012.

Pokkuluri et al., "A domain flip as a result of a single amino-acid substitution," Structure, Aug. 15, 1998;6(8):1067-73.

Rader et al., "A phage display approach for rapid antibody humanization: designed combinatorial V gene libraries," Proc. Natl. Acad. Sci. U.S.A., Jul. 21, 1998;95(15):8910-5.

Raposo et al., "Epitope-specific antibody response is controlled by immunoglobulin Vh polymorphisms," J Exp Med. Mar. 10, 2014:211 (3):405-11. doi : 10. 1084/ jem. 20130968. Epub Feb. 17, 2014.

Reichert, "Antibodies to watch in 2014," mAbs, 6(4): 799-802 (Jul./Aug. 2014).

Taga et al., "Interleukin-6 Triggers the Association of Its Receptor with a Possible Signal Transducer, gp130," Cell. Aug. 11, 1989; 58(3): 573-581.

Taga et al., "Receptors for B Cell Stimulatory Factor 2," J. Exp. Med. Oct. 1, 1987; 166(4): 967-981.

Tan et al., "Contributions of a highly conserved VH/VL hydrogen bonding interaction to scFv folding stability and refolding efficiency," Biophys. J., Sep. 1998;75(3):1473-82.

Vargas-Madrazo et al., "An improved model of association for VH-VL immunoglobulin domains: asymmetries between VH and VL in the packing of some interface residues," J. Mol. Recognit., May-Jun. 2003;16(3):113-20.

Ward et al., "Binding activities of a repertoire of single immunoglobulin variable domains secreted from *Escherichia coli*," Nature, 1989;341:544-546.

Worn et al., "Stability engineering of antibody single-chain Fv fragments," J. Mol. Biol., Feb. 2, 2001;305(5):989-1010.

Wu et al., "Multimerization of a chimeric anti-CD20 single-chain Fv-Fc fusion protein is mediated through variable domain exchange," Protein Eng., Dec. 2001;14(12):1025-33.

Yamasaki et al., "Cloning and Expression of the Human Interleukin-6 (BSF-2/IFNb 2) Receptor," Science. Aug. 1988 12:241 (4867) :825-28.

Zhu et al., "Remodeling domain interfaces to enhance heterodimer formation," Protein Sci., Apr. 1997;6(4):781-8.

Examiner Lynn Anne Bristol, USPTO Advisory Action in U.S. Appl. No. 13/257,145, dated May 14, 2014, 5 pages.

Examiner Lynn Anne Bristol, Reply to Advisory Action in U.S. Appl. No. 13/257,145 dated May 14, 2014, filed Jun. 3, 2014, 8 pages.

Fish & Richardson P.C., Reply to Office Action dated Jun. 1, 2015 in U.S. Appl. No. 13/497,269, filed Sep. 30, 2015, 31 pages.

Examiner Michael D. Allen, USPTO Non-Final Office Action in U.S. Appl. No. 13/497,269, dated Dec. 20, 2016, 27 pages.

Examiner Michael D. Allen, USPTO Final Office Action in U.S. Appl. No. 13/582,073, dated May 24, 2017, 19 pages.

U.S. Appl. No. 13/524,528, Igawa et al., filed Jun. 15, 2012 (abandoned).

U.S. Appl. No. 12/680,112, Igawa et al., filed Jun. 23, 2010 (abandoned).

U.S. Appl. No. 13/959,489, Igawa et al., filed Aug. 5, 2013 (abandoned).

U.S. Appl. No. 12/745,781, Kuramochi et al., filed Sep. 13, 2010 (abandoned).

U.S. Appl. No. 13/257,145, Igawa et al., filed Nov. 22, 2011 (abandoned).

U.S. Appl. No. 13/518,861, Igawa et al., filed Oct. 4, 2012 (abandoned).

U.S. Appl. No. 15/490,396, Igawa et al., filed Apr. 19, 2017.

U.S. Appl. No. 12/295,075, Igawa et al., filed Apr. 20, 2009.

U.S. Appl. No. 12/680,082, Igawa et al., filed Jun. 25, 2010.

U.S. Appl. No. 14/047,316, Kuramochi et al., filed Oct. 7, 2013.

U.S. Appl. No. 13/257,112, Igawa et al., filed Nov. 22, 2011.

U.S. Appl. No. 13/320,317, Maeda et al., filed Feb. 1, 2012.

U.S. Appl. No. 15/553,609, filed Aug. 25, 2017, Kakehi et al.

U.S. Appl. No. 15/875,847, filed Jan. 19, 2018, Igawa et al.

Geneseq Accession No. AEM45140, Feb. 22, 2007, "Light chain constant region of therapeutic human IgG antibody", 1 page.

Gershoni et al., "Epitope Mapping," Biodrugs, May 2007;21(3):145-56.

Golay et al., "Mechanism of action of therapeutic monoclonal antibodies: Promises and pitfalls of in vitro an in vivo assays," Archives of Biochemistry and Biophysics 526: 146-153, 2012.

Petkova et al., "Enhanced half-life of genetically engineered human IgG1 antibodies in a humanized FcRn mouse model: potential applicaton in humorally mediated autoimmune disease," Int Immunol. Dec. 2006;18(12):1759-69. Epub Oct. 31, 2006.

(56) References Cited

OTHER PUBLICATIONS

Stancovski et al., "Mechanistic Aspects of the Opposing Effects of Monoclonal Antibodies to the ERBB2 Receptor on Tumor Growth," Proc Natl Acad Sci USA, 88: 8691-8695, 1991.
Vaccaro et al., "Divergent activities of an engineered antibody in murine and human systems have implications for therapeutic antibodies," Proc Natl Acad Sci USA. Dec. 5, 2006: 103(49):18709-14. Epub Nov. 20, 2006.
Yarilin, Fundamentals of Immunology M:Medicina, 1999, pp. 169-72, 354-8 (With English translation), 21 pages.
U.S. Pat. No. 8,562,991, Igawa et al., issued Oct. 22, 2013.
U.S. Appl. No. 13/524,528, Igawa et al., filed Jun. 15, 2012.
U.S. Appl. No. 14/520,423, Igawa et al., filed Oct. 22, 2014.
U.S. Pat. No. 9,688,762, Igawa et al., issued Jun. 27, 2017.
U.S. Appl. No. 15/614,842, Igawa et al., filed Jun. 6, 2017.
U.S. Appl. No. 12/680,112, Igawa et al., filed Jun. 23, 2010.
U.S. Appl. No. 13/959,489, Igawa et al., filed Aug. 5, 2013.
U.S. Appl. No. 15/263,617, Igawa et al., filed Sep. 13, 2016.
U.S. Appl. No. 12/745,781, Kuramochi et al., filed Sep. 13, 2010.
U.S. Appl. No. 14/340,883, Kuramochi et al., filed Jul. 25, 2014.
U.S. Pat. No. 8,575,317, Kuramochi et al., issued Nov. 5, 2013.
U.S. Pat. No. 9,399,680, Kuramochi et al., issued Jul. 26, 2016.
U.S. Pat. No. 9,228,017, Igawa et al., issued Jan. 5, 2016.
U.S. Appl. No. 13/257,145, Igawa et al., filed Nov. 22, 2011.
U.S. Appl. No. 14/680,250, Igawa et al., filed Apr. 7, 2015.
U.S. Pat. No. 9,340,615, Maeda et al., issued May 17, 2016.
U.S. Appl. No. 13/497,269, Kuramochi et al., filed Jun. 1, 2012.
U.S. Appl. No. 13/518,861, Igawa et al., filed Oct. 4, 2012.
U.S. Appl. No. 15/617,008, Igawa et al., filed Jun. 8, 2017.
U.S. Appl. No. 13/582,073, Kuramochi et al., filed Dec. 20, 2012.
U.S. Appl. No. 15/024,063, Igawa et al., filed Mar. 23, 2016.
U.S. Appl. No. 15/562,186, Igawa et al., filed Sep. 27, 2017.
U.S. Appl. No. 15/553,609, Kakehi et al., filed Aug. 25, 2017.
U.S. Appl. No. 11/910,128, Igawa et al., filed Oct. 7, 2008.
U.S. Appl. No. 15/782,256, Igawa et al., filed Oct. 12, 2017.
U.S. Appl. No. 12/295,039, Igawa et al., filed Jan. 20, 2009.
U.S. Pat. No. 9,670,269, Igawa et al., issued Jun. 6, 2017.
U.S. Appl. No. 15/490,936, Igawa et al., filed Apr. 19, 2017.
U.S. Pat. No. 9,096,651, Igawa et al., issued Aug. 4, 2015.
U.S. Appl. No. 14/741,786, Igawa et al., filed Jun. 17, 2015.
U.S. Appl. No. 15/725,692, Igawa et al., filed Oct. 5, 2017.
U.S. Appl. No. 15/875,847, Igawa et al., filed Jan. 19, 2018.

\* cited by examiner

SEQUENCE LISTING

```
<160> NUMBER OF SEQ ID NOS: 16

<210> SEQ ID NO 1
<211> LENGTH: 449
<212> TYPE: PRT
<213> ORGANISM: Artificial Sequence
<220> FEATURE:
<223> OTHER INFORMATION: Artificially synthesized antibody heavy chain
      sequence

<400> SEQUENCE: 1

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45
```

```
Ile Gly Tyr Ile Ser Tyr Ser Gly Ile Thr Thr Tyr Asn Pro Ser Leu
     50                  55                  60

Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

```
<210> SEQ ID NO 2
<211> LENGTH: 214
<212> TYPE: PRT
<213> ORGANISM: Artificial Sequence
<220> FEATURE:
<223> OTHER INFORMATION: Artificially synthesized Antibody light chain
      sequence

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 448
<212> TYPE: PRT
<213> ORGANISM: Artificial Sequence
<220> FEATURE:
<223> OTHER INFORMATION: Artificially synthesized Antibody heavy chain
      sequence

<400> SEQUENCE: 3

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
```

```
                    85                  90                  95
Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 4
<211> LENGTH: 447
<212> TYPE: PRT
<213> ORGANISM: Artificial Sequence
<220> FEATURE:
<223> OTHER INFORMATION: Aritificially synthesized Antibody heavy chain
      sequence

<400> SEQUENCE: 4
```

-continued

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

Ala Leu His Asn His Tyr Thr Gln Lys Ser Leu Ser Leu Ser Pro
            435                 440                 445

<210> SEQ ID NO 5
<211> LENGTH: 445
<212> TYPE: PRT
<213> ORGANISM: Artificial Sequence
<220> FEATURE:
<223> OTHER INFORMATION: Artificially synthesized Antibody heavy chain
      sequence

<400> SEQUENCE: 5

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 6
<211> LENGTH: 443
<212> TYPE: PRT
<213> ORGANISM: Artificial Sequence
<220> FEATURE:
<223> OTHER INFORMATION: Artificially synthesized Antibody heavy chain
      sequence

<400> SEQUENCE: 6

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Ser Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
              260                 265                 270

Phe Asn Trp Tyr Val Asp Gly Val Glu Val His Asn Ala Lys Thr Lys
              275                 280                 285

Pro Arg Glu Glu Gln Phe Asn Ser Thr Phe Arg Val Val Ser Val Leu
  290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
              325                 330                 335

Thr Lys Gly Gln Pro Arg Glu Pro Gln Val Tyr Thr Leu Pro Pro Ser
              340                 345                 350

Gln Glu Glu Met Thr Lys Asn Gln Val Ser Leu Thr Cys Leu Val Lys
              355                 360                 365

Gly Phe Tyr Pro Ser Asp Ile Ala Val Glu Trp Glu Ser Asn Gly Gln
              370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
              405                 410                 415

Glu Gly Asn Val Phe Ser Cys Ser Val Met His Glu Ala Leu His Asn
              420                 425                 430

His Tyr Thr Gln Lys Ser Leu Ser Leu Ser Pro
              435                 440

<210> SEQ ID NO 7
<211> LENGTH: 330
<212> TYPE: PRT
<213> ORGANISM: Homo sapiens

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
              20                  25                  30

Phe Pro Glu Pro Val Thr Val Ser Trp Asn Ser Gly Ala Leu Thr Ser
              35                  40                  45

Gly Val His Thr Phe Pro Ala Val Leu Gln Ser Ser Gly Leu Tyr Ser
          50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
              85                  90                  95

Lys Val Glu Pro Lys Ser Cys Asp Lys Thr His Thr Cys Pro Pro Cys
              100                 105                 110

Pro Ala Pro Glu Leu Leu Gly Gly Pro Ser Val Phe Leu Phe Pro Pro
          115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
              165                 170                 175

Glu Gln Tyr Asn Ser Thr Tyr Arg Val Val Ser Val Leu Thr Val Leu

```
            180                 185                 190
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 8
<211> LENGTH: 326
<212> TYPE: PRT
<213> ORGANISM: Homo sapiens

<400> SEQUENCE: 8

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220
```

```
Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 9
<211> LENGTH: 327
<212> TYPE: PRT
<213> ORGANISM: Homo sapiens

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

```
Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 10
<211> LENGTH: 326
<212> TYPE: PRT
<213> ORGANISM: Artificial Sequence
<220> FEATURE:
<223> OTHER INFORMATION: Artificially synthesized Antibody CH sequence

<400> SEQUENCE: 10

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300
```

Ser Val Met His Glu Ala Leu His Asn His Tyr Thr Gln Lys Ser Leu
305                 310                 315                 320

Ser Leu Ser Pro Gly Lys
                325

<210> SEQ ID NO 11
<211> LENGTH: 326
<212> TYPE: PRT
<213> ORGANISM: Artificial Sequence
<220> FEATURE:
<223> OTHER INFORMATION: Artificially synthesized Antibody CH sequence

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Ser Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 12
<211> LENGTH: 972
<212> TYPE: DNA
<213> ORGANISM: Artificial Sequence
<220> FEATURE:
<223> OTHER INFORMATION: Aritificially synthesized Antibody CH sequence
<220> FEATURE:
<221> NAME/KEY: CDS
<222> LOCATION: (1)..(972)

<400> SEQUENCE: 12

```
gct agc acc aag ggc cca tcg gtc ttc ccc ctg gcg ccc tgc tcc agg      48
Ala Ser Thr Lys Gly Pro Ser Val Phe Pro Leu Ala Pro Cys Ser Arg
1               5                   10                  15 agc acc tcc gag agc aca gcg gcc ctg ggc tgc ctg gtc aag gac tac      96
Ser Thr Ser Glu Ser Thr Ala Ala Leu Gly Cys Leu Val Lys Asp Tyr
                20                  25                  30 ttc ccc gaa ccg gtg acg gtg tcg tgg aac tca ggc gct ctg acc agc     144
Phe Pro Glu Pro Val Thr Val Ser Trp Asn Ser Gly Ala Leu Thr Ser
            35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
        50                  55                  60 ctc agc agc gtg gtg acc gtg ccc tcc agc aac ttc ggc acc cag acc     240
Leu Ser Ser Val Val Thr Val Pro Ser Ser Asn Phe Gly Thr Gln Thr
65                  70                  75                  80 tac acc tgc aac gta gat cac aag ccc agc aac acc aag gtg gac aag     288
Tyr Thr Cys Asn Val Asp His Lys Pro Ser Asn Thr Lys Val Asp Lys
                85                  90                  95 aca gtt gag cgc aaa tct tct gtc gag tgc cca ccg tgc cca gca cca     336
Thr Val Glu Arg Lys Ser Ser Val Glu Cys Pro Pro Cys Pro Ala Pro
                100                 105                 110 cct gtg gca gga ccg tca gtc ttc ctc ttc ccc cca aaa ccc aag gac     384
Pro Val Ala Gly Pro Ser Val Phe Leu Phe Pro Pro Lys Pro Lys Asp
            115                 120                 125 acc ctc atg atc tcc cgg acc cct gag gtc acg tgc gtg gtg gtg gac     432
Thr Leu Met Ile Ser Arg Thr Pro Glu Val Thr Cys Val Val Val Asp
        130                 135                 140 gtg agc cag gaa gac ccc gag gtc cag ttc aac tgg tac gtg gac ggc     480
Val Ser Gln Glu Asp Pro Glu Val Gln Phe Asn Trp Tyr Val Asp Gly
145                 150                 155                 160 gtg gag gtg cat aat gcc aag aca aag cca cgg gag gag cag ttc aac     528
Val Glu Val His Asn Ala Lys Thr Lys Pro Arg Glu Glu Gln Phe Asn
                165                 170                 175 agc acg ttc cgt gtg gtc agc gtc ctc acc gtc gtg cac cag gac tgg     576
Ser Thr Phe Arg Val Val Ser Val Leu Thr Val Val His Gln Asp Trp
                180                 185                 190 ctg aac ggc aag gag tac aag tgc aag gtc tcc aac aaa ggc ctc ccg     624
Leu Asn Gly Lys Glu Tyr Lys Cys Lys Val Ser Asn Lys Gly Leu Pro
            195                 200                 205 gcc ccc atc gag aaa acc atc tcc aaa acc aaa ggg cag ccc cga gaa     672
Ala Pro Ile Glu Lys Thr Ile Ser Lys Thr Lys Gly Gln Pro Arg Glu
        210                 215                 220 cca cag gtg tac acc ctg ccc cca tcc cag gag gag atg acc aag aac     720
Pro Gln Val Tyr Thr Leu Pro Pro Ser Gln Glu Glu Met Thr Lys Asn
225                 230                 235                 240 cag gtc agc ctg acc tgc ctg gtc aaa ggc ttc tac ccc agc gac atc     768
Gln Val Ser Leu Thr Cys Leu Val Lys Gly Phe Tyr Pro Ser Asp Ile
                245                 250                 255 gcc gtg gag tgg gag agc aat ggg cag ccg gag aac aac tac aag acc     816
Ala Val Glu Trp Glu Ser Asn Gly Gln Pro Glu Asn Asn Tyr Lys Thr
```

```
                Ala Val Glu Trp Glu Ser Asn Gly Gln Pro Glu Asn Asn Tyr Lys Thr
                            260                 265                 270 acg cct ccc atg ctg gac tcc gac ggc tcc ttc ttc ctc tac agc aag        864
Thr Pro Pro Met Leu Asp Ser Asp Gly Ser Phe Phe Leu Tyr Ser Lys
            275                 280                 285 ctc acc gtg gac aag agc agg tgg cag gag ggg aac gtc ttc tca tgc        912
Leu Thr Val Asp Lys Ser Arg Trp Gln Glu Gly Asn Val Phe Ser Cys
290                 295                 300 tcc gtg atg cat gag gct ctg cac aac cac tac aca cag aag agc ctc        960
Ser Val Met His Glu Ala Leu His Asn His Tyr Thr Gln Lys Ser Leu
305                 310                 315                 320 tcc ctg tct ccg                                                        972
Ser Leu Ser Pro <210> SEQ ID NO 13
<211> LENGTH: 324
<212> TYPE: PRT
<213> ORGANISM: Artificial Sequence
<220> FEATURE:
<223> OTHER INFORMATION: Synthetic Construct

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Ser Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270
```

```
Thr Pro Pro Met Leu Asp Ser Asp Gly Ser Phe Phe Leu Tyr Ser Lys
            275                 280                 285

Leu Thr Val Asp Lys Ser Arg Trp Gln Glu Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro

<210> SEQ ID NO 14
<211> LENGTH: 107
<212> TYPE: PRT
<213> ORGANISM: Artificial Sequence
<220> FEATURE:
<223> OTHER INFORMATION: Artificially synthesized antibody  CL sequence

<400> SEQUENCE: 14

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 15
<211> LENGTH: 267
<212> TYPE: PRT
<213> ORGANISM: Homo sapiens

<400> SEQUENCE: 15

Ala Glu Ser His Leu Ser Leu Leu Tyr His Leu Thr Ala Val Ser Ser
1               5                   10                  15

Pro Ala Pro Gly Thr Pro Ala Phe Trp Val Ser Gly Trp Leu Gly Pro
            20                  25                  30

Gln Gln Tyr Leu Ser Tyr Asn Ser Leu Arg Gly Glu Ala Glu Pro Cys
        35                  40                  45

Gly Ala Trp Val Trp Glu Asn Gln Val Ser Trp Tyr Trp Glu Lys Glu
    50                  55                  60

Thr Thr Asp Leu Arg Ile Lys Glu Lys Leu Phe Leu Glu Ala Phe Lys
65                  70                  75                  80

Ala Leu Gly Gly Lys Gly Pro Tyr Thr Leu Gln Gly Leu Leu Gly Cys
                85                  90                  95

Glu Leu Gly Pro Asp Asn Thr Ser Val Pro Thr Ala Lys Phe Ala Leu
            100                 105                 110

Asn Gly Glu Glu Phe Met Asn Phe Asp Leu Lys Gln Gly Thr Trp Gly
        115                 120                 125

Gly Asp Trp Pro Glu Ala Leu Ala Ile Ser Gln Arg Trp Gln Gln Gln
    130                 135                 140

Asp Lys Ala Ala Asn Lys Glu Leu Thr Phe Leu Leu Phe Ser Cys Pro
145                 150                 155                 160
```

```
His Arg Leu Arg Glu His Leu Glu Arg Gly Arg Gly Asn Leu Glu Trp
                165                 170                 175

Lys Glu Pro Pro Ser Met Arg Leu Lys Ala Arg Pro Ser Ser Pro Gly
            180                 185                 190

Phe Ser Val Leu Thr Cys Ser Ala Phe Ser Phe Tyr Pro Pro Glu Leu
        195                 200                 205

Gln Leu Arg Phe Leu Arg Asn Gly Leu Ala Ala Gly Thr Gly Gln Gly
        210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
                245                 250                 255

Ala Gly Leu Ala Gln Pro Leu Arg Val Glu Leu
                260                 265

<210> SEQ ID NO 16
<211> LENGTH: 99
<212> TYPE: PRT
<213> ORGANISM: Homo sapiens

<400> SEQUENCE: 16

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
                20                  25                  30

Ser Asp Ile Glu Val Asp Leu Leu Lys Asn Gly Glu Arg Ile Glu Lys
            35                  40                  45

Val Glu His Ser Asp Leu Ser Phe Ser Lys Asp Trp Ser Phe Tyr Leu
        50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met
```

ANTIBODY CONSTANT REGION VARIANT

CROSS-REFERENCE TO RELATED APPLICATIONS

This application is a continuation of U.S. application Ser. No. 13/257,112, having a 371 (c) date of Nov. 22, 2011, which is the National Stage of International Application Serial No. PCT/JP2010/054769, filed on Mar. 19, 2010, which claims priority to Japanese Application Serial No. 2009-068630, filed on Mar. 19, 2009.

TECHNICAL FIELD

The present invention relates to antibody constant regions with an altered amino acid sequence, and antibodies comprising these constant regions.

BACKGROUND

Antibodies are drawing attention as pharmaceuticals as they are highly stable in plasma (blood) and have few side effects. Of these, a number of IgG-type antibody pharmaceuticals are available on the market and many antibody pharmaceuticals are currently under development (Non-patent Documents 1 and 2).

Almost all antibody pharmaceuticals currently available on the market are of the IgG1 subclass. IgG1 type antibodies are expected be useful as anti-cancer antibody pharmaceuticals since they can bind to Fcγ receptor and exert ADCC activity. However, when it comes to antibody pharmaceuticals intended for neutralizing biological activity of an antigen, the binding of the Fc domain to Fcγ receptor, which is important for effector functions such as ADCC, can cause unnecessary side effects, and thus it is preferable to eliminate such binding activity (Non-patent Document 3). Furthermore, since Fcγ receptor is expressed on antigen-presenting cells, molecules that bind to Fcγ receptor tend to be presented as antigens. It has been reported that immunogenicity is and can be enhanced by linking a protein or peptide to the Fc domain of IgG1 (Non-patent Document 4 and Patent Document 1). Interaction between the antibody Fc domain and Fcγ receptor is thought to be a cause of the serious side effects encountered in phase-I clinical trials of TGN1412 (Non-patent Document 5). Thus, binding to Fcγ receptor is considered unfavorable in antibody pharmaceuticals intended for neutralizing the biological activity of an antigen from the perspective of side effects and immunogenicity.

A method for impairing the binding to Fcγ receptor is to alter the subtype of the IgG antibody from IgG1 to IgG2 or IgG4; however, this method cannot completely inhibit the binding (Non-patent Document 6). One of the methods reported for completely inhibiting the binding to Fcγ receptor is to artificially alter the Fc domain. For example, the effector functions of anti-CD3 antibodies and anti-CD4 antibodies cause side effects. Thus, amino acids that are not present in the wild type sequence were introduced into the Fcγ-receptor-binding domain of Fc (Non-patent Documents 3 and 7), and clinical trials are currently being conducted to assess anti-CD3 antibodies and anti-CD4 antibodies that have a mutated Fc domain and do not bind to Fcγ receptor (Non-patent Documents 5 and 8). Alternatively, Fcγ receptor-nonbinding antibodies can be prepared by altering the FcγR-binding sites of IgG1 (positions 233, 234, 235, 236, 327, 330, and 331 in the EU numbering; hereafter abbreviated as position X (EU numbering)) to an IgG2 or IgG4 sequence (Non-patent Document 9 and Patent Document 2). However, these molecules contain new non-native peptide sequences of nine to twelve amino acids, which may have a potential to become a T-cell epitope peptide and thus pose an immunogenicity risk. There is no previous report on Fcγ receptor-nonbinding antibodies that have overcome these problems.

Meanwhile, physicochemical properties of antibody proteins, in particular, homogeneity and stability, are very crucial in the development of antibody pharmaceuticals. For the IgG2 subtype, heterogeneity caused by disulfide bonds in the hinge region has been reported (Non-patent Documents 10, 16, 17, and 18 and Patent Document 3). It is not easy to manufacture them as a pharmaceutical in a large scale while maintaining differences of desired product/related substance-related heterogeneity between productions. Thus, single substances are desirable as much as possible for antibody molecules developed as pharmaceuticals. In the present invention, differences in heterogeneity among productions can be understood, for example, as differences in heterogeneity among production lots. Heterogeneity in the production lots can be evaluated quantitatively by determining the diversity of molecular weight and structure of the produced antibody molecules.

IgG2 and IgG4 are unstable under acidic conditions. IgG type antibodies are in general exposed to acidic conditions in the purification process using Protein A and the virus inactivation process. Thus, attention is needed regarding the stability of IgG2 and IgG4 during these processes, and it is preferable that antibody molecules developed as pharmaceuticals are also stable under acidic conditions. Natural IgG2 and IgG4, and Fcγ receptor-nonbinding antibodies derived from IgG2 or IgG4 (Non-patent Documents 6 and 7 and Patent Document 2) have such problems. It is desirable to solve these problems when developing antibodies into pharmaceuticals.

IgG1-type antibodies are relatively stable under acidic conditions, and the degree of heterogeneity caused by disulfide bonds in the hinge region is also lower in this type of antibodies. However, IgG1-type antibodies are reported to undergo non-enzymatic peptide bond cleavage in the hinge region in solutions when they are stored as formulations, and as a result, Fab fragments are generated as impurities (Non-patent Document 11). It is desirable to overcome the generation of impurities when developing antibodies into pharmaceuticals.

Furthermore, for heterogeneity of the C-terminal sequence of an antibody, deletion of C-terminal amino acid lysine residue, and amidation of the C-terminal amino group due to deletion of both of the two C-terminal amino acids, glycine and lysine, have been reported (Non-patent Document 12). It is preferable to eliminate such heterogeneity when developing antibodies into pharmaceuticals.

The constant region of an antibody pharmaceutical aimed at neutralizing an antigen preferably has a sequence that overcomes all the problems described above. However, a constant region that meets all the requirements has not been reported.

A preferred form of antibody pharmaceutical administration in chronic autoimmune diseases and such is thought to be subcutaneous formulation. Low-cost, convenient antibody pharmaceuticals that can be administered subcutaneously at longer intervals can be provided by increasing the half-life of an antibody in the plasma to prolong its therapeutic effect and thereby reduce the amount of protein administered, and by conferring the antibody with high stability so that high concentration formulations can be prepared.

In general, subcutaneous formulations need to be high-concentration formulations. From the perspective of stability and such, the concentration limit of IgG-type antibody formulations is generally thought to be about 100 mg/ml (Non-patent Document 13). Thus, it was a challenge to secure stability at high concentrations. However, there has been no report published on the improvement of the stability of IgG at high concentrations by introducing amino acid substitutions into its constant region. A method for prolonging the antibody half-life in plasma has been reported and it substitutes amino acids in the constant region (Non-patent Documents 14 and 15); however, introduction of non-native sequences into the constant region is unpreferable from the perspective of immunogenicity risk.

As described above, when the purpose of an antibody pharmaceutical is to neutralize an antigen, it is preferable that all of the problems described above have been overcome with regard to its constant-region sequence. However, a constant region that meets all the requirements has not been reported. Thus, there is a demand for antibody constant regions that have overcome the problems described above.

Documents of related prior arts for the present invention are described below.

PRIOR ART DOCUMENTS

Patent Documents

[Patent Document 1] US 20050261229 A1
[Patent Document 2] WO 99/58572
[Patent Document 3] US 2006/0194280

Non-Patent Documents

[Non-patent Document 1] Janice M Reichert, Clark J Rosensweig, Laura B Faden & Matthew C Dewitz. Monoclonal antibody successes in the clinic. Nature Biotechnology (2005) 23, 1073-1078
[Non-patent Document 2] Pavlou A K, Belsey M J. The therapeutic antibodies market to 2008. Eur. J. Pharm. Biopharm. 2005 April; 59(3):389-96
[Non-patent Document 3] Reddy M P, Kinney C A, Chaikin M A, Payne A, Fishman-Lobell J, Tsui P, Dal Monte P R, Doyle M L, Brigham-Burke M R, Anderson D, Reff M, Newman R, Hanna N, Sweet R W, Truneh A. Elimination of Fc receptor-dependent effector functions of a modified IgG4 monoclonal antibody to human CD4. J. Immunol. 2000 Feb. 15; 164(4):1925-33
[Non-patent Document 4] Guyre P M, Graziano R F, Goldstein J, Wallace P K, Morganelli P M, Wardwell K, Howell A L. Increased potency of Fc-receptor-targeted antigens. Cancer Immunol. Immunother. 1997 November-December; 45(3-4):146-8
[Non-patent Document 5] Strand V, Kimberly R, Isaacs J D. Biologic therapies in rheumatology: lessons learned, future directions. Nat. Rev. Drug Discov. 2007 Jan.; 6(1):75-92
[Non-patent Document 6] Gessner J E, Heiken H, Tamm A, Schmidt R E. The IgG Fc receptor family. Ann. Hematol. 1998 June; 76(6):231-48
[Non-patent Document 7] Cole M S, Anasetti C, Tso J Y. Human IgG2 variants of chimeric anti-CD3 are nonmitogenic to T cells. J. Immunol. 1997 Oct. 1; 159(7):3613-21
[Non-patent Document 8] Chau L A, Tso J Y, Melrose J, Madrenas J. HuM291(Nuvion), a humanized Fc receptor-nonbinding antibody against CD3, anergizes peripheral blood T cells as partial agonist of the T cell receptor. Transplantation 2001 Apr. 15; 71(7):941-50
[Non-patent Document 9] Armour K L, Clark M R, Hadley A G, Williamson L M. Recombinant human IgG molecules lacking Fcgamma receptor I binding and monocyte triggering activities. Eur. J. Immunol. 1999 Aug.; 29(8):2613-24
[Non-patent Document 10] Chu G C, Chelius D, Xiao G, Khor H K, Coulibaly S, Bondarenko P V. Accumulation of Succinimide in a Recombinant Monoclonal Antibody in Mildly Acidic Buffers Under Elevated Temperatures. Pharm. Res. 2007 Mar. 24; 24(6):1145-56
[Non-patent Document 11] A J Cordoba, B J Shyong, D Breen, R J Harris. Nonenzymatic hinge region fragmentation of antibodies in solution. J. Chromatogr. B. Anal. Technol. Biomed. Life Sci. (2005) 818, 115-121
[Non-patent Document 12] Johnson K A, Paisley-Flango K, Tangarone B S, Porter T J, Rouse J C. Cation exchange-C and mass spectrometry reveal C-terminal amidation of an IgG1 heavy chain. Anal. Biochem. 2007 Jan. 1; 360(1):75-83
[Non-patent Document 13] Shire S J, Shahrokh Z, Liu J. Challenges in the development of high protein concentration formulations. J. Pharm. Sci. 2004 June; 93(6):1390-402
[Non-patent Document 14] Hinton P R, Xiong J M, Johlfs M G, Tang M T, Keller S, Tsurushita N. An engineered human IgG1 antibody with longer serum half-life. J. Immunol. 2006 Jan. 1; 176(1):346-56
[Non-patent Document 15] Ghetie V, Popov S, Borvak J, Radu C, Matesoi D, Medesan C, Ober R J, Ward E S. Increasing the serum persistence of an IgG fragment by random mutagenesis. Nat. Biotechnol. 1997 Jul.; 15(7):637-40
[Non-patent Document 16] Wypych J, Li M, Guo A, Zhang Z, Martinez T, Allen M J, Fodor S, Kelner D N, Flynn G C, Liu Y D, Bondarenko P V, Ricci M S, Dillon T M, Balland A. Human IgG2 antibodies display disulfide-mediated structural isoforms. J Biol Chem. 2008 Jun. 6; 283(23):16194-205
[Non-patent Document 17] Dillon T M, Ricci M S, Vezina C, Flynn G C, Liu Y D, Rehder D S, Plant M, Henkle B, Li Y, Deechongkit S, Varnum B, Wypych J, Balland A, Bondarenko P V. Structural and functional characterization of disulfide isoforms of the human IgG2 subclass. J Biol Chem. 2008 Jun. 6; 283(23):16206-15
[Non-patent Document 18] Martinez T, Guo A, Allen M J, Han M, Pace D, Jones J, Gillespie R, Ketchem R R, Zhang Y, Balland A. Disulfide connectivity of human immunoglobulin G2 structural isoforms. Biochemistry 2008 Jul. 15; 47(28):7496-508

SUMMARY

Problems to be Solved by the Invention

The present invention was achieved in view of the above circumstances. Specifically, an objective of the present invention is to provide constant regions that can confer antibodies with properties preferable for pharmaceuticals, and antibodies comprising these constant regions and variable regions.

Means for Solving the Problems

The present inventors conducted dedicated studies to generate antibody constant regions that have been improved by modifying their amino acid sequences, which have improved physicochemical properties (stability and homogeneity), immunogenicity, safety, and pharmacokinetics. As a result, the present inventors successfully produced antibody constant regions with reduced heterogeneity caused by disulfide bonds in the hinge region, reduced heterogeneity caused by the H-chain C terminus, and increased stability.

The present invention relates to antibody constant regions that are superior in terms of safety, immunogenicity risk, physicochemical properties (stability and homogeneity), and pharmacokinetics through improvement by amino acid alterations; antibodies comprising such antibody constant regions; pharmaceutical compositions comprising such antibodies; and methods for producing them. More specifically, the present invention provides:

[1] an antibody constant region comprising an amino acid sequence in which Cys at position 102 (position 219 (EU numbering)) and Cys at position 103 (position 220 (EU numbering)) in the amino acid sequence of SEQ ID NO: 8 (IgG2 constant region) are other amino acids;

[2] the antibody constant region of [1], wherein His at position 147 (position 268 (EU numbering)), Arg at position 234 (position 355 (EU numbering)), and Gln at position 298 (position 419 (EU numbering)) are also other amino acids;

[3] the antibody constant region of [1], wherein Cys at position 102 and Cys at position 103 are Ser;

[4] the antibody constant region of [2], wherein His at position 147 is Gln, Arg at position 234 is Gln, and Gln at position 298 is Glu;

[5] the antibody constant region of any one of [1] to [4], which comprises an amino acid sequence also comprising deletions of Gly at position 325 (position 446 (EU numbering)) and Lys at position 326 (position 447 (EU numbering));

[6] an antibody comprising the constant region of any one of (1) to (5) below:

(1) an antibody constant region comprising an amino acid sequence in which Cys at position 102 (position 219 (EU numbering)) and Cys at position 103 (position 220 (EU numbering)) in the amino acid sequence of SEQ ID NO: 8 (IgG2 constant region) are other amino acids;

(2) the antibody constant region of (1), wherein Cys at position 102 and Cys at position 103 are Ser;

(3) the antibody constant region of (1) or (2), wherein His at position 147 (position 268 (EU numbering)), Arg at position 234 (position 355 (EU numbering)), and Gln at position 298 (position 419 (EU numbering)) are also other amino acids;

(4) the antibody constant region of (3), wherein His at position 147 is Gln, Arg at position 234 is Gln, and Gln at position 298 is Glu; and (5) the antibody constant region of any one of (1) to (4), which comprises an amino acid sequence also comprising deletions of Gly at position 325 (position 446 (EU numbering)) and Lys at position 326 (position 447 (EU numbering)); and

[7] a pharmaceutical composition comprising the antibody of [6].

Effects of the Invention

The present invention provides constant regions that can confer to antibodies properties desirable for pharmaceutical agents. By means of amino acid sequence alterations, the constant regions of the present invention can improve the following antibody properties to conditions favorable for pharmaceutical agents.

Decrease in Antibody Heterogeneity:

Polypeptides obtainable by expressing a DNA encoding a certain amino acid sequence should theoretically be homogeneous polypeptide molecules consisting of the same amino acid sequence. However, in practice, when a DNA encoding an antibody is expressed in suitable hosts, heterogeneous polypeptides with different structures may be formed due to various factors. In the production of antibodies, an antibody population comprising many heterogeneous polypeptides can be referred to as having high heterogeneity. The constant regions of the present invention have the causes of heterogeneity removed by amino acid sequence alteration. Therefore, constructing antibodies using the constant regions of the present invention enables production of antibodies with low heterogeneity. Specifically, by introducing alterations provided by the present invention into heavy chain constant regions of antibodies, the homogeneity of the antibodies can be maintained at a high level. Suppressing the antibody heterogeneity to a low level means ameliorating the heterogeneity and this is an important objective in maintaining the quality of pharmaceuticals. Therefore, the constant regions of the present invention contribute to the maintenance of the quality of antibody-containing pharmaceuticals.

Improvement of Pharmacokinetics:

In a preferred embodiment, the present invention contributes to improvement of antibody pharmacokinetics. Specifically, when specific amino acid residues are altered in an antibody constant region of the present invention, blood concentration of the antibody composed of this constant region is maintained for a longer time than an antibody without amino acid sequence alterations. Maintaining blood concentration for as long a time as possible means that, when an antibody is administered as a pharmaceutical, its therapeutic effect can be maintained for a long time with a smaller amount of antibody. Alternatively, the antibody can be administered with wider intervals and smaller number of administrations.

DETAILED DESCRIPTION

Figure 1:
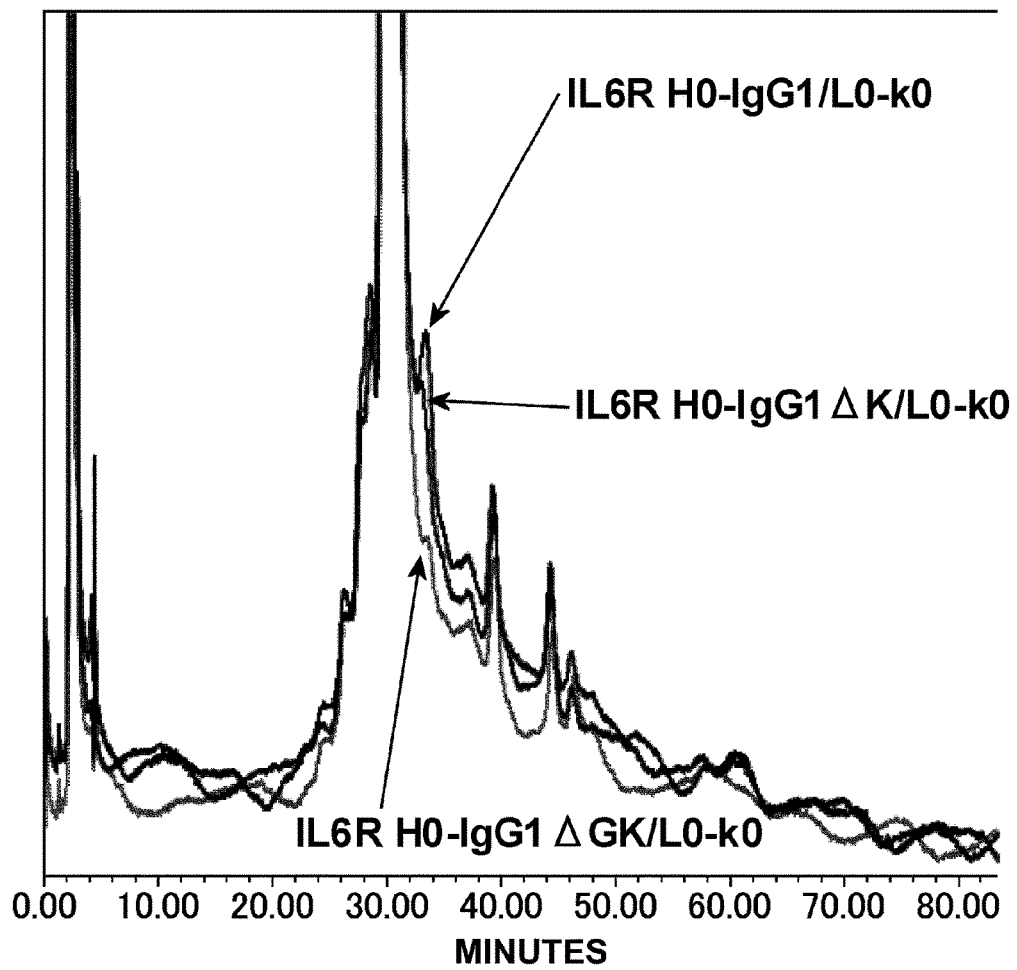
FIG. 1 depicts the results of performing cation exchange chromatography on antibodies IL6R H0-IgG1/L0-k0, IL6R H0-IgG1ΔK/L0-k0, and IL6R H0-IgG1ΔGK/L0-k0 to evaluate the heterogeneity derived from the C terminus. In the figure, the vertical axis shows absorbance at 280 nm and the horizontal axis shows elution time (minutes).

The present invention provides antibody constant regions with altered amino acid sequence; antibodies comprising such constant regions; pharmaceutical compositions comprising such antibodies; and methods for producing them.

Herein, the antibody constant region refers to IgG1, IgG2, or IgG4 type constant region. The antibody constant region is preferably a human antibody constant region, and IgG2 constant region is preferred in particular. The amino acid sequences of human IgG1, IgG2, and IgG4 constant regions are known.
Human IgG1 constant region, SEQ ID NO: 7
Human IgG2 constant region, SEQ ID NO: 8
Human IgG4 constant region, SEQ ID NO: 9

Regarding the human IgG1, IgG2, and IgG4 constant regions of the present invention, a number of allotype sequences arising from genetic polymorphism are described in the Sequences of Proteins of Immunological Interest, NIH Publication No. 91-3242, and all of them are acceptable in the present invention.

The antibody constant regions of the present invention can include additional alterations in addition to amino acid sequence alterations (modifications) introduced based on the present invention. For example, additional alterations can be selected from amino acid substitution, deletion, or modification, or their combinations. Specifically, constant regions containing alterations such as the following in their amino acid sequence are all included in the present invention.
  Alterations based on the present invention introduced into the amino acid sequence of SEQ ID NO: 8 (human IgG2 constant region).
  Alterations based on the present invention introduced into an altered amino acid sequence of SEQ ID NO: 8 (human IgG2 constant region).
  Alterations based on the present invention introduced into the amino acid sequence of SEQ ID NO: 8 (human IgG2 constant region) with additional alterations.

Amino acid modifications of the present invention include post-translational modifications. Specific examples of post-translational modifications can include addition or deletion of sugar chains. For example, in the IgG2 constant region consisting of the amino acid sequence of SEQ ID NO: 8, the amino acid residue at position 297 according to the EU numbering may be modified by sugar chains. The sugar chain structures involved in the modification are not limited.

In general, antibodies expressed in eukaryotic cells include sugar chain modifications in the constant regions. Therefore, antibodies expressed in cells such as the following are usually modified by some kind of sugar chain:
  antibody-producing cells of mammals; and
  eukaryotic cells transformed with an expression vector containing an antibody-encoding DNA.

Eukaryotic cells indicated herein include yeast and animal cells. For example, CHO cells and HEK293H cells are representative animal cells for transformation using expression vectors containing an antibody-encoding DNA. Those without sugar chain modification at this position are also included in the constant regions of the present invention. Antibodies in which the constant regions are not modified by sugar chains can be obtained by expressing the antibody-encoding gene in prokaryotic cells such as *Escherichia coli*.

<IgG2 Having Altered Amino Acids>

The present invention provides IgG2 constant regions with an improved stability under acidic conditions.

More specifically, the present invention provides IgG2 constant regions in which an amino acid residue other than Met has been substituted for Met at position 276 (position 397 (EU numbering)) in the amino acid sequence of SEQ ID NO: 8. The type of amino acid residue after substitution can be any amino acid residue other than Met. In the present invention, a preferred amino acid residue is Val. The antibody stability under acidic conditions can be improved by substituting another amino acid for Met at position 276 (position 397 (EU numbering)) in the amino acid sequence of SEQ ID NO: 8.

The constant regions provided by the present invention, which have an improved stability under acidic conditions, may also have other amino acid substitutions, deletions, additions, and/or insertions, as long as they have at least the amino acid substitution described above.

The present invention provides constant regions with reduced heterogeneity of hinge region.

More specifically, the present invention provides IgG2 constant regions in which other amino acids have been substituted for Cys at position 102 (position 219 (EU numbering)) and Cys at position 103 (position 220 (EU numbering)) in the amino acid sequence of SEQ ID NO: 8. The type of other amino acids is not particularly limited; however, substitutions of Ser for Cys at position 102 (position 219 (EU numbering)) and Cys at position 103 (position 220 (EU numbering)) are preferred.

These substitutions can reduce the heterogeneity arising from the hinge region of IgG2.

The constant regions provided by the present invention, which have reduced heterogeneity, may also have other amino acid substitutions, deletions, additions, and/or insertions, as long as they have at least the amino acid substitution described above.

The present invention also provides constant regions with reduced Fcγ receptor-binding activity.

More specifically, the present invention also provides constant regions comprising an amino acid sequence in which Ala at position 209 (position 330 (EU numbering)), Pro at position 210 (position 331 (EU numbering)), and/or Thr at position 218 (position 339 (EU numbering)) of the amino acid sequence of SEQ ID NO: 8 are Ser, Ser, and Ala, respectively. The substitutions for Ala at position 209 (position 330 (EU numbering)) and for Pro at position 210 (position 331 (EU numbering)) have already been reported to enable the impairment of the Fcγ receptor binding (Eur. J. Immunol. 1999 Aug.; 29(8):2613-24). From the perspective of immunogenicity risk, however, these alterations are not preferred because they result in generation of non-human derived peptides that can become T-cell epitopes. However, the Fcγ receptor binding of IgG2 can be reduced by substituting Ala for Thr at position 218 (position 339 (EU numbering)) at the same time, and the 9-12 amino acid peptides which can become T-cell epitopes are derived from human only.

In the constant regions of the present invention, at least one of the three types of amino acid substitutions described above is another amino acid, but preferably all three types of the amino acids described above are other amino acids. In a preferred embodiment, the constant regions of the present invention include constant regions comprising an amino acid sequence in which Ala at position 209 (position 330 (EU numbering)), Pro at position 210 (position 331 (EU numbering)), and Thr at position 218 (position 339 (EU numbering)) in the amino acid sequence of SEQ ID NO: 8 are Ser, Ser, and Ala, respectively.

The constant regions provided by the present invention, which have reduced Fcγ receptor-binding activity, may also have other amino acid substitutions, deletions, additions, and/or insertions, as long as they have at least the amino acid substitutions described above.

The present invention provides constant regions with reduced C-terminal heterogeneity.

More specifically, the present invention provides constant regions comprising an amino acid sequence in which Gly at position 325 (position 446 (EU numbering)) and Lys at position 326 (position 447 (EU numbering)) have been deleted in the amino acid sequence of SEQ ID NO: 8. The heterogeneity derived from the C terminus of antibody H chain can be reduced only when both of the amino acids are deleted.

The constant regions provided by the present invention, which have reduced C-terminal heterogeneity, may also have other amino acid substitutions, deletions, additions, and/or insertions, as long as they have at least the amino acid deletions described above.

The present invention further provides constant regions with improved pharmacokinetics.

Specifically, the present invention provides IgG2 constant regions in which His at position 147 (position 268 (EU numbering)), Arg at position 234 (position 355 (EU numbering)), and Gln at position 298 (position 419 (EU numbering)) in the amino acid sequence of SEQ ID NO: 8 are other amino acids. These amino acid substitutions enable improvement of antibody pharmacokinetics. The type of amino acid after substitution is not particularly limited; however, His at position 147 (position 268 (EU numbering)) is preferably Gln, Arg at position 234 (position 355 (EU numbering)) is preferably Gln, and Gln at position 298 (position 419 (EU numbering)) is preferably Glu. The constant regions of the present invention include constant regions comprising at least one of the three types of the amino acid substitutions described above; however, the constant regions preferably comprise all three types of the amino acid substitutions described above.

Furthermore, in the present invention, the following antibody can be presented as a preferred embodiment of antibodies with reduced heterogeneity of the hinge region and/or improved pharmacokinetics:

Antibody in which Cys at position 102, Cys at position 103, His at position 147, Arg at position 234, and Gln at position 298 in the antibody having the IgG2 constant region consisting of the amino acid sequence of SEQ ID NO: 8 are other amino acids.

The other amino acids are not particularly limited, but preferably, Cys at position 102 (position 219 (EU numbering)) is Ser, Cys at position 103 (position 220 (EU numbering)) is Ser, His at position 147 (position 268 (EU numbering)) is Gln, Arg at position 234 (position 355 (EU numbering)) is Gln, and Gln at position 298 (position 419 (EU numbering)) is Glu.

In another preferred embodiment, constant regions of the present invention include IgG2 constant regions resulting from the deletion of Gly at position 325 and Lys at position 326 in the above-described constant regions to reduce C-terminal heterogeneity. Examples of such antibodies include those having constant regions consisting of the amino acid sequence of SEQ ID NO: 13 (M82).

These antibody constant regions have been optimized to have reduced Fcγ receptor binding activity, reduced immunogenicity risk, improved stability under acidic conditions, reduced heterogeneity, improved pharmacokinetics, and/or higher stability in preparations in comparison with the IgG1 constant region.

Furthermore, the present invention provides antibodies comprising any one of the antibody constant regions mentioned above. More specifically, the present invention relates to antibodies having the constant region of any one of (1) to (5) below:

(1) an antibody constant region having an amino acid sequence in which Cys at position 102 (position 219 (EU numbering)) and Cys at position 103 (position 220 (EU numbering)) in the amino acid sequence of SEQ ID NO: 8 (IgG2 constant region) are other amino acids;
(2) the antibody constant region of (1), wherein Cys at position 102 and Cys at position 103 are Ser;
(3) the antibody constant region of (1) or (2), wherein His at position 147 (position 268 (EU numbering)), Arg at position 234 (position 355 (EU numbering)), and Gln at position 298 (position 419 (EU numbering)) are also other amino acids;
(4) the antibody constant region of (3), wherein His at position 147 is Gln, Arg at position 234 is Gln, and Gln at position 298 is Glu; and
(5) the antibody constant region of any one of (1) to (4), having an amino acid sequence also containing deletions of Gly at position 325 (position 446 (EU numbering)) and Lys at position 326 (position 447 (EU numbering)).

The type of antigen, the origin of antibody, and such are not limited for an antibody of the present invention; as long as it has an antibody constant region mentioned above, it may be any antibody.

The antibodies of the present invention also include modified products of antibodies comprising any of the amino acid substitutions described above. The origin of antibodies is not particularly limited. The antibodies include human, mouse, rat, and rabbit antibodies. The antibodies of the present invention may be chimeric, humanized, fully humanized antibodies, or such. In a preferred embodiment, the antibodies of the present invention are humanized antibodies.

Antibody molecules of the present invention usually include H chains and L chains. H chains may include variable regions in addition to constant regions. Variable regions may include variable portions derived not only from humans, but also from non-human animal species. Furthermore, CDR can be transplanted from variable portions derived from non-human species such as mice to humanize the variable portions. Antibody molecules composed of H chains and L chains may be oligomers. Specifically, they may be monomers, dimers, or larger oligomers. Alternatively, the antibody constant regions described above and/or antibody molecules comprising an antibody constant region described above can be linked as a form of Fc fusion molecule to antibody-like binding molecules (scaffold molecules), bioactive peptides, binding peptides, or such.

The antibodies of the present invention also include modification products of an antibody comprising any one of the constant regions described above.

Such antibody modification products include, for example, antibodies linked with various molecules such as polyethylene glycol (PEG) and cytotoxic substances. Such antibody modification products can be obtained by chemically modifying antibodies of the present invention. Methods for modifying antibodies are already established in this field.

The antibodies of the present invention may also be bispecific antibodies. "Bispecific antibody" refers to an antibody that has in a single molecule variable regions that recognize different epitopes. The epitopes may be present in a single molecule or in separate molecules.

The antibody constant regions described above can be used as a constant region in an antibody against an arbitrary antigen. The antigen is not particularly limited.

The antibodies of the present invention can be obtained by, for example, the following methods. In one embodiment to obtain antibodies of the present invention, one or more amino acid residues are first deleted or replaced with amino acids of interest in the constant region. Methods for substituting amino acids of interest for one or more amino acid residues include, for example, site-directed mutagenesis (Hashimoto-Gotoh, T., Mizuno, T., Ogasahara, Y., and Nakagawa, M. An oligodeoxyribonucleotide-directed dual amber method for site-directed mutagenesis. Gene (1995) 152, 271-275; Zoller, M. J., and Smith, M. Oligonucleotide-directed mutagenesis of DNA fragments cloned into M13 vectors. Methods Enzymol. (1983) 100, 468-500; Kramer, W., Drutsa, V., Jansen, H. W., Kramer, B., Pflugfelder, M., and Fritz, H. J. The gapped duplex DNA approach to oligonucleotide-directed mutation construction. Nucleic Acids Res. (1984) 12, 9441-9456; Kramer W., and Fritz H. J. Oligonucleotide-directed construction of mutations via gapped duplex DNA Methods. Enzymol. (1987) 154, 350-367; Kunkel, T. A. Rapid and efficient site-specific mutagenesis without phenotypic selection. Proc. Natl. Acad. Sci. USA (1985) 82, 488-492). These methods can be used to substitute other amino acids for target amino acids in the constant region of an antibody.

In another embodiment to obtain antibodies, an antibody that binds to an antigen of interest is first prepared by methods known to those skilled in the art. When the prepared antibody is derived from a non-human animal, it can be humanized. The binding activity of the antibody can be determined by known methods. Next, one or more amino acid residues in the constant region of the antibody are deleted or replaced with amino acids of interest.

More specifically, the present invention relates to methods for producing antibodies, which comprise the steps of:
(a) expressing a DNA encoding an H chain in which one or more amino acid residues in the constant region are deleted or replaced with amino acids of interest, and a DNA encoding an L chain; and
(b) collecting the expression products of step (a).

The first step of the production methods of the present invention is expressing a DNA encoding an antibody H chain in which one or more amino acid residues in the constant region are deleted or replaced with amino acids of interest, and a DNA encoding an antibody L chain.

A DNA encoding an H chain in which one or more amino acid residues in the constant region are deleted or replaced with amino acids of interest can be prepared, for example, by obtaining a DNA encoding the constant region of a wild type H chain, and introducing an appropriate substitution so that a codon encoding a particular amino acid in the constant region encodes an amino acid of interest.

Alternatively, a DNA encoding an H chain in which one or more amino acid residues in the constant region are deleted or replaced with amino acids of interest can also be prepared by designing and then chemically synthesizing a DNA encoding a protein in which one or more amino acid residues in the constant region of the wild type H chain are deleted or replaced with amino acids of interest.

The type of amino acid substitution includes the substitutions described herein, but is not limited thereto.

Alternatively, a DNA encoding an H chain in which one or more amino acid residues in the constant region are deleted or replaced with amino acids of interest can also be prepared as a combination of partial DNAs. Such combinations of partial DNAs include, for example, the combination of a DNA encoding a variable region and a DNA encoding a constant region, and the combination of a DNA encoding an Fab region and a DNA encoding an Fc region, but are not limited thereto. A DNA encoding an L chain can also be prepared as a combination of partial DNAs.

Methods for expressing the above-described DNAs include the methods described below. For example, an H-chain expression vector is constructed by inserting a DNA encoding an H-chain variable region into an expression vector along with a DNA encoding an H-chain constant region. Likewise, an L-chain expression vector is constructed by inserting a DNA encoding an L-chain variable region into an expression vector along with a DNA encoding an L-chain constant region. Alternatively, these H and L chain genes may be inserted into a single vector. Expression vectors include, for example, SV40 virus-based vectors, EB virus-based vectors, and BPV (papilloma virus)-based vectors, but are not limited thereto.

Host cells are co-transformed with an antibody expression vector constructed by the methods described above. Such host cells include the above-described cells such as CHO (Chinese hamster ovary) cells as well as microorganisms such as *E. coli*, yeast, and *Bacillus subtilis*, and plants and animals (Nature Biotechnology (2007) 25, 563-565; Nature Biotechnology (1998) 16, 773-777; Biochemical and Biophysical Research Communications (1999) 255, 444-450; Nature Biotechnology (2005) 23, 1159-1169; Journal of Virology (2001) 75, 2803-2809; Biochemical and Biophysical Research Communications (2003) 308, 94-100). The transformation can be preferably achieved by using electroporation, the lipofectin method (R. W. Malone et al., Proc. Natl. Acad. Sci. USA (1989) 86, 6077; P. L. Feigner et al., Proc. Natl. Acad. Sci. USA (1987) 84, 7413), calcium phosphate method (F. L. Graham & A. J. van der Eb, Virology (1973) 52, 456-467), DEAE-Dextran method, and the like.

In the next step of antibody production, the expression products obtained in step (a) are collected. The expression products can be collected, for example, by culturing the transformants and then separating the products from the transformed cells or culture media. Separation and purification of antibodies can be achieved by an appropriate combination of methods such as centrifugation, ammonium sulfate fractionation, salting out, ultrafiltration, columns of 1 q, FcRn, Protein A, and Protein G, affinity chromatography, ion exchange chromatography, and gel filtration chromatography.

The present invention provides antibodies produced as described above. More specifically, the present invention relates to antibodies that can be produced by the following steps:
(a) expressing in host cells, DNAs encoding an antibody heavy chain which comprises variable and constant regions, and a light chain; and
(b) collecting the antibodies expressed in (a).

A characteristic of the above-mentioned method is that the amino acid sequence of the heavy chain constant region is an above-mentioned constant region provided by the present invention. In a preferred embodiment of the present invention, the constant region consists of for example, the amino acid sequence of SEQ ID NO: 13. Linking a DNA consisting of the nucleotide sequence (SEQ ID NO: 12) encoding this amino acid sequence with a DNA encoding the heavy chain variable region can produce a DNA encoding the antibody heavy chain. The amino acid sequence indicated in SEQ ID NO: 6 is, for example, the full-length sequence of the heavy chain of a humanized antibody which recognizes the IL6 receptor. The constant region (120-443) in the amino acid sequence of SEQ ID NO: 6 is composed of the amino acid sequence of SEQ ID NO: 13. Meanwhile, 1-119 in SEQ ID NO: 6 correspond to the variable region.

As the light chains constituting the antibodies of the present invention, one may combine, for example, L0-k0 (SEQ ID NO: 2). The DNAs encoding the heavy and light chains used for obtaining the antibodies of the present invention can be obtained, for example, by synthesizing DNAs encoding these amino acid sequences. DNAs encoding the heavy and light chains can be further attached with an additional sequence such as a signal sequence when necessary and incorporated into suitable expression vectors. The vectors may include promoters and enhancers for expressing DNAs encoding antibodies incorporated into appropriate hosts.

Furthermore, the present invention relates to antibodies composed of a heavy chain constant region containing an altered amino acid sequence provided by the present invention. More specifically, the present invention provides an antibody comprising heavy chains composed of constant and variable regions, wherein the amino acid sequence of the constant region is an amino acid sequence in which at least two of the following amino acids in the amino acid sequence of SEQ ID NO: 8 are altered to other amino acids.

Amino acid residues to be altered: Cys at position 102 (position 219 (EU numbering)) and Cys at position 103 (position 220 (EU numbering)).

In the present invention, the alteration of amino acid residues mentioned above may be substitution of Ser for Cys at position 102 and Cys at position 103. In addition to the above-mentioned alterations, the constant regions constituting the antibodies of the present invention can further include additional alterations. More specifically, the present invention relates to antibodies comprising constant regions in which, in addition to the above-mentioned alterations, a further additional alteration is made to at least one of the following amino acid residues.

Amino acids to be altered: His at position 147 (position 268 (EU numbering)), Arg at position 234 (position 355 (EU numbering)), and Gln at position 298 (position 419 (EU numbering)).

In the present invention, the following substitutions can be indicated as the alterations of the amino acid residues mentioned above.
His at position 147=>Gln
Arg at position 234=>Gln
Gln at position 298=>Glu Alternatively, constant regions constituting the antibodies of the present invention may include, in addition to the above-mentioned alterations, further additional alterations. More specifically, the present invention relates to antibodies comprising a constant region introduced with at least one of the above-mentioned alterations and further having additional deletions of the following amino acid residues.

Amino acid residues to be deleted: Gly at position 325 (position 446 (EU numbering)) and Lys at position 326 (position 447 (EU numbering)).

Antibodies of the present invention may include light chains in addition to the above-mentioned heavy chains. Preferred light chains in the present invention are light chains of IgG1 or IgG2. Similar to heavy chains, light chains can also include variable regions and constant regions. Amino acid alterations can be introduced into the variable regions or constant regions of the light chains as well. Alternatively, light chains without alterations or modifications of the amino acid sequence may also be combined.

The variable regions constituting the antibodies of the present invention may be variable regions that recognize any antigen. Preferred variable regions in the present invention include variable regions of antibodies having antigen-neutralizing actions. For example, a variable region of an antibody having the action of neutralizing the IL6 receptor can be used as a variable region constituting the antibodies of the present invention. Examples of such a variable region include the variable region of the heavy chain of an immunoglobulin indicated by the amino acid sequence of SEQ ID NO: 6. Amino acid sequences constituting the heavy chain variable regions are allowed to include alterations of one or more amino acid residues as long as their antigen binding activities are maintained.

Furthermore, examples include variable regions of antibodies in which a high biological activity can be obtained only in the IgG4 isotypes due to the effect of disulfide bond patterns near the hinge region. Using the antibody constant regions of the present invention, it is possible to decrease binding to Fcγ receptors while maintaining high biological activity and further improve the pharmacokinetics compared to the IgG1 isotype.

In the present invention, when altering the amino acid sequence of the variable region, its CDR sequences are preferably conserved. Therefore, the amino acid sequences of at least one, preferably two, or more preferably all three CDRs are desirably conserved. By conserving the CDR amino acid sequences, the antigen-binding properties of the variable regions can be maintained. The number of amino acid residues allowed to be altered in the variable region is usually one to ten, for example one to five, and preferably one or two amino acids. In the antibodies of the present invention, amino acid sequence alteration may be at least one of amino acid residue substitution, addition, deletion, or modification.

For example, modification of the N-terminal glutamine of the variable region to pyroglutamic acid by pyroglutamylation is a modification well-known to those skilled in the art. Therefore, when the heavy chain N terminus of the antibodies of the present invention is glutamine, the antibodies of the present invention include variable regions in which the glutamine is modified to pyroglutamic acid.

Unless significant changes are introduced to antigen-binding properties determined by the heavy chain variable regions, light chains constituting the antibodies of the present invention may include discretionary variable regions. This is because antigen-binding activities of antibodies are determined mainly by the variable regions of the heavy chains. Alternatively, it is acceptable to alter the variable portions of the light chains for the purpose of improving the antibody properties to more desirable conditions. Preferred light chain variable regions are light chain variable regions of antibodies from which the heavy chain variable regions are derived. Therefore, when using the variable region included in the amino acid sequence of SEQ ID NO: 6 for the heavy chain variable region, for example, a light chain consisting of the amino acid sequence of L0-k0 (SEQ ID NO: 2) may be combined. In the amino acid sequence of L0-k0 (SEQ ID NO: 2), the variable region is 1 to 107 and the constant region is 108 to 214 (SEQ ID NO: 14).

<Methods for Reducing the Heterogeneity Caused by the Hinge Region of IgG2 Constant Region>

The present invention also relates to methods for reducing antibody heterogeneity, which comprise the step of substituting other amino acids for Cys at position 102 (position 219 (EU numbering)) and Cys at position 103 (position 220 (EU numbering)) in the amino acid sequence of SEQ ID NO: 8 (IgG2). The type of amino acid after substitution is not particularly limited; however, substitutions of Ser for both Cys at position 102 and Cys at position 103 are preferred. The methods of the present invention for reducing antibody heterogeneity may comprise other steps of amino acid substitution, as long as they comprise the step of substituting other amino acids for Cys at position 102 (position 219 (EU numbering)) and Cys at position 103 (position 220 (EU numbering)) in the amino acid sequence of SEQ ID NO: 8 (IgG2). The method for amino acid substitution is not particularly limited. The substitutions can be achieved, for example, by site-directed mutagenesis described above or a method described in the Examples.

Alternatively, the present invention provides methods for producing antibodies with reduced heterogeneity derived from the hinge portion of the IgG2 constant region. The production methods of the present invention include the steps of expressing a DNA encoding an antibody H chain composed of (a) a constant region in which other amino acid(s) is/are substituted for both or either one of Cys at position 102 (position 219 (EU numbering)) and Cys at position 103 (position 220 (EU numbering)) in the amino acid sequence of SEQ ID NO: 8 (IgG2) and (b) a variable region, and a DNA encoding an antibody L chain; and collecting antibody molecules comprising the expressed antibody H chains and antibody L chains.

<Methods for Reducing the Heterogeneity Derived from Deletion of C-Terminal Amino Acids in an IgG2 Constant Region>

The present invention also relates to methods for reducing antibody heterogeneity, which comprise the step of deleting Gly at position 325 (position 446 (EU numbering)) and Lys at position 326 (position 447 (EU numbering)) in an IgG2 constant region comprising the amino acid sequence of SEQ ID NO: 8. The methods of the present invention for reducing antibody heterogeneity may comprise other steps of amino acid substitution, as long as they comprise the step of deleting Gly at position 325 (position 446 (EU numbering)) and Lys at position 326 (position 447 (EU numbering)) in an IgG2 constant region comprising the amino acid sequence of SEQ ID NO: 8. The method for amino acid substitution is not particularly limited. The substitution can be achieved, for example, by site-directed mutagenesis described above or a method described in the Examples.

Alternatively, the present invention provides methods for producing antibodies with heterogeneity derived from C-terminal amino acid deletion. The production methods of the present invention include the steps of expressing a DNA encoding an antibody H chain composed of (a) a constant region in which Gly at position 325 (position 446 (EU numbering)) and Lys at position 326 (position 447 (EU numbering)) in the IgG2 constant region comprising the amino acid sequence of SEQ ID NO: 8 are deleted and (b) a variable region, and a DNA encoding an antibody L chain; and collecting antibody molecules comprising the expressed antibody H chains and antibody L chains.

<Methods for Improving the Pharmacokinetics by Replacing Amino Acids of IgG2 Constant Region>

The present invention also relates to methods for improving the pharmacokinetics of an antibody, which comprise the step of substituting other amino acids for His at position 147 (position 268 (EU numbering)), Arg at position 234 (position 355 (EU numbering)), and/or Gln at position 298 (position 419 (EU numbering)) in an IgG2 constant region having the amino acid sequence of SEQ ID NO: 8. The methods of the present invention for improving the pharmacokinetics of an antibody may comprise other steps of amino acid substitution, as long as they comprise the above-described step. The type of amino acid after substitution is not particularly limited; however, substitutions of Gln for His at position 147 (position 268 (EU numbering)), Gln for Arg at position 234 (position 355 (EU numbering)), and Glu for Gln at position 298 (position 419 (EU numbering)) are preferred.

Alternatively, the present invention provides methods for producing antibodies with improved pharmacokinetics. The production methods of the present invention include the steps of expressing a DNA encoding an antibody H chain composed of (a) a constant region in which other amino acid(s) is/are substituted for at least one amino acid residue selected from the group consisting of His at position 147 (position 268 (EU numbering)), Arg at position 234 (position 355 (EU numbering)), and Gln at position 298 (position 419 (EU numbering)) in the IgG2 constant region having the amino acid sequence of SEQ ID NO: 8 and (b) a variable region, and a DNA encoding an antibody L chain; and collecting antibody molecules comprising the expressed antibody H chains and antibody L chains.

Furthermore, the present invention relates to methods for reducing heterogeneity caused by the IgG2 hinge portion, methods for improving pharmacokinetics, and/or methods for reducing heterogeneity caused by the C terminus in the IgG2 constant region having the amino acid sequence of SEQ ID NO: 8, comprising the steps of:

(a) substituting another amino acid for Cys at position 102 (position 219 (EU numbering)) of SEQ ID NO: 8;
(b) substituting another amino acid for Cys at position 103 (position 220 (EU numbering)) of SEQ ID NO: 8;
(c) substituting another amino acid for His at position 147 (position 268 (EU numbering)) of SEQ ID NO: 8;
(d) substituting another amino acid for Arg at position 234 (position 355 (EU numbering)) of SEQ ID NO: 8;
(e) substituting another amino acid for Gln at position 298 (position 419 (EU numbering)) of SEQ ID NO: 8; and
(f) deleting Gly at position 325 and Lys at position 326 (positions 446 and 447 (EU numbering)) of SEQ ID NO: 8.

The amino acids after substitution are not particularly limited, but preferably Ser is substituted for Cys at position 102 (position 219 (EU numbering)), Ser is substituted for Cys at position 103 (position 220 (EU numbering)), Gln is substituted for His at position 147 (position 268 (EU numbering)), Gln is substituted for Arg at position 234 (position 355 (EU numbering)), and Glu is substituted for Gln at position 298 (position 419 (EU numbering)).

Alternatively, the present invention relates to methods for producing antibodies with an improvement in either or both of heterogeneity and pharmacokinetics; wherein the methods comprise the steps of expressing a DNA encoding an antibody H chain with at least one amino acid residue alteration selected from the group consisting of (a) to (f) mentioned above and a DNA encoding an antibody L chain, and collecting antibody molecules comprising the expressed antibody H chains and antibody L chains.

The methods of the present invention may comprise other steps such as amino acid substitution and deletion, as long as they comprise the steps described above. The methods for amino acid substitution and deletion are not particularly limited. The substitution and deletion can be achieved, for example, by site-directed mutagenesis described above or a method described in the Examples.

<Pharmaceutical Compositions Comprising Antibodies>

The present invention provides pharmaceutical compositions comprising an antibody of the present invention.

The pharmaceutical compositions of the present invention can be formulated, in addition to the antibodies, with pharmaceutically acceptable carriers by known methods. For example, the compositions can be used parenterally, when the antibodies are formulated in a sterile solution or suspension for injection using water or any other pharmaceutically acceptable liquid. For example, the compositions can be formulated by appropriately combining the antibodies with pharmaceutically acceptable carriers or media, specifically, sterile water or physiological saline, vegetable oils, emulsifiers, suspending agents, surfactants, stabilizers, flavoring agents, excipients, vehicles, preservatives, binding agents, and such, by mixing them at a unit dose and form required by generally accepted pharmaceutical implementations. The content of the active ingredient in such a formulation is adjusted so that an appropriate dose within the required range can be obtained.

Sterile compositions for injection can be formulated using vehicles such as distilled water for injection, according to standard protocols.

Aqueous solutions used for injection include, for example, physiological saline and isotonic solutions containing glucose or other adjuvants such as D-sorbitol, D-mannose, D-mannitol, and sodium chloride. These can be used in conjunction with suitable solubilizers such as alcohol, specifically ethanol, polyalcohols such as propylene glycol and polyethylene glycol, and non-ionic surfactants such as Polysorbate 80' and HCO-50.

Oils include sesame oils and soybean oils, and can be combined with solubilizers such as benzyl benzoate or benzyl alcohol. These may also be formulated with buffers, for example, phosphate buffers or sodium acetate buffers; analgesics, for example, procaine hydrochloride; stabilizers, for example, benzyl alcohol or phenol; or antioxidants. The prepared injections are typically aliquoted into appropriate ampules.

The administration is preferably carried out parenterally, and specifically includes injection, intranasal administration, intrapulmonary administration, and percutaneous administration. For example, injections can be administered systemically or locally by intravenous injection, intramuscular injection, intraperitoneal injection, or subcutaneous injection.

Furthermore, the method of administration can be appropriately selected according to the age and symptoms of the patient. A single dose of the pharmaceutical composition containing an antibody or a polynucleotide encoding an antibody can be selected, for example, from the range of 0.0001 to 1,000 mg per kg of body weight. Alternatively, the dose may be, for example, in the range of 0.001 to 100,000 mg/patient. However, the dose is not limited to these values. The dose and method of administration vary depending on the patient's body weight, age, and symptoms, and can be appropriately selected by those skilled in the art.

As used herein, the three-letter and single-letter codes for respective amino acids are as follows:
Alanine: Ala (A)
Arginine: Arg (R)
Asparagine: Asn (N)
Aspartic acid: Asp (D)
Cysteine: Cys (C)
Glutamine: Gln (Q)
Glutamic acid: Glu (E)
Glycine: Gly (G)
Histidine: His (H)
Isoleucine: Ile (I)
Leucine: Leu (L)
Lysine: Lys (K)
Methionine: Met (M)
Phenylalanine: Phe (F)
Proline: Pro (P)
Serine: Ser (S)
Threonine: Thr (T)
Tryptophan: Trp (W)
Tyrosine: Tyr (Y)
Valine: Val (V)

All prior art documents cited herein are incorporated by reference in their entirety.

EXAMPLES

[Example 1] Improvement of C-Terminal Heterogeneities of IgG Molecules

Construction of an Expression Vector for H-Chain C-Terminal ΔGK Antibody

Heterogeneities of the C-terminal sequence of the IgG antibody H chain that have been reported are deletion of the C-terminal amino acid lysine residue, and amidation of the C-terminal carboxyl group due to deletion of both of the two C-terminal amino acids, glycine and lysine residues (Anal Biochem. 2007 Jan. 1; 360(1):75-83). In TOCILIZUMAB which is an anti-IL-6 receptor antibody, the main component is a sequence in which the C-terminal amino acid lysine present on the nucleotide sequence is deleted by posttranslational modification, but an accessory component with remnant lysine and an accessory component with an amidated C-terminal carboxyl group produced by deletion of both glycine and lysine are also present as heterogeneities. It is not easy to manufacture such an antibody as a pharmaceutical in a large scale, while maintaining differences of desired product/related substance-related heterogeneity between productions, which will lead to increased cost. Thus, single substances are desirable as much as possible, and in developing antibodies as pharmaceuticals, such heterogeneities are desirably reduced. Therefore, in terms of development as pharmaceuticals, absence of heterogeneities of the H-chain C terminal is desirable.

Thus, C-terminal amino acids were altered to reduce C-terminal heterogeneity. Specifically, the present inventors altered the nucleotide sequence of wild type IgG1 to delete the C-terminal lysine and glycine from the H-chain constant region of the IgG1, and assessed whether the amidation of the C-terminal amino group due to deletion of the two C-terminal amino acids glycine and lysine could be suppressed.

According to the method of Reference Example 1, TOCILIZUMAB (hereinafter abbreviated as IL6R H0/L0-IgG1) consisting of H0-IgG1 (amino acid SEQ ID NO: 1) as an H chain and L0-k0 (amino acid SEQ ID NO: 2) as an L chain was prepared. Furthermore, the nucleotide sequence of the H chain encoding Lys at position 447 and/or Gly at position 446 in the EU numbering was converted into a stop codon. Thus, expression vectors for antibody H chain H0-IgG1ΔK (amino acid SEQ ID NO: 3) engineered to lack the C-terminal amino acid lysine (position 447 (EU numbering)) and antibody H chain H0-IgG1ΔGK (amino acid SEQ ID NO: 4) engineered to lack the two C-terminal amino acids glycine and lysine (positions 446 and 447 (EU numbering), respectively) were constructed.

IL6R H0-IgG1/L0-k0 consisting of H0-IgG1 (amino acid SEQ ID NO: 1) as the H chain and L0-k0 (amino acid SEQ ID NO: 2) as the L chain, IL6R H0-IgG1ΔK/L0-k0 consisting of H0-IgG1ΔK (amino acid SEQ ID NO: 3) as the H chain and L0-k0 (amino acid SEQ ID NO: 2) as the L chain, and IL6R H0-IgG1ΔGK/L0-k0 consisting of H0-IgG1ΔGK-k0 (amino acid SEQ ID NO: 4) as the H chain and L0-k0 (amino acid SEQ ID NO: 2) as the L chain were expressed and purified by the method described in Reference Example 1. The heavy-chain and light-chain combinations of the above-mentioned antibodies are summarized below.

| Antibody | Heavy chain | Light chain |
|---|---|---|
| IL6R H0-IgG1/L0-k0 | SEQ ID NO: 1 | SEQ ID NO: 2 |
| IL6R H0-IgG1ΔK/L0-k0 | SEQ ID NO: 3 | SEQ ID NO: 2 |
| IL6R H0-IgG1ΔGK/L0-k0 | SEQ ID NO: 4 | SEQ ID NO: 2 |

Cation Exchange Chromatographic Analysis of the H-Chain C-Terminal ΔGK Antibody

Heterogeneity of the purified antibodies was evaluated by performing cation exchange chromatography. ProPac WCX-10, 4×250 mm (Dionex) was used for the column, 25 mmol/L MES/NaOH, pH 6.1 was used as mobile phase A, 25 mmol/L MES/NaOH, 250 mmol/L NaCl, pH 6.1 was used as mobile phase B, and the chromatography was performed using appropriate flow and gradient. The results of performing cation exchange chromatographic evaluations on the purified IL6R H0-IgG1/L0-k0, IL6R H0-IgG1ΔK/L0-k0, and IL6R H0-IgG1ΔGK/L0-k0 are shown in FIG. 1.

From the results, it was discovered that heterogeneity of the C-terminal amino acid can be decreased for the first time by deleting in advance both the C-terminal lysine and glycine of the H-chain constant region, not only the C-terminal lysine of the H-chain constant region, from the nucleotide sequence. In the human antibody constant regions of IgG1, IgG2, and IgG4, the C-terminal sequence is lysine at position 447 and glycine at position 446 in the EU numbering (see Sequences of proteins of immunological interest, NIH Publication No. 91-3242) in all cases; therefore, the method of reducing C-terminal amino acid heterogeneity discovered in the present examination was considered to be applicable to the IgG2 constant region and IgG4 constant region, or their modified forms.

[Example 2] Production of a Novel Constant Region Showing Better Pharmacokinetics than Natural IgG1 with Reduced Heterogeneity Caused by Disulfide Bonds in Natural IgG2

Heterogeneity of Natural IgG1 and Natural IgG2

For antibody pharmaceuticals against cancer such as those that kill target cells with effector functions and such, IgG1 constant region (isotype) having effector function is preferred. However, for antibody pharmaceuticals that neutralize the functions of a target antigen or antibody pharmaceuticals that bind to target cells but do not kill them, binding to Fcγ receptors is not preferred.

As methods for decreasing the binding to Fcγ receptors, the method of changing the IgG antibody isotype from IgG1 to IgG2 or IgG4 has been considered (Ann Hematol. 1998 June; 76(6):231-48), and from the viewpoint of binding to Fcγ receptor I and pharmacokinetics of each isotype, IgG2 was considered to be more desirable than IgG4 (Nat Biotechnol. 2007 Dec.; 25(12):1369-72). On the other hand, when developing antibodies into pharmaceuticals, physicochemical properties of the proteins, particularly homogeneity and stability are extremely important. The IgG2 isotype has been reported to have a very high degree of heterogeneity caused by disulfide bond linkage differences in the hinge region (J Biol Chem. 2008 Jun. 6; 283(23):16194-205; J Biol Chem. 2008 Jun. 6; 283(23):16206-15; Biochemistry 2008 Jul. 15; 47(28):7496-508).

Accordingly, IL6R H0-IgG1/L0-k0 having the constant regions of natural IgG1 and IL6R H0-IgG2/L0-k0 having the constant regions of natural IgG2 were actually produced and heterogeneity evaluations were carried out for both of them. IL6R H0-IgG1/L0-k0 which was produced in Example 1 consisting of IL6R H0-IgG1 (amino acid SEQ ID NO: 1) as the H chain and IL6R L0-k0 (amino acid SEQ ID NO: 2) as the L chain and IL6R H0-IgG2/L0-k0 consisting of IL6R H0-IgG2 (amino acid SEQ ID NO: 5) as the H chain in which the H-chain constant region was converted to IgG2 and IL6R L0-k0 (amino acid SEQ ID NO: 2) as the L chain were expressed and purified by the method described in Reference Example 1. The heavy-chain and light-chain combinations in the above-mentioned antibodies are summarized below.

| Antibody | Heavy chain | Light chain |
|---|---|---|
| IL6R H0-IgG1/L0-k0 | SEQ ID NO: 1 | SEQ ID NO: 2 |
| IL6R H0-IgG2/L0-k0 | SEQ ID NO: 5 | SEQ ID NO: 2 |

Figure 2:
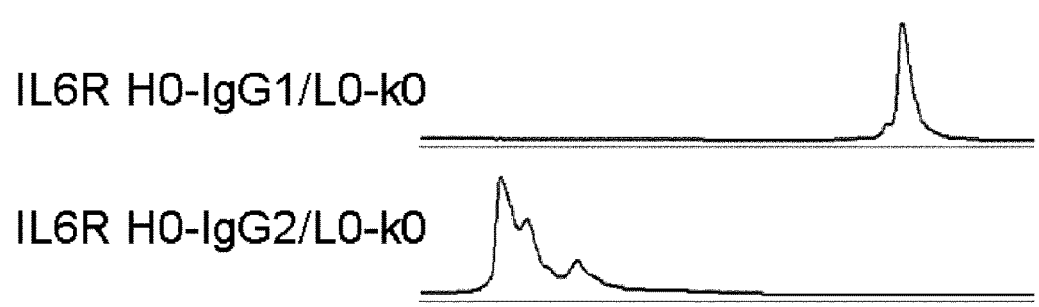
FIG. 2 depicts the results of performing cation exchange chromatography on IL6R H0-IgG1/L0-k0 and IL6R H0-IgG2/L0-k0 to evaluate the heterogeneity derived from disulfide bonds. In the figure, the vertical axis shows absorbance at 280 nm and the horizontal axis shows elution time (minutes).

Evaluation by cation exchange chromatography was carried out as the method for evaluating the heterogeneity caused by disulfide bonds in IL6R H0-IgG1/L0-k0 having the constant regions of natural IgG1 and IL6R H0-IgG2/L0-k0 having the constant regions of natural IgG2. ProPac WCX-10 (Dionex) was used for the column, 20 mM sodium acetate, pH 5.0 was used as mobile phase A, 20 mM sodium acetate, 1 M NaCl, pH 5.0 was used as mobile phase B, and the chromatography was performed using appropriate flow and gradient. As a result, as shown in FIG. 2, IL6R H0-IgG2/L0-k0 having the constant regions of natural IgG2 showed multiple peaks and it was found to have markedly high heterogeneity compared to IL6R H0-IgG1/L0-k0 having the constant regions of natural IgG1 showing only almost single main peak.

Figure 3:
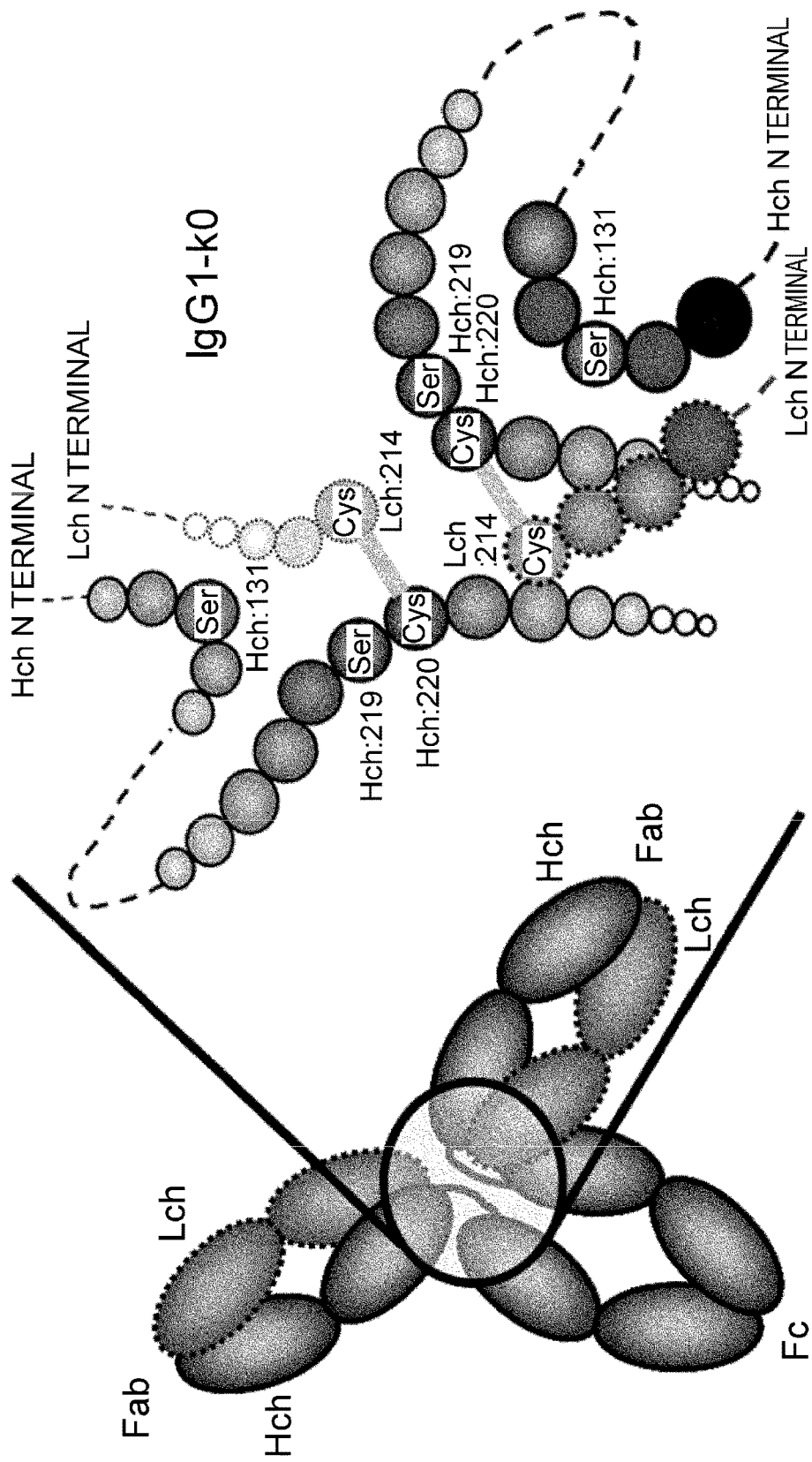
FIG. 3 depicts the IgG-type antibody and details of the structure around its hinge region (positioning of the H chain and L chain and disulfide bonds between them; detailed drawing represents IgG1-k0).
Figure 4:
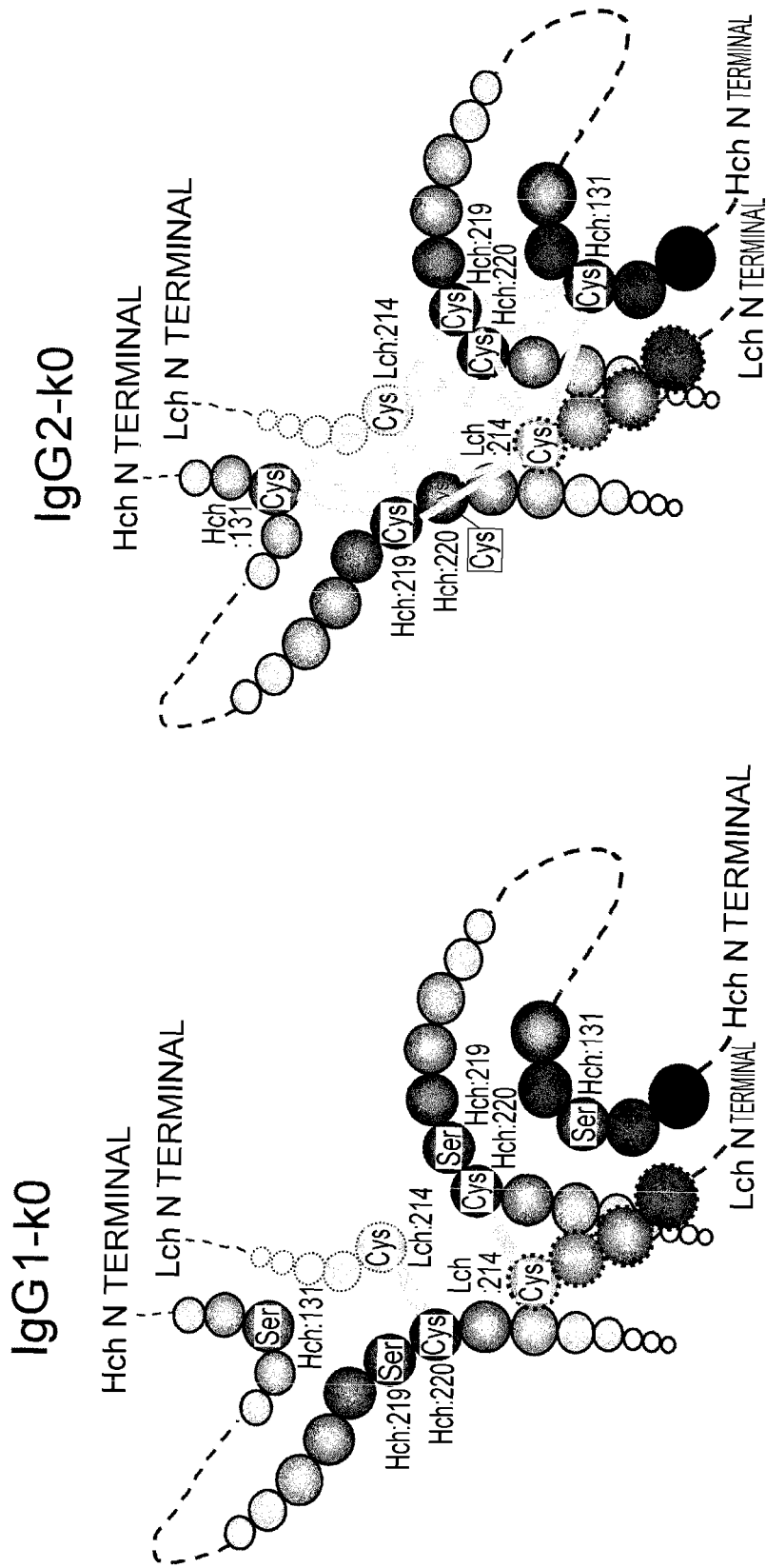
FIG. 4 depicts the predicted disulfide bond patterns around the hinge region of the constant regions IgG1-k0 and IgG2-k0. Various conceivable disulfide bond patterns in IgG2-k0 are indicated by bold lines.

The details of the structure around the hinge region of an IgG-type antibody are shown in FIG. 3. In IgG antibodies, H and L chains (or two H chains) form disulfide bonds near the hinge region. This pattern of disulfide bonds differ depending on the isotypes of the IgG-type antibodies as indicated below. It is considered that since disulfide bonds in the hinge region of natural IgG1 have a single pattern such as that shown in FIG. 4, heterogeneity caused by disulfide bonds does not exist and it was eluted as a nearly single main peak in cation exchange chromatography.

In contrast, as shown in FIG. 3, regarding the disulfide bonds in the hinge region of natural IgG2, natural IgG2 has two cysteines in the hinge region (positions 219 and 220 (EU numbering)), and cysteines exist adjacent to these two cysteines of the hinge region, which are cysteine at position 131 in the EU numbering, present in the H-chain CH1 domain, cysteine at the L-chain C terminus, and two cysteines of the same hinge region of the H chain of the dimerization partner. Therefore, around the hinge region of IgG2, there are a total of eight neighboring cysteines when an H2L2 assembly is formed. This leads to the presence of a variety of heterogeneity due to disulfide bond linkage differences in natural IgG2, and the heterogeneity is considered to be remarkably high.

It is not easy to manufacture as a pharmaceutical in a large scale while maintaining the differences of desired product/related substance-related heterogeneity between productions (the differences caused by these disulfide bond linkage differences), and this leads to increased cost. Thus, single substances are desirable as much as possible. Therefore, in developing antibodies of the IgG2 isotype into pharmaceuticals, it is desirable to reduce heterogeneity derived from disulfide bonds without decreasing stability. In fact, it is reported in US 20060194280 (A1) that a variety of heterogeneous peaks derived from disulfide bonds were observed for natural IgG2 in ion exchange chromatographic analysis, and biological activities were also reported to be different among these peaks.

As a method for unifying these heterogeneous peaks, US 20060194280 (A1) reports refolding in the purification steps, but since using these steps in the production will be costly and complicated, preferably, unifying the heterogeneous peaks by producing an IgG2 variant in which disulfide bonds will be formed in a single pattern by means of amino acid substitutions was considered desirable. However, to date, there had been no reports on IgG2 variants that will form disulfide bonds in a single pattern.

Production of Various Types of Natural IgG2 Variants

As methods for reducing heterogeneity due to disulfide bond linkage differences in natural IgG2, one can consider the method of altering only cysteine at position 219 in the EU numbering, which is present in the hinge region of the H chain, to serine, and the method of altering only cysteine at position 220 to serine (Biochemistry 2008 Jul. 15; 47(28): 7496-508). When such strategies are applied to the amino acid sequence (amino acid SEQ ID NO: 8) of the H-chain constant region of natural IgG2, variants such as the following are conceivable:
SC: H-chain constant region in which cysteine at position 219 in the EU numbering is altered to serine (SEQ ID NO: 10); and
CS: H-chain constant region in which cysteine at position 220 is altered to serine (SEQ ID NO: 11).

Figure 5:
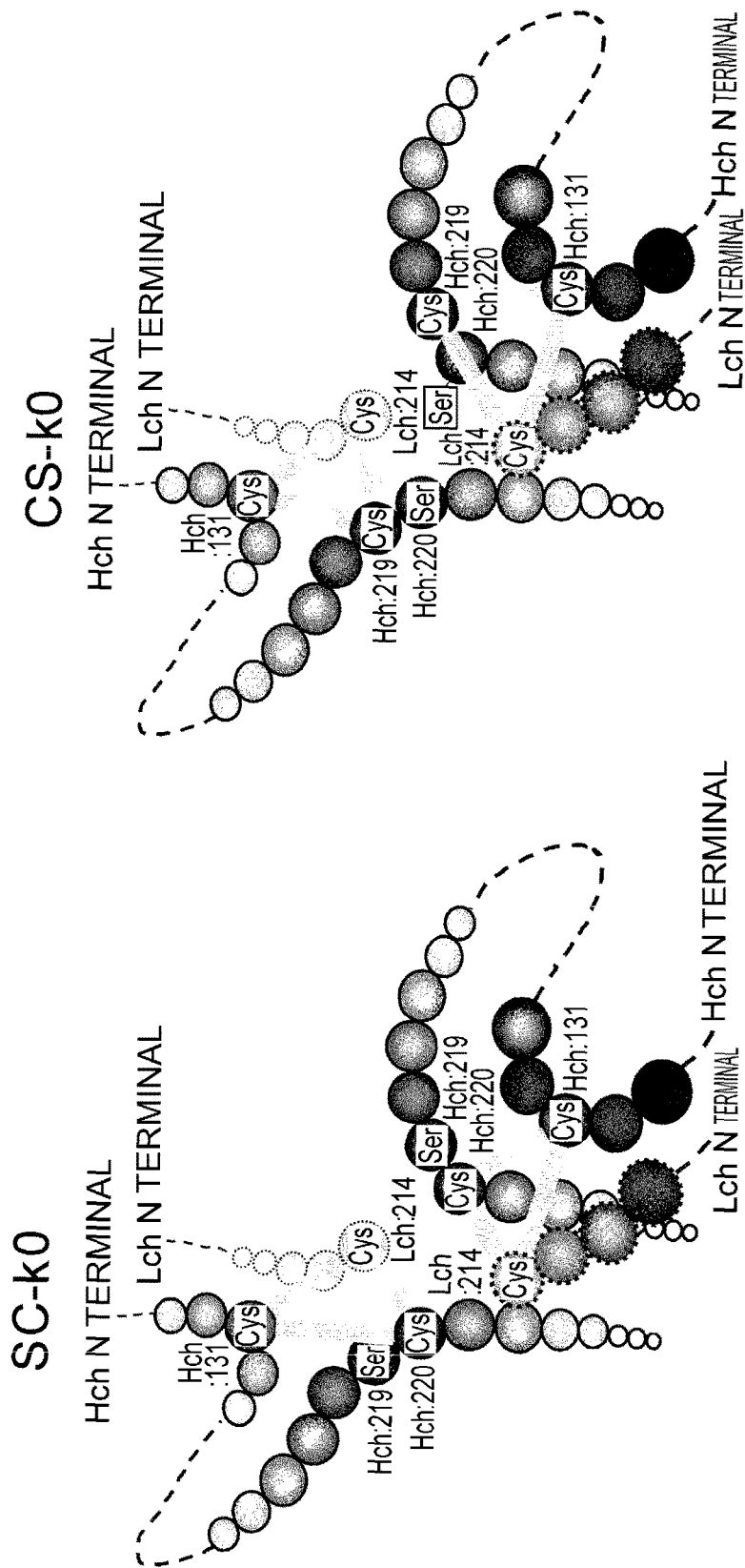
FIG. 5 depicts the predicted disulfide bond patterns around the hinge region of the constant regions SC-k0 and CS-k0. Various conceivable disulfide bond patterns in SC-k0 and CS-k0 are indicated by bold lines.

However, similarly to the natural IgG2, these H-chain constant regions SC and CS do not have a single disulfide bond pattern, as shown in FIG. 5 and multiple patterns are possible. Thus, a lot of heterogeneity may still exist.

Figure 6:
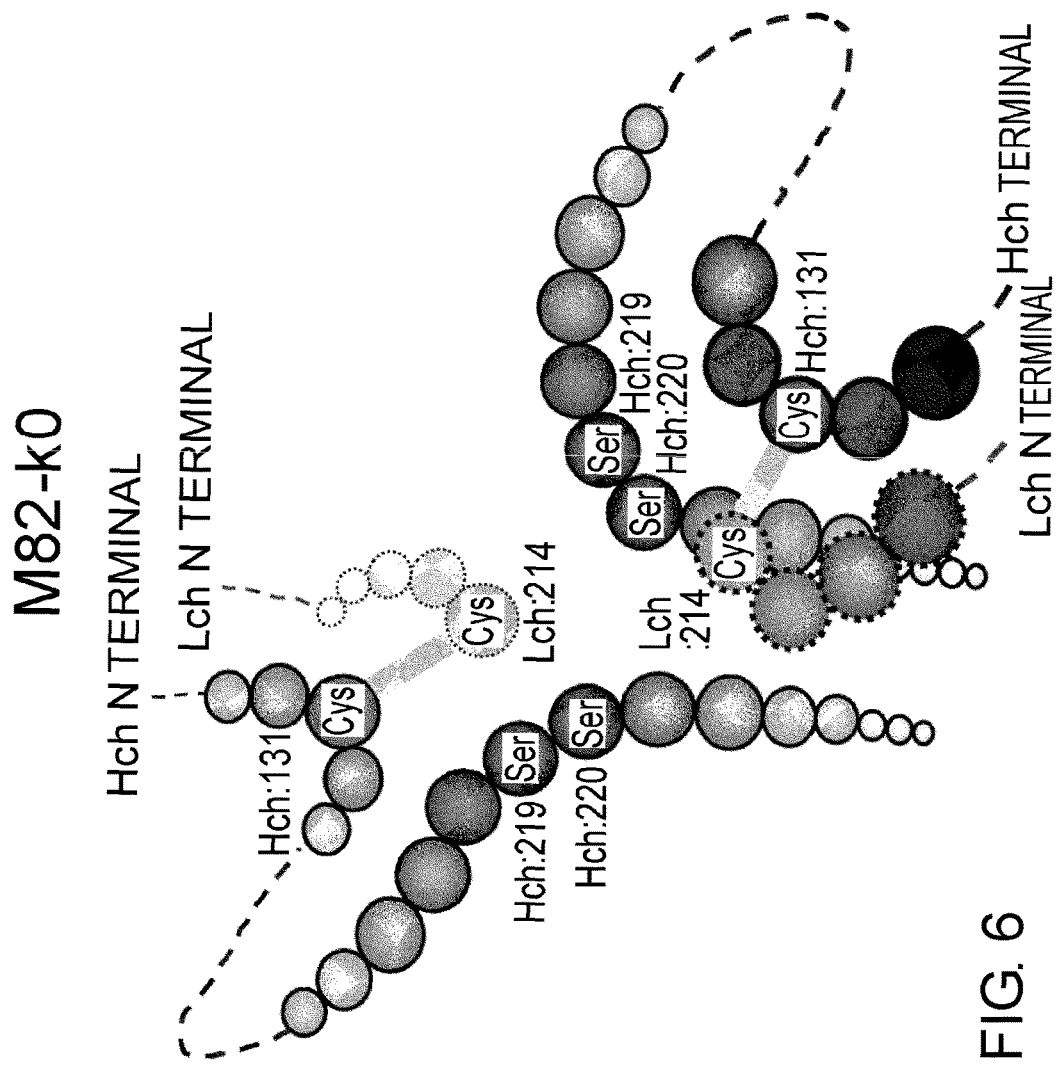
FIG. 6 depicts the predicted disulfide bond patterns around the hinge region of the constant region M82-k0.

Accordingly, as an H-chain constant region that will form a single disulfide bond pattern, cysteine at position 219 in EU numbering of the H chain was further altered to serine in SC (SEQ ID NO: 10). Furthermore, M82 (SEQ ID NO: 13), which is an H-chain constant region in which histidine at position 268 is altered to glutamine, arginine at position 355 is altered to glutamine, and glutamine at position 419 is altered to glutamic acid for improvement of pharmacokinetics, and the C-terminal lysine and glycine of the H-chain constant region are deleted in advance from the nucleotide sequence to further avoid heterogeneity of the H-chain C terminus, was developed. As indicated in FIG. 6, M82 is thought to form a single disulfide bond pattern.

Subsequently, construction of an expression vector for IL6R H0-M82 (amino acid SEQ ID NO: 6) was carried out by the method described in Reference Example 1. IL6R H0-M82 (amino acid SEQ ID NO: 6) was used as the H chain, IL6R L0-k0 (amino acid SEQ ID NO: 2) was used as the L chain, and IL6R H0-M82/L0-k0 was expressed and purified by the method of Reference Example 1.

Analysis of Heterogeneity by Cation Exchange Chromatographic Analysis

As a method for evaluating the heterogeneity of H0-M82/L0-k0, the above-described method using cation exchange chromatography was used to perform the analysis. The results of performing evaluations of IL6R H0-IgG1/L0-k0, IL6R H0-IgG2/L0-k0, and IL6R H0-M82/L0-k0 by cation exchange chromatography are shown in FIG. 7.

Figure 7:
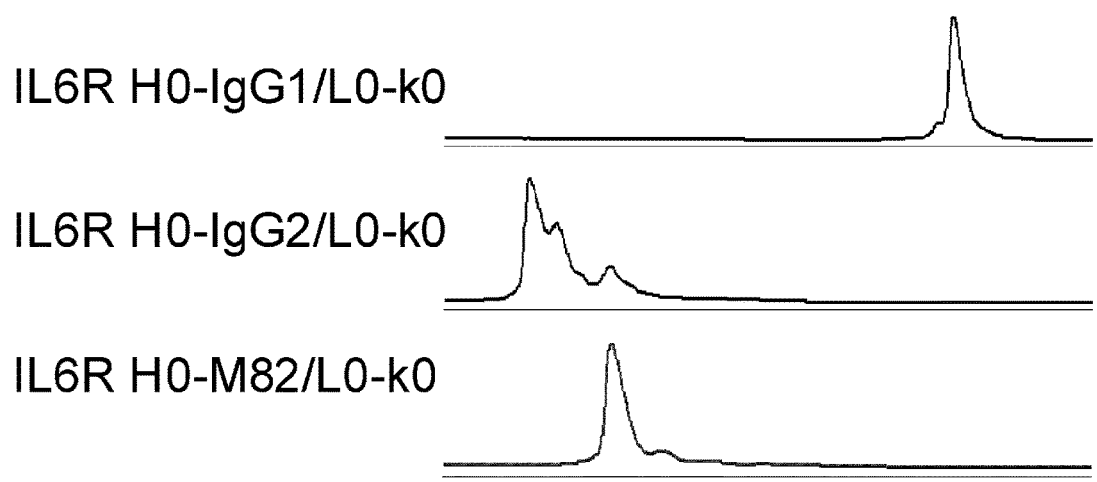
FIG. 7 depicts the results of performing cation exchange chromatography on antibodies IL6R H0-IgG1/L0-k0, IL6R H0-IgG2/L0-k0, and IL6R H0-M82/L0-k0 to evaluate the heterogeneity derived from disulfide bond linkage differences. In the figure, the vertical axis shows absorbance at 280 nm and the horizontal axis shows elution time (minutes).

As a result, as shown in FIG. 7, heterogeneity increased by changing the H-chain constant region from IgG1 to IgG2, but heterogeneity drastically decreased by changing the H-chain constant region to M82.

Pharmacokinetics of IgG-Type Antibodies

The prolonged retention (slow elimination) of IgG molecule in plasma is known to be due to the function of FcRn which is known as a salvage receptor of IgG molecule (Nat. Rev. Immunol. 2007 Sep.; 7(9):715-25). When taken up into endosomes via pinocytosis, IgG molecules bind to FcRn expressed in endosomes under the acidic conditions within the endosomes (approx. pH 6.0). While IgG molecules that do not bind to FcRn are transferred and degraded in lysosomes, those bound to FcRn are translocated to the cell surface and then released from FcRn back into plasma again under the neutral conditions in the plasma (approx. pH 7.4).

Known IgG-type antibodies include the IgG1, IgG2, IgG3, and IgG4 isotypes. The plasma half-lives of these isotypes in human are reported to be about 36 days for IgG1 and IgG2; about 29 days for IgG3; and 16 days for IgG4 (Nat. Biotechnol. 2007 Dec.; 25(12):1369-72). Thus, the retention of IgG1 and IgG2 in plasma is believed to be the longest. In general, the isotypes of antibodies used as pharmaceutical agents are IgG1, IgG2, and IgG4. Methods reported for further improving the pharmacokinetics of these IgG antibodies include methods for improving the above-described binding to human FcRn, and this is achieved by altering the sequence of IgG constant region (J. Biol. Chem. 2007 Jan. 19; 282(3):1709-17; J. Immunol. 2006 Jan. 1; 176(1):346-56).

There are species-specific differences between mouse FcRn and human FcRn (Proc. Natl. Acad. Sci. USA. 2006 Dec. 5; 103(49):18709-14). Therefore, to predict the plasma retention of IgG antibodies that have an altered constant region sequence in human, it is desirable to assess the binding to human FcRn and retention in plasma in human FcRn transgenic mice (Int. Immunol. 2006 Dec.; 18(12): 1759-69).

Comparison of IgG1-k0 and M82-k0 for the Binding to Human FcRn

Human FcRn was prepared according to the method described in Reference Example 2. The binding to human FcRn was assessed using Biacore 3000. An antibody was bound to Protein L or rabbit anti-human IgG Kappa chain antibody immobilized onto a sensor chip, human FcRn was added as an analyte for interaction with the antibody, and the affinity (KD) was calculated from the amount of bound human FcRn. Specifically, Protein L or rabbit anti-human IgG Kappa chain antibody was immobilized onto sensor chip CM5 (BIACORE) by the amine coupling method using 50 mM Sodium-phosphate buffer (pH 6.0) containing 150 mM NaCl as the running buffer. Then, IL6R H0-IgG1/L0-k0 and IL6R H0-M82/L0-k0 was each diluted with a running buffer containing 0.02% Tween20, and injected to be bound to the chip. Human FcRn was then injected and the binding of the human FcRn to antibody was assessed.

The affinity was computed using BIAevaluation Software. The obtained sensorgram was used to calculate the amount of hFcRn bound to the antibody immediately before the end of human FcRn injection. The affinity of the antibody for human FcRn was calculated by fitting with the steady state affinity method.

As a result of evaluating the binding of IL6R H0-IgG1/L0-k0 and IL6R H0-M82/L0-k0 towards human FcRn by BIAcore, as shown in Table 1, the binding of IL6R H0-M82/L0-k0 was found to be increased approximately 1.34 times compared to that of IL6R H0-IgG1/L0-k0.

TABLE 1

|  | KD/μM |
| --- | --- |
| IL6R H0-IgG1/L0-k0 | 1.62 |
| IL6R H0-M82/L0-k0 | 1.21 |

Comparison of IgG1-k0 and M82-k0 for Pharmacokinetics in Human FcRn Transgenic Mice The pharmacokinetics in human FcRn transgenic mice (B6.mFcRn−/−.hFcRn Tg line 276 +/+ mice; Jackson Laboratories) was assessed by the following procedure. IL6R H0-IgG1/L0-k0 and IL6R H0-M82/L0-k0 was each intravenously administered once at a dose of 1 mg/kg to mice, and blood was collected at appropriate time points. The collected blood was immediately centrifuged at 15,000 rpm and 4° C. for 15 minutes to obtain blood plasma. The separated plasma was stored in a freezer at −20° C. or below until use. The plasma concentration was determined by ELISA (see Reference Example 3).

Figure 8:
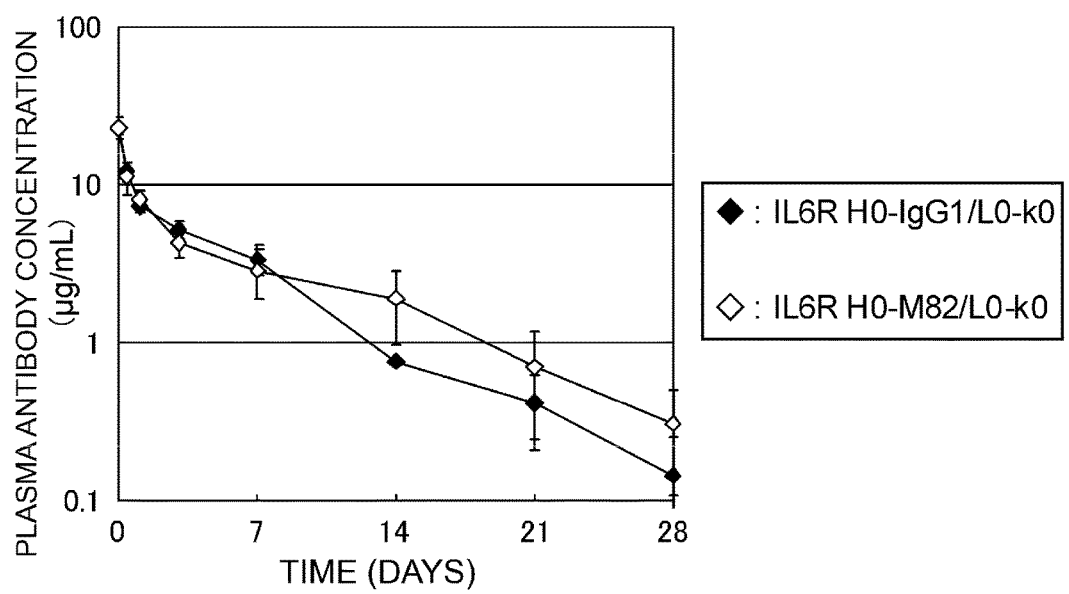
FIG. 8 depicts the shift in plasma antibody concentration when the antibodies were administered at 1 mg/kg to human FcRn transgenic mice. In the figure, the vertical axis shows plasma antibody concentration (μg/mL) and the horizontal axis shows period of time (days) passed after administration. The administered antibodies were IL6R H0-IgG1/L0-k0 (filled diamond: antibody with unaltered constant regions) and IL6R H0-M82/L0-k0 (open diamond: antibody with altered constant regions).

As a result of evaluating the plasma retention of IL6R H0-IgG1/L0-k0 and IL6R H0-M82/L0-k0 in human FcRn transgenic mice, as shown in FIG. 8, pharmacokinetics of IL6R H0-M82/L0-k0 was confirmed to be improved compared to IL6R H0-IgG1/L0-k0. As indicated above, this was considered to be due to improvement in the binding of IL6R H0-M82/L0-k0 to human FcRn compared to IL6R H0-IgG1/L0-k0.

IL6R H0-M82/L0-k0 not only avoids heterogeneity derived from disulfide bonds of natural IgG2, but also shows improvement of pharmacokinetics compared to natural IgG1 by means of substituting serine for cysteine at positions 219 and 220, EU numbering, in the H chain, and moreover, heterogeneity derived from the H-chain C terminus is also avoided by ΔGK modification of the H-chain C terminus indicated in Example 1. Thus, M82 (SEQ ID NO: 13)/k0 (SEQ ID NO: 14) was considered to be very useful as H-chain/L-chain constant regions of antibodies.

Generally, IgG antibodies are known to differ not only in their effector functions such as ADCC activity, but also differ greatly in terms of their antigen-binding ability and biological activity derived from binding to antigens depending on the isotype (IgG1, IgG2, IgG3, IgG4, or their modified forms) (Immunology 1996, 88, 169-173; Mol Immunol. 1994 Jun.; 31(8):577-84; Infection and Immunity, March 2007, 1424-1435; Nat Biotechnol. 2007 Dec.; 25(12):1369-72; Nat Biotechnol. 2008 Feb.; 26(2):209-11). One of the reasons for this may be that flexibility of the IgG hinge portion is different depending on the isotype (J Immunol. 1997 Oct. 1; 159(7):3372-82; Mol Immunol. 1994 Oct.; 31(15):1201-10). Factors affecting the flexibility of the hinge portion may be the disulfide bond patterns near the hinge region.

For example, in the case of antibodies for which a high biological activity is obtained only in the IgG4 isotype (WO 2005/035756), to obtain a high biological activity similar to that of IgG4, the same disulfide bond pattern near the hinge region as in the IgG4 isotype may be necessary. As described above, from the viewpoint of binding to Fcγ receptor I and pharmacokinetics of each isotype, IgG2 may be more desirable than IgG4 (Nat Biotechnol. 2007 Dec.; 25(12):1369-72), but the disulfide bond patterns near the hinge region are different between IgG2 and IgG4. Therefore, it is very likely that high biological activity similar to that of the IgG4 isotype may not be obtainable with the IgG2 isotype.

Figure 9:
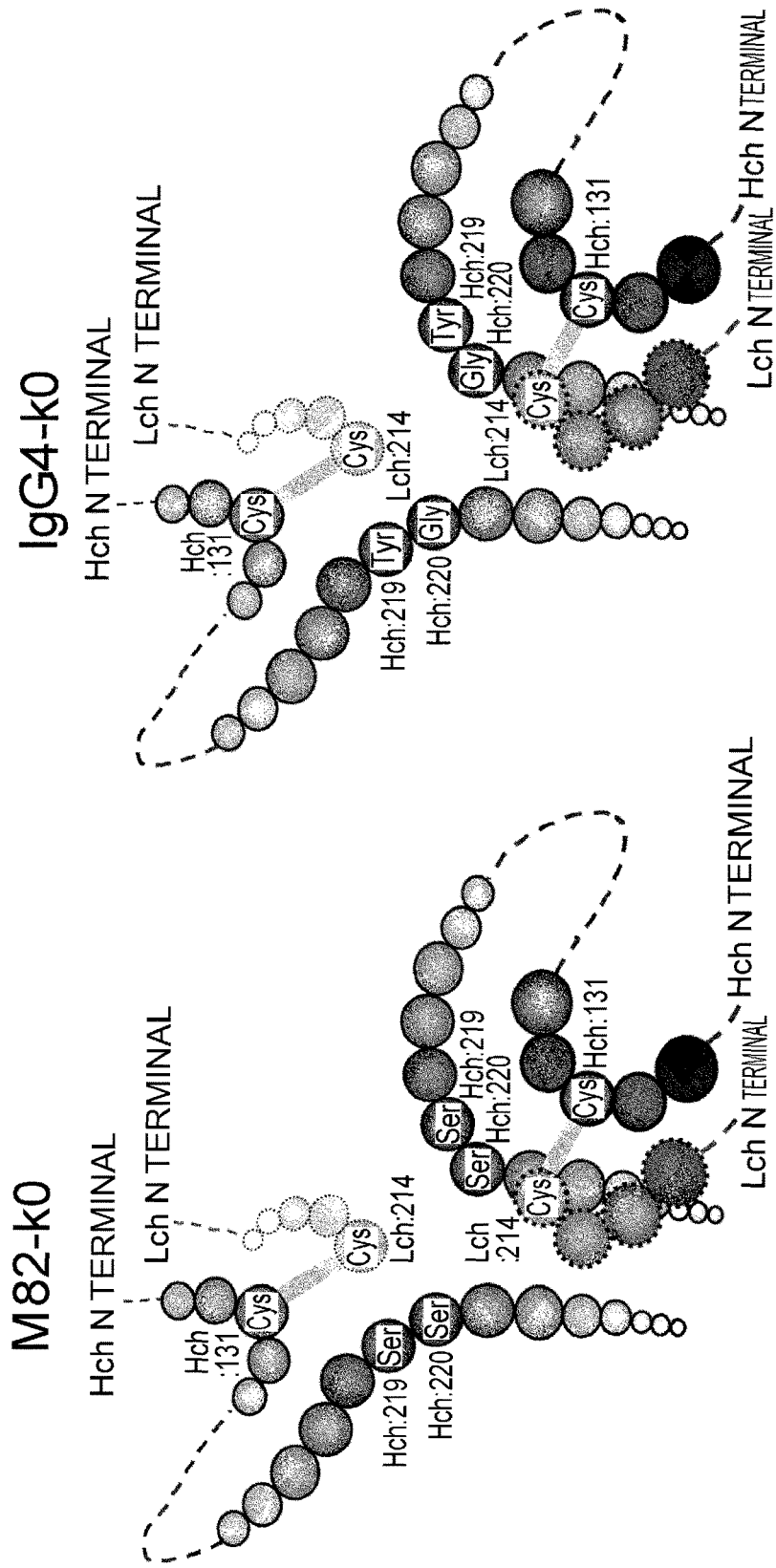
FIG. 9 depicts the predicted disulfide bond patterns around the hinge region of constant regions M82-k0 and IgG4-k0.

As indicated in FIG. 9, since the disulfide bond pattern near the hinge region of the novel constant region M82 discovered in the present examination is the same as that of IgG4, it may have flexibility of the hinge portion similar to that of the IgG4 isotype. Therefore, the novel constant region M82 was considered to be very useful since it may be possible to maintain the high biological activity of the IgG4 isotype, decrease the binding to Fcγ receptors, and improve the pharmacokinetics compared to that of IgG1 in antibodies that yield high biological activity only in the IgG4 isotype.

[Reference Example 1] Production of Antibody Expression Vectors and Expression and Purification of Antibodies Genes encoding the nucleotide sequences of the H chain and L chain of the antibody of interest were amplified using PCR and such by methods known to those skilled in the art. Introduction of amino acid substitutions were carried out by methods known to those skilled in the art using QuikChange Site-Directed Mutagenesis Kit (Stratagene), PCR, or such. The obtained plasmid fragment was inserted into an animal cell expression vector, and the H-chain expression vector and L-chain expression vector of interest were produced. The nucleotide sequence of the obtained expression vector was determined by a method known to those skilled in the art.

The antibodies were expressed by the following method. Human embryonic kidney cancer-derived HEK293H cells (Invitrogen) were suspended in DMEM (Invitrogen) supplemented with 10% Fetal Bovine Serum (Invitrogen). The cells (10-ml/plate; cell density of 5 to 6×10$^5$ cells/ml) were plated on dishes for adherent cells (10 cm in diameter; CORNING) and cultured in a $CO_2$ incubator (37° C., 5% $CO_2$) for one whole day and night. Then, the medium was removed by aspiration, and 6.9 ml of CHO-S-SFM-II medium (Invitrogen) was added. The prepared plasmids (H-chain expression vector and L-chain expression vector) were introduced into cells (co-transformation) by the lipofection method. The resulting culture supernatants were collected and centrifuged (approx. 2000 g, 5 min, room temperature) to remove the cells, and sterilized through 0.22-μm filter MILLEX®-GV (Millipore). Antibodies were purified from the obtained culture supernatant by a method known to those skilled in the art using rProtein A Sepharose™ Fast Flow (Amersham Biosciences). Absorbance at 280 nm was measured using a spectrophotometer to know the purified antibody concentrations. Extinction coefficient calculated from the obtained value by the PACE method was used to calculate the antibody concentration (Protein Science 1995; 4: 2411-2423).

[Reference Example 2] Preparation of Human FcRn

FcRn is a complex of FcRn and β2-microglobulin. Oligo-DNA primers were prepared based on the human FcRn gene sequence disclosed (J. Exp. Med. (1994) 180(6), 2377-2381). A DNA fragment encoding the whole gene was prepared by PCR using human cDNA (Human Placenta Marathon-Ready cDNA, Clontech) as a template and the prepared primers. Using the obtained DNA fragment as a template, a DNA fragment encoding the extracellular domain containing the signal region (Met1-Leu290) was amplified by PCR, and inserted into an animal cell expression vector (the amino acid sequence of human FcRn as set forth in SEQ ID NO: 15). Likewise, oligo-DNA primers were prepared based on the human β2-microglobulin gene sequence disclosed (Proc. Natl. Acad. Sci. USA. (2002) 99(26), 16899-16903). A DNA fragment encoding the whole gene was prepared by PCR using human cDNA (Hu-Placenta Marathon-Ready cDNA, CLONTECH) as a template and the prepared primers. Using the obtained DNA fragment as a template, a DNA fragment encoding the whole β2-microglobulin containing the signal region (Met1-Met119) was amplified by PCR and inserted into an animal cell expression vector (the amino acid sequence of human β2-microglobulin as set forth in SEQ ID NO: 16).

Soluble human FcRn was expressed by the following procedure. The plasmids constructed for human FcRn and β2-microglobulin were introduced into cells of the human embryonic kidney cancer-derived cell line HEK293H (Invitrogen) using 10% Fetal Bovine Serum (Invitrogen) by lipofection. The resulting culture supernatant was collected, and FcRn was purified using IgG Sepharose 6 Fast Flow (Amersham Biosciences) by the method described in J. Immunol. 2002 Nov. 1; 169(9):5171-80, followed by further purification using HiTrap Q HP (GE Healthcare).

[Reference Example 3] Measurement of Plasma Antibody Concentration in Mice

Measurement of the mouse plasma antibody concentration was carried out by the ELISA method using anti-human IgG antibodies and using each of the antibodies as standards according to a method known to those skilled in the art.

INDUSTRIAL APPLICABILITY

The present invention is useful in the production of antibodies which will be administered to living organisms as pharmaceuticals. More specifically, antibodies comprising the constant regions of the present invention are advantageous in maintaining the quality of the pharmaceuticals since heterogeneity is low. In other words, by using an antibody comprising a constant region of the present invention as a pharmaceutical, a steady supply of homogeneous antibodies will be possible. For example, TOCILIZUMAB (common name) which is an antibody against the IL-6 receptor is a humanized antibody used for treatment of autoimmune diseases and such. Therefore, for example, quality can be kept stable by substituting a constant region provided by the present invention for the constant region of this antibody.

Furthermore, the present invention provided antibodies with improved pharmacokinetics by altering the amino acid sequence of the constant regions. Antibodies subjected to improvement of pharmacokinetics by the present invention maintain activity for a longer time in a living body. Therefore, for example, by substituting a constant region provided by the present invention for the constant region of TOCILIZUMAB (common name) which is an antibody against the IL-6 receptor, its pharmacokinetics is improved, and it can be an antibody that may maintain the active concentration in a living body for a long time. Furthermore, the present invention is useful also as constant regions of antibodies that can yield high biological activity in just the IgG4 isotype, since they have the same disulfide bond pattern as the IgG4 isotype.

The invention claimed is:

1. An antibody constant region comprising the amino acid sequence of SEQ ID NO: 8 (IgG2 constant region) with at least the following changes: Cys at position 102 (position 219 (EU numbering)), Cys at position 103 (position 220 (EU numbering)), His at position 147 (position 268 (EU numbering)), Arg at position 234 (position 355 (EU numbering)) and Gln at position 298 (position 419 (EU numbering)) are substituted with other amino acids; and Gly at position 325 (position 446 (EU numbering)) and Lys at position 326 (position 447 (EU numbering)) are deleted, wherein the amino acid at the carboxy terminus of the antibody constant region corresponds to EU position 445.

2. The antibody constant region of claim 1, wherein the amino acid sequence further comprises the following additional change(s) compared to SEQ ID NO: 8: at least one amino acid selected from the group consisting of Met at position 276 (position 397 (EU numbering)), Ala at position 209 (position 330 (EU numbering)), Pro at position 210 (position 331 (EU numbering)) and Thr at position 218 (position 339 (EU numbering)) is substituted with another amino acid.

3. The antibody constant region of claim 1, wherein Cys at position 102 (position 219 (EU numbering)) and Cys at position 103 (position 220 (EU numbering)) are substituted with Ser.

4. The antibody constant region of claim 1, wherein His at position 147 (position 268 (EU numbering)) is substituted with Gln, Arg at position 234 (position 355 (EU numbering)) is substituted with Gln, and Gln at position 298 (position 419 (EU numbering)) is substituted with Glu.

5. The antibody constant region of claim 1, wherein Cys at position 102 (position 219 (EU numbering)) is substituted with Ser, Cys at position 103 (position 220 (EU numbering)) is substituted with Ser, His at position 147 (position 268 (EU numbering)) is substituted with Gln, Arg at position 234 (position 355 (EU numbering)) is substituted with Gln, and Gln at position 298 (position 419 (EU numbering)) is substituted with Glu.

6. The antibody constant region of claim 2, wherein Met at position 276 (position 397 (EU numbering)) is substituted with Val.

7. The antibody constant region of claim 2, wherein Ala at position 209 (position 330 (EU numbering)) is substituted with Ser, Pro at position 210 (position 331 (EU numbering))

is substituted with Ser, and Thr at position 218 (position 339 (EU numbering)) is substituted with Ala.

8. The antibody constant region of claim 2, wherein Met at position 276 (position 397 (EU numbering)) is substituted with Val, Ala at position 209 (position 330 (EU numbering)) is substituted with Ser, Pro at position 210 (position 331 (EU numbering)) is substituted with Ser, and Thr at position 218 (position 339 (EU numbering)) is substituted with Ala.

9. The antibody constant region of claim 3, wherein the amino acid sequence further comprises the following additional change(s) compared to SEQ ID NO: 8: at least one amino acid selected from the group consisting of Met at position 276 (position 397 (EU numbering)), Ala at position 209 (position 330 (EU numbering)), Pro at position 210 (position 331 (EU numbering)) and Thr at position 218 (position 339 (EU numbering)) is substituted with another amino acid.

10. The antibody constant region of claim 9, wherein Met at position 276 (position 397 (EU numbering)) is substituted with Val.

11. The antibody constant region of claim 9, wherein Ala at position 209 (position 330 (EU numbering)) is substituted with Ser, Pro at position 210 (position 331 (EU numbering)) is substituted with Ser, and Thr at position 218 (position 339 (EU numbering)) is substituted with Ala.

12. The antibody constant region of claim 9, wherein Met at position 276 (position 397 (EU numbering)) is substituted with Val, Ala at position 209 (position 330 (EU numbering)) is substituted with Ser, Pro at position 210 (position 331 (EU numbering)) is substituted with Ser, and Thr at position 218 (position 339 (EU numbering)) is substituted with Ala.

13. The antibody constant region of claim 4, wherein the amino acid sequence further comprises the following additional change(s) compared to SEQ ID NO: 8: at least one amino acid selected from the group consisting of Met at position 276 (position 397 (EU numbering)), Ala at position 209 (position 330 (EU numbering)), Pro at position 210 (position 331 (EU numbering)) and Thr at position 218 (position 339 (EU numbering)) is substituted with another amino acid.

14. The antibody constant region of claim 13, wherein Met at position 276 (position 397 (EU numbering)) is substituted with Val.

15. The antibody constant region of claim 13, wherein Ala at position 209 (position 330 (EU numbering)) is substituted with Ser, Pro at position 210 (position 331 (EU numbering)) is substituted with Ser, and Thr at position 218 (position 339 (EU numbering)) is substituted with Ala.

16. The antibody constant region of claim 13, wherein Met at position 276 (position 397 (EU numbering)) is substituted with Val, Ala at position 209 (position 330 (EU numbering)) is substituted with Ser, Pro at position 210 (position 331 (EU numbering)) is substituted with Ser, and Thr at position 218 (position 339 (EU numbering)) is substituted with Ala.

17. The antibody constant region of claim 5, wherein the amino acid sequence further comprises the following additional change(s) compared to SEQ ID NO: 8: at least one amino acid selected from the group consisting of Met at position 276 (position 397 (EU numbering)), Ala at position 209 (position 330 (EU numbering)), Pro at position 210 (position 331 (EU numbering)) and Thr at position 218 (position 339 (EU numbering)) is substituted with another amino acid.

18. The antibody constant region of claim 17, wherein Met at position 276 (position 397 (EU numbering)) is substituted with Val.

19. The antibody constant region of claim 17, wherein Ala at position 209 (position 330 (EU numbering)) is substituted with Ser, Pro at position 210 (position 331 (EU numbering)) is substituted with Ser, and Thr at position 218 (position 339 (EU numbering)) is substituted with Ala.

20. The antibody constant region of claim 17, wherein Met at position 276 (position 397 (EU numbering)) is substituted with Val, Ala at position 209 (position 330 (EU numbering)) is substituted with Ser, Pro at position 210 (position 331 (EU numbering)) is substituted with Ser, and Thr at position 218 (position 339 (EU numbering)) is substituted with Ala.

21. An antibody comprising the antibody constant region of claim 1.

22. A pharmaceutical composition comprising the antibody of claim 21.

23. An antibody comprising the antibody constant region of claim 2.

24. A pharmaceutical composition comprising the antibody of claim 23.

25. An antibody comprising the antibody constant region of claim 9.

26. A pharmaceutical composition comprising the antibody of claim 25.

27. An antibody comprising the antibody constant region of claim 13.

28. A pharmaceutical composition comprising the antibody of claim 27.

29. An antibody constant region comprising the amino acid sequence of SEQ ID NO: 8 (IgG2 constant region) with only the following changes:
   (a) Cys at position 102 (position 219 (EU numbering)), Cys at position 103 (position 220 (EU numbering)), His at position 147 (position 268 (EU numbering)), Arg at position 234 (position 355 (EU numbering)) and Gln at position 298 (position 419 (EU numbering)) are substituted with other amino acids;
   (b) Gly at position 325 (position 446 (EU numbering)) and Lys at position 326 (position 447 (EU numbering)) are deleted; and
   (c) optionally, at least one amino acid selected from the group consisting of Met at position 276 (position 397 (EU numbering)), Ala at position 209 (position 330 (EU numbering)), Pro at position 210 (position 331 (EU numbering)) and Thr at position 218 (position 339 (EU numbering)) is substituted with another amino acid,
   wherein the amino acid at the carboxy terminus of the antibody constant region corresponds to EU position 445.

30. The antibody constant region of claim 29, wherein at least one amino acid selected from the group consisting of Met at position 276 (position 397 (EU numbering)), Ala at position 209 (position 330 (EU numbering)), Pro at position 210 (position 331 (EU numbering)) and Thr at position 218 (position 339 (EU numbering)) is substituted with another amino acid.

31. The antibody constant region of claim 30, wherein Met at position 276 (position 397 (EU numbering)) is substituted with Val.

32. The antibody constant region of claim 30, wherein Ala at position 209 (position 330 (EU numbering)) is substituted with Ser, Pro at position 210 (position 331 (EU numbering)) is substituted with Ser, and Thr at position 218 (position 339 (EU numbering)) is substituted with Ala.

33. The antibody constant region of claim 30, wherein Met at position 276 (position 397 (EU numbering)) is substituted with Val, Ala at position 209 (position 330 (EU numbering)) is substituted with Ser, Pro at position 210 (position 331 (EU numbering)) is substituted with Ser, and Thr at position 218 (position 339 (EU numbering)) is substituted with Ala.

34. The antibody constant region of claim 30, wherein Cys at position 102 (position 219 (EU numbering)) is substituted with Ser, and Cys at position 103 (position 220 (EU numbering)) is substituted with Ser.

35. The antibody constant region of claim 34, wherein Met at position 276 (position 397 (EU numbering)) is substituted with Val.

36. The antibody constant region of claim 34, wherein Ala at position 209 (position 330 (EU numbering)) is substituted with Ser, Pro at position 210 (position 331 (EU numbering)) is substituted with Ser, and Thr at position 218 (position 339 (EU numbering)) is substituted with Ala.

37. The antibody constant region of claim 34, wherein Met at position 276 (position 397 (EU numbering)) is substituted with Val, Ala at position 209 (position 330 (EU numbering)) is substituted with Ser, Pro at position 210 (position 331 (EU numbering)) is substituted with Ser, and Thr at position 218 (position 339 (EU numbering)) is substituted with Ala.

38. The antibody constant region of claim 30, wherein His at position 147 (position 268 (EU numbering)) is substituted with Gln, Arg at position 234 (position 355 (EU numbering)) is substituted with Gln, and Gln at position 298 (position 419 (EU numbering)) is substituted with Glu.

39. The antibody of claim 38, wherein Met at position 276 (position 397 (EU numbering)) is substituted with Val.

40. The antibody of claim 38, wherein Ala at position 209 (position 330 (EU numbering)) is substituted with Ser, Pro at position 210 (position 331 (EU numbering)) is substituted with Ser, and Thr at position 218 (position 339 (EU numbering)) is substituted with Ala.

41. The antibody of claim 38, wherein Met at position 276 (position 397 (EU numbering)) is substituted with Val, Ala at position 209 (position 330 (EU numbering)) is substituted with Ser, Pro at position 210 (position 331 (EU numbering)) is substituted with Ser, and Thr at position 218 (position 339 (EU numbering)) is substituted with Ala.

42. The antibody constant region of claim 30, wherein Cys at position 102 (position 219 (EU numbering)) is substituted with Ser, Cys at position 103 (position 220 (EU numbering)) is substituted with Ser, His at position 147 (position 268 (EU numbering)) is substituted with Gln, Arg at position 234 (position 355 (EU numbering)) is substituted with Gln, and Gln at position 298 (position 419 (EU numbering)) is substituted with Glu.

43. The antibody constant region of claim 42, wherein Met at position 276 (position 397 (EU numbering)) is substituted with Val.

44. The antibody constant region of claim 42, wherein Ala at position 209 (position 330 (EU numbering)) is substituted with Ser, Pro at position 210 (position 331 (EU numbering)) is substituted with Ser, and Thr at position 218 (position 339 (EU numbering)) is substituted with Ala.

45. The antibody constant region of claim 42, wherein Met at position 276 (position 397 (EU numbering)) is substituted with Val, Ala at position 209 (position 330 (EU numbering)) is substituted with Ser, Pro at position 210 (position 331 (EU numbering)) is substituted with Ser, and Thr at position 218 (position 339 (EU numbering)) is substituted with Ala.

46. An antibody comprising the antibody constant region of claim 30.

47. A pharmaceutical composition comprising the antibody of claim 46.

* * * * *